(12) United States Patent
Bennani et al.

(10) Patent No.: US 7,732,618 B2
(45) Date of Patent: Jun. 8, 2010

(54) BENZIMIDAZOLE ACETIC ACIDS EXHIBITING CRTH2 RECEPTOR ANTAGONISM AND USES THEREOF

(75) Inventors: Youssef L. Bennani, Shaker Heights, OH (US); Lawrence Nathan Tumey, Fairview Park, OH (US); Elizabeth Ann Gleason, Rocky River, OH (US); Michael Joseph Robarge, Burton, OH (US)

(73) Assignee: Wyeth, Madison, NJ (US)

( * ) Notice: Subject to any disclaimer, the term of this patent is extended or adjusted under 35 U.S.C. 154(b) by 16 days.

(21) Appl. No.: 11/230,916

(22) Filed: Sep. 21, 2005

(65) Prior Publication Data

US 2006/0106081 A1   May 18, 2006

Related U.S. Application Data

(60) Provisional application No. 60/611,296, filed on Sep. 21, 2004.

(51) Int. Cl.
*A61K 31/4184*   (2006.01)
*C07D 235/04*   (2006.01)

(52) U.S. Cl. ............................. 548/310.1; 514/394

(58) Field of Classification Search ............... 548/310.1
See application file for complete search history.

(56) References Cited

U.S. PATENT DOCUMENTS

| | | | |
|---|---|---|---|
| 3,590,047 A | 6/1971 | Shen et al. | |
| 5,612,360 A | 3/1997 | Boyd et al. | |
| 6,114,532 A | 9/2000 | Ries et al. | |
| 6,121,308 A | 9/2000 | Hauel et al. | |
| 6,365,584 B1 * | 4/2002 | Anderskewitz et al. | 514/217.09 |

FOREIGN PATENT DOCUMENTS

| | | |
|---|---|---|
| JP | 62-24244 | 2/1987 |
| JP | 2000-95767 | 4/2000 |
| JP | 2000-143635 | 5/2000 |
| WO | WO 97/10219 A1 | 3/1997 |
| WO | WO 02/060438 | 8/2002 |
| WO | WO 03/101981 | 12/2003 |

OTHER PUBLICATIONS

An English translation of Sakamoto et al., JP 62-24244, 1987.*
Corrected English translation of Sakamoto et al., JP 62-24244, 1987.*

Bohm, E., et al., "11-Dehydro-thromboxane $B_2$, a Stable Thromboxane Metabolite, Is a Full Agonist of Chemoattractant Receptor-homologous Molecule Expressed on TH2 Cells (CRTH2) in Human Eosinophils and Basophils," *J. Biol. Chem.* 279:7663-7670, The American Society for Biochemistry and Molecular Biology, Inc. (Feb. 2004).

Boie, Y., et al., "Molecular Cloning and Characterization of the Human Prostanoid DP Receptor," 270:18910-18916, The American Society for Biochemistry and Molecular Biology, Inc. (1995).

Fujitani, Y., et al., "Pronounced Eosinophilic Lung Inflammation and Th2 Cytokine Release in Human Lipocalin-Type Prostaglandin D Synthase Transgenic Mice," *J. Immunol.* 168:443-449, The American Association of Immunologists (2002).

Hirai, H., et al., "Prostaglandin D2 Selectively Induces Chemotaxis in T Helper Type 2 Cells, Eosinophils, and Basophils via Seven-Transmembrane Receptor CRTH2," *J. Exp. Med.* 193:255-261, The Rockefeller University Press (2001).

Liu, M.C., et al., "Evidence for Elevated Levels of Histamine, Prostaglandin $D_2$, and Other Bronchoconstricting Prostaglandins in the Airways of Subjects with Mild Asthma," *Am. Rev. Respir. Dis.* 142:126-132, American Lung Association (1990).

Nagata, K., et al., "Selective Expression of a Novel Surface Molecule by Human Th2 Cells In Vivo," *J. Immunol.* 162:1278-1286, American Association of Immunologists (1999).

Patent Abstracts of Japan, English language abstract of JP62-024244, 1987.

Patent Abstracts of Japan, English language abstract of JP2000-095767, 2000.

Patent Abstracts of Japan, English language abstract of JP2000-143635, 2000.

International Search Report for PCT Application No. PCT/US2005/034028 dated Mar. 23, 2006.

International Search Report for corresponding PCT Application No. PCT/US2005/034029 dated Apr. 27, 2007.

* cited by examiner

*Primary Examiner*—Laura L. Stockton
(74) *Attorney, Agent, or Firm*—Finnegan, Henderson, Farabow, Garrett & Dunner, LLP

(57) ABSTRACT

The invention relates to benzimidazole acetic acid compounds which function as antagonists of the Chemoattractant Receptor-homologous molecule expressed on T-Helper type 2 cells (CRTH2) receptor. The invention also relates to the use of these compounds to inhibit the binding of prostaglandin $D_2$ and its metabolites or certain thromboxane metabolites to the CRTH2 receptor and to treat disorders responsive to such inhibition.

6 Claims, No Drawings

BENZIMIDAZOLE ACETIC ACIDS EXHIBITING CRTH2 RECEPTOR ANTAGONISM AND USES THEREOF

BACKGROUND OF THE INVENTION

1. Field of the Invention

This invention is in the field of medicinal chemistry. In particular, the invention relates to benzimidazole acetic acid compounds which function as antagonists of the Chemoattractant Receptor-homologous molecule expressed on T-Helper type 2 cells (CRTH2) receptor. The invention also relates to the use of these compounds to inhibit the binding of prostaglandin $D_2$ and its metabolites to the CRTH2 receptor and to treat disorders responsive to such inhibition.

2. Related Art

The CRTH2 receptor binds prostaglandin $D_2$ ($PGD_2$) and its metabolites. Efforts have been made to inhibit the binding of $PGD_2$ to the CRTH2 receptor in order to treat disorders and diseases related to excess levels of $PGD_2$.

Elevated $PGD_2$ is thought to play a causative role in both asthma and atopic dermatitis. For example, $PGD_2$ is one of the major prostanoids released by mast cells in the asthmatic lung and this molecule is found at high levels in the bronchial fluid of asthmatics (Liu et al., *Am. Rev. Respir. Dis.* 142:126 (1990)). Evidence of a role of $PGD_2$ in asthma is provided by a recent publication examining the effects of overexpression of prostaglandin D synthase on induction of allergic asthma in transgenic mice (Fujitani, *J. Immunol.* 168:443 (2002)). After allergen challenge, these animals had increased $PGD_2$ in the lungs, and the number of Th2 cells and eosinophils were greatly elevated relative to non-transgenic animals. These results are $PGD_2$ can bind to two G-protein coupled receptors, DP (Boie et al., *J. Biol. Chem.* 270:18910 (1995)) and CRTH2 (Nagata et al., *J. Immunol.* 162:1278 (1999); Hirai et al., *J. Exp. Med.* 193:255 (2001)). The latter receptor might play a particularly important role in diseases such as asthma and atopic dermatitis that are characterized by Th2 cell involvement, since Th2 cell chemotaxis in response to $PGD_2$ appears to be mediated by CRTH2 (Hirai et al., above). Moreover, eosinophils, the major inflammatory cell type seen in asthmatic lungs, show a CRTH2-mediated chemotactic response to $PGD_2$ (Hirai et al.) and certain thromboxane metabolites (Bohm et al., *J. Biol. Chem.* 279:7663 (2004)).

JP2000143635 and JP2000095767 disclose compounds of the following formula that are neovascularization inhibitors:

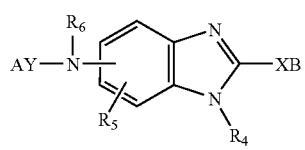

wherein A is a substituted or unsubstituted phenyl ring; B is a substituted or unsubstituted cyclyl; $R_4$ and $R_6$ are H, optionally substituted $C_{1-6}$ alkyl, $C_{2-6}$ alkenyl, $C_{3-7}$ cycloalkyl, optionally substituted $C_{7-13}$ aralkyl, or $C_{2-7}$ alkoxycarbonyl; $R_5$ is H, halo, optionally substituted $C_{1-6}$ alkyl, $C_{1-6}$ alkoxy, $C_{2-7}$ alkoxycarbonyl, mono- or di($C_{1-6}$ alkyl)amino, or optionally substituted carbamoyl; X is a direct bond, $C_{1-6}$ alkylene, $C_{2-6}$ alkenylene, $C_{1-6}$ alkylene-aminocarbonyl, or $C_{1-6}$ alkylene-oxycarbonylamino; Y is CO, $SO_2$, NHCO, $C_{1-6}$ alkylenecarbonyl, $C_{2-6}$ alkenylenecarbonyl, or $C_{1-6}$ alkylene.

JP62024244 discloses compounds of the following formula that can be used as part of photographic photosensitive materials:

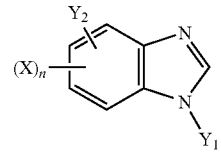

wherein $Y_1$ is H, $R_1$, $COR_2$, or $SO_2R_3$; $Y_2$ is H, $NHR_4$, $NHCOR_5$, or $NHSO_2R_6$; $R_1$, $R_2$, $R_3$, $R_5$, and $R_6$ are aliphatic or aromatic moieties; $R_4$ is H or $R_1$; $Y_1$ and $Y_2$ cannot be H simultaneously; when $R_4$ is H, $Y_1$ is not H; X is halo, alkyl, aryl, aralkyl, alkoxy, OH, $NO_2$, or CN; and n is 0, 1, or 2.

U.S. Pat. No. 6,121,308 discloses compounds of the following formula that can be used to treat thrombotic disease:

wherein B denotes an ethylene group optionally substituted by one or two $C_{1-3}$ alkyl groups, wherein a methylene group of the ethylene group, which is linked to either the Het or Ar group, may be replaced by an oxygen or sulphur atom, by a sulphinyl, sulphonyl, carbonyl or —$NR_1$ group, whilst $R_1$ denotes a hydrogen atom or a $C_{1-6}$-alkyl group;

B also denotes a straight-chained $C_{3-5}$-alkylene group, in which a methylene group, which is linked neither to the Het group nor to the Ar group, is replaced by an —$NR_1$ group wherein $R_1$ is as hereinbefore defined;

E denotes a cyano or $R_bNH$—C(=NH)—group wherein $R_b$ denotes a hydrogen atom, a hydroxy group, a $C_{1-3}$-alkyl group or a group which may be cleaved in vivo;

Ar denotes a phenylene or naphthylene group optionally substituted by a fluorine, chlorine or bromine atom, or by a trifluoromethyl, $C_{1-3}$-alkyl or $C_{1-3}$-alkoxy group, a thienylene, thiazolylene, pyridinylene, pyrimidinylene, pyazinylene or pyridazinylene group optionally substituted in the carbon skeleton by a $C_{1-3}$ alkyl group;

Het denotes a bicyclic heterocycle of the formula

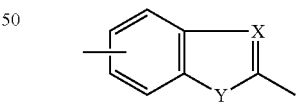

wherein X denotes a nitrogen atom or a methine group optionally substituted by a $C_{1-3}$-alkyl group and Y denotes an imino group optionally substituted by a $C_{1-5}$-alkyl or $C_{3-7}$-cycloalkyl group, an oxygen or sulphur atom or X denotes a nitrogen atom and Y denotes an imino group substituted by a $C_{1-5}$-alkyl or $C_{3-7}$-cycloalkyl group, wherein the alkyl and cycloalkyl substituent in each case is substituted by a carboxy group or a group which can be converted in vivo into a carboxy group, wherein additionally in one of the abovementioned heterocycles a non-angular methine group may be replaced by a nitrogen atom;

or Het denotes a group of the formulae

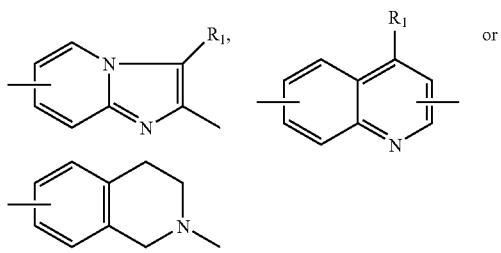

wherein $R_1$ is as hereinbefore defined, and $R_a$ denotes a phenyl-$C_{1-3}$ alkoxy group, an amino group, a $C_{1-3}$-alkylamino group, which is additionally substituted at the nitrogen atom by a phenyl-$C_{1-3}$ alkyl group, a $R_3$-CO-$R_4$N or $R_3$-SO$_2$-$R_4$N group wherein $R_3$ denotes a $C_{1-5}$-alkyl, phenyl-$C_{1-3}$-alkyl, $C_{3-7}$-cycloalkyl, phenyl, naphthyl, pyridyl, quinolyl, isoquinolyl, tetrahydroquinolyl or tetrahydroisoquinolyl group and $R_4$ denotes a hydrogen atom, $C_{1-5}$-alkyl or phenyl-$C_{1-3}$-alkyl group, each of which is substituted in the alkyl moiety by a group which may be converted in vivo into a carboxy group, by a carboxy or tetrazolyl group, by an aminocarbonyl or $C_{1-3}$-alkylaminocarbonyl group, each of which is additionally substituted at the nitrogen atom by a group which may be converted in vivo into a carboxy-$C_{1-3}$-alkyl group or by a carboxy group, a $C_{2-5}$-alkyl group terminally substituted by a di-($C_{1-3}$-alkyl)-amino group, or a $C_{3-7}$-cycloalkyl group.

U.S. Pat. No. 6,114,532 discloses compounds of the following formula that can be used to treat thrombotic disease:

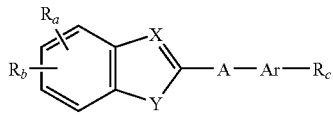

wherein A denotes an oxygen or sulphur atom, a carbonyl, sulphinyl or sulphonyl group, an imino group optionally substituted by a $C_{1-3}$-alkyl group or a methylene group optionally mono- or disubstituted by a carboxy-$C_{1-3}$-alkyl- or $C_{1-3}$-alkoxycarbonyl-$C_{1-3}$-alkyl group;

Ar denotes a phenylene or naphthylene group each optionally substituted by a fluorine, chlorine or bromine atom, by a trifluoromethyl, $C_{1-3}$-alkyl- or $C_{1-3}$-alkoxy group, a thienylene, thiazolylene, pyridinylene, pyrimidinylene, pyrazinylene or pyridazinylene group each optionally substituted in the carbon skeleton by a $C_{1-3}$-alkyl group;

X denotes a nitrogen atom or an —$R_1$C= group wherein $R_1$ denotes a hydrogen, fluorine, chlorine, bromine or iodine atom, a $C_{1-3}$-alkyl or $C_{1-3}$-alkoxy group;

Y denotes an oxygen or sulphur atom or an —$R_2$N— group, wherein $R_2$ denotes a hydrogen atom or a $C_{1-5}$-alkyl group, a $C_{1-3}$-alkyl group, which is substituted by a phenyl group optionally substituted by a carboxy or $C_{1-3}$-alkoxycarbonyl group, a $C_{1-5}$-alkyl group, which is substituted by a carboxy, $C_{1-3}$-alkoxycarbonyl, carboxy-$C_{1-3}$-alkoxycarbonyl, $C_{1-3}$-alkoxycarbonyl-$C_{1-3}$-alkoxycarbonyl, carboxy-$C_{1-3}$-alkyl-aminocarbonyl or $C_{1-3}$-alkoxycarbonyl-$C_{1-3}$-alkylaminocarbonyl group, or an n-$C_{2-4}$-alkyl group, which is terminally substituted by a di-($C_{1-3}$-alkyl)-amino, pyrrolidino, piperidino, morpholino, piperazino or N—$C_{1-3}$-alkyl-piperazino group, wherein the abovementioned cyclic groups may additionally be substituted by one or two $C_{1-3}$-alkyl groups;

$R_a$ denotes a hydrogen atom or a $C_{1-3}$-alkyl group;

$R_b$ denotes a $R_3$—CO—$C_{3-5}$-cycloalkylene, $R_3$—SO$_2$—NR$_4$, $R_3$—CO—NR$_4$, $R_5$NR$_6$—CO, $R_5$NR$_6$—SO$_2$— or RNR$_6$—CO—$C_{3-5}$-cycloalkylene group, wherein $R_3$ denotes a $C_{1-6}$-alkyl- or $C_{5-7}$-cycloalkyl group, a $C_{1-3}$-alkyl group, which is substituted by a $C_{5-7}$-cyclo-alkyl, phenyl, $C_{1-3}$-alkylamino, di-($C_{1-3}$-alkyl)-amino, carboxy-$C_{1-3}$-alkylamino, $C_{1-3}$-alkoxycarbonylamino, phenylsulphonylamino or tetrazolyl group, a $C_{1-3}$-alkyl group, which is substituted by a carboxy, $C_{1-3}$-alkoxycarbonyl, carboxy-$C_{1-3}$-alkoxy or $C_{1-3}$-alkoxy-carbonyl-$C_{1-3}$-alkoxy group, a $C_{1-3}$-alkyl group, which is substituted by an imidazolyl or benzimidazolyl group, wherein the imidazole moiety of the abovementioned groups may be substituted by one or two $C_{1-3}$-alkyl groups or by a carboxy-$C_{1-3}$-alkyl or $C_{1-3}$-alkoxycarbonyl-$C_{1-3}$-alkyl group, a phenyl group optionally mono or disubstituted by $C_{1-3}$-alkyl, $C_{1-3}$-alkoxy, trifluoromethyl, carboxy or $C_{1-3}$-alkoxycarbonyl groups, wherein the substituents may be identical or different, a phenyl group substituted by 3 or 4 methyl groups, a naphthyl, pyridinyl, pyrazolyl, quinolyl or isoquinolyl group each optionally substituted by a $C_{1-3}$-alkyl group;

$R_4$ denotes a hydrogen atom, a $C_{1-5}$-alkyl or $C_{5-7}$-cycloalkyl group, a $C_{1-5}$-alkyl group, which is substituted by a carboxy group or by a $C_{1-5}$-alkoxycarbonyl group wherein the alkoxy moiety in the 2 or 3 position may additionally be substituted by a hydroxy group, a $C_{1-3}$-alkyl group, which is substituted by an aminocarbonyl, hydroxyaminocarbonyl, $C_{1-3}$-alkylamino-carbonyl, di-($C_{1-3}$-alkyl)-aminocarbonyl or $C_{5-7}$-alkylene-iminocarbonyl group, wherein the $C_{6-7}$-alkyleneimino moiety may additionally be substituted in the 4 position by a di-($C_{1-3}$-alkyl)-amino group, an optionally phenyl-substituted $C_{1-3}$-alkyl group, which is substituted in the alkyl moiety by a carboxy-$C_{1-3}$-alkoxycarbonyl, $C_{1-3}$-alkoxycarbonyl-$C_{1-3}$-alkoxycarbonyl, carboxy-$C_{1-3}$-alkylaminocarbonyl, N—($C_{1-3}$-alkyl)-carboxy-$C_{1-3}$-alkylaminocarbonyl, $C_{1-3}$-alkoxycarbonyl-$C_{1-3}$-alkylaminocarbonyl, N—($C_{1-3}$-alkyl)-$C_{1-3}$-alkoxycarbonyl-$C_{1-3}$-alkylaminocarbonyl, morpholinocarbonyl or 4-($C_{1-3}$-alkyl)-piperazinocarbonyl group, a $C_{1-3}$-alkyl group, which is substituted by a carboxy-$C_{1-3}$-alkylaminocarbonyl, N—($C_{1-3}$-alkyl)-carboxy-$C_{1-3}$-alkylaminocarbonyl, $C_{1-3}$-alkoxycarbonyl-$C_{1-3}$-alkylaminocarbonyl or N—($C_{1-3}$-alkyl)-$C_{1-3}$-alkoxycarbonyl-$C_{1-3}$-alkylamino-carbonyl group, which are additionally substituted at a carbon atom of the alkylamino moiety by a carboxy or $C_{1-3}$-alkoxycarbonyl group, a $C_{1-3}$-alkyl group, which is substituted by a di-($C_{1-3}$-alkyl)-aminocarbonyl group wherein an alkyl moiety may additionally be substituted in the 2 or 3 position by a di-($C_{1-3}$-alkyl)-amino group, a $C_{1-3}$-alkyl group, which is substituted by a 4-(morpholinocarbonyl-$C_{1-3}$-alkyl)-piperazinocarbonyl, N—($C_{1-3}$-alkyl)-pyrrolidinyl or N—($C_{1-3}$-alkyl)-piperidinyl group, or an n-$C_{2-4}$-alkyl group, which is terminally substituted by a di-($C_{1-3}$-alkyl)-amino, $C_{5-7}$-alkyleneimino or morpholino group;

$R_5$ denotes a $C_{1-5}$-alkyl or $C_{5-7}$-cycloalkyl group, a phenyl-$C_{1-3}$-alkyl group, which may be substituted in the alkyl moiety by a carboxy or $C_{1-3}$-alkoxycarbonyl group, an n-$C_{2-4}$-alkyl group, which is substituted in the 2, 3 or 4 position by a hydroxy, $C_{1-3}$-alkylamino or di-($C_{1-3}$-alkyl)-amino group, a phenyl group optionally mono or disubstituted by a $C_{1-3}$-alkyl, $C_{1-3}$-alkoxy, trifluoromethyl, carboxy or $C_{1-3}$-alkoxycarbonyl group, wherein the substituents may be identical or different, a phenyl group substituted by 3 or 4 methyl groups, a naphthyl, pyridinyl, quinolyl or isoquinolyl group;

$R_6$ denotes a $C_{1-5}$-alkyl group optionally substituted by a carboxy or $C_{1-3}$-alkoxycarbonyl group, a $C_{1-3}$-alkyl group, which is substituted in the alkyl moiety by a $C_{1-3}$-alkylaminocarbonyl, di-($C_{1-3}$-alkyl)-aminocarbonyl, carboxy-$C_{1-3}$-alkylaminocarbonyl or $C_{1-3}$-alkyloxycarbonyl-$C_{1-3}$-alkylaminocarbonyl group, or an n-$C_{2-4}$-alkyl group, which is substituted in the 2, 3 or 4 position by a hydroxy, $C_{1-3}$-alkylamino or di-($C_{1-3}$-alkyl)-amino group, or one of the groups $R_5$ or $R_6$ denotes a hydrogen atom, wherein the other one of the groups has the meanings given for $R_5$ and $R_6$ hereinbefore, or $R_5$ and $R_6$ together with the nitrogen atom between them denote a pyrrolidino or piperidino group optionally substituted by one or two $C_{1-3}$-alkyl groups, which may additionally be substituted by a carboxy-$C_{1-3}$-alkyl or $C_{1-3}$-alkoxy-$C_{1-3}$-alkyl group or on to which a benzene ring may be condensed via two adjacent carbon atoms, or $R_b$ denotes an amino, $C_{1-3}$-alkylamino or $C_{5-7}$-cycloalkyl-amino group, which may be substituted at the nitrogen atom by a phenylaminocarbonyl, N-phenyl-$C_{1-3}$-alkylaminocarbonyl, phenylsulphonylamino-$C_{1-3}$-alkylcarbonyl, $C_{1-3}$-alkyloxycarbonyl-$C_{1-3}$-alkyl, N—($C_{3-5}$-cycloalkyl)-$C_{1-3}$-alkylamino-carbonyl, N-(hydroxycarbonyl-$C_{1-3}$-alkyl)-aminocarbonyl, N—($C_{1-3}$-alkoxycarbonyl-$C_{1-3}$-alkyl)-aminocarbonyl-$C_{3-5}$-cycloalkylamino group, a piperidino group substituted in the 4 position by a di-($C_{1-3}$-alkyl)-amino group, a piperazino group substituted in the 4 position by a $C_{1-3}$-alkyl group, a $C_{2-4}$-alkylsulphonyl group, which is substituted in the 2, 3 or 4 position by a di-($C_{1-3}$-alkyl)-amino group, a 4-oxo-3,4-dihydro-phthalazinyl-1-yl or 4-oxo-2,3-diaza-spiro[5.5]undec-1-en-1-yl group, a methyl group substituted by a $C_{5-7}$-cycloalkyleneiminocarbonyl group wherein the methyl group is substituted by a carboxy-$C_{1-3}$-alkyl or $C_{1-3}$-alkoxy-$C_{1-3}$-alkyl group, a carbonyl or methyl group substituted by a $C_{3-5}$-cycloalkyl or $C_{3-5}$-alkyl group, wherein the cycloalkyl moiety may additionally be substituted by a $C_{1-3}$-alkyl, carboxy-$C_{1-3}$-alkyl or $C_{1-3}$-alkoxycarbonyl-$C_{1-3}$-alkyl group and the methyl moiety is substituted by a $C_{1-3}$-alkoxy or $C_{1-4}$-alkylamino group, a $C_{5-7}$-cycloalkyl-N-(carboxy-$C_{1-3}$-alkoxy)-iminomethylene or $C_{5-7}$-cycloalkyl-N—($C_{1-3}$-alkoxycarbonyl-$C_{1-3}$-alkoxy)-iminomethylene group, which may additionally be substituted in the cycloalkyl moiety by a $C_{1-3}$-alkyl group, a phosphinyl group, which is substituted by a $C_{1-6}$-alkyl or $C_{5-7}$-cycloalkyl group and by a hydroxy, $C_{1-3}$-alkoxy, carboxy-$C_{1-3}$-alkoxy or $C_{1-3}$-alkoxycarbonyl-$C_{1-3}$-alkoxy group, a piperidino group wherein in the 2 position a methylene group is replaced by a carbonyl or sulphonyl group, a tetrazolyl group optionally substituted by a $C_{1-5}$-alkyl group, a phenyl or phenylsulphonyl group optionally mono or disubstituted by a $C_{1-3}$-alkyl, $C_{1-3}$-alkoxy, trifluoromethyl, carboxy or $C_{1-3}$-alkoxycarbonyl group, wherein the substituents may be identical or different, a sulphimidoyl group, which is substituted at the sulphur atom by a $C_{5-7}$-cycloalkyl group and may additionally be substituted at the nitrogen atom by a $C_{2-4}$-alkanoyl, carboxy-$C_{1-3}$-alkyl, $C_{1-3}$-alkoxycarbonyl-$C_{1-3}$-alkyl, carboxy-$C_{2-4}$-alkanoyl or $C_{1-3}$-alkoxycarbonyl-$C_{2-4}$-alkanoyl group, an imidazolyl group substituted in the 1 position by a carboxy-$C_{1-3}$-alkyl or $C_{1-3}$-alkoxycarbonyl-$C_{1-3}$-alkyl group, which may additionally be substituted by a $C_{1-5}$-alkyl group, a $C_{1-3}$-alkoxycarbonyl-$C_{1-3}$-alkyl group, which is substituted in the alkyl moiety by a $C_{5-7}$-cycloalkylaminocarbonyl group, a $C_{1-3}$-alkyl group, which is substituted by a 1-imidazolyl group, wherein the imidazolyl moiety may additionally be substituted by one or two $C_{1-3}$-alkyl groups, or in the 2 position by a 1-benzimidazolyl group substituted by a carboxy-$C_{1-3}$-alkyl or $C_{1-3}$-alkoxycarbonyl-$C_{1-3}$-alkyl group, or a furanyl-1-pyrazolyl group optionally substituted by a $C_{1-3}$-alkyl group; and $R_c$ denotes a cyano group or an amidino group, which may be substituted by a hydroxy group, by one or two $C_{1-3}$-alkyl groups, by one or two $C_{1-8}$-alkoxycarbonyl groups or by a group which can be cleaved in vivo.

WO 97/10219 discloses compounds of the following formula that can be used to treat metabolic bone disease:

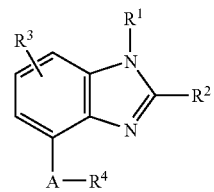

wherein $R^1$ is acyl, lower alkenyl or lower alkyl optionally substituted with substituent(s) selected from the group consisting of aryl, substituted aryl, a heterocyclic group, a substituted heterocyclic group, hydroxy, substituted hydroxy, cyano, halogen, amino, substituted amino, acyl, mercapto, substituted mercapto, hydroxyamidino, substituted hydroxyamidino, and substituted hydrazino, and $R^2$ is hydrogen, lower alkyl, hydroxy(lower)alkyl, halo(lower)alkyl, lower alkoxy, lower alkylthio, acyl, or cyano, or $R^1$ and $R^2$ are taken together to form lower alkylene or lower alkenylene, each of which may include O, S, or N-$R^5$ in the chain, in which $R^5$ is hydrogen or lower alkyl, $R^3$ is hydrogen or halogen, $R^4$ is a heterocyclic group or aryl, each of which may be substituted with suitable substituent(s), and A is

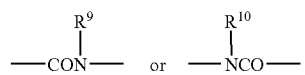

in which $R^9$ is hydrogen, lower alkyl, or substituted lower alkyl, and $R^{10}$ is hydrogen, lower alkyl, or substituted lower alkyl.

U.S. Pat. No. 5,612,360 discloses compounds of the following formula that are angiotensin II receptor antagonists:

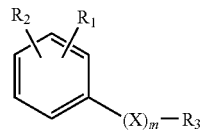

wherein $R_1$ is $CO_2H$, $SO_3H$, $PO_3H_2$, $CONHSO_2R_8$, or 5-tetrazolyl;

$R_2$ is H, —OH, —OCOCH$_3$, halo, $C_1$-$C_4$ alkyl, or $C_1$-$C_4$ alkoxy;

R₃ is

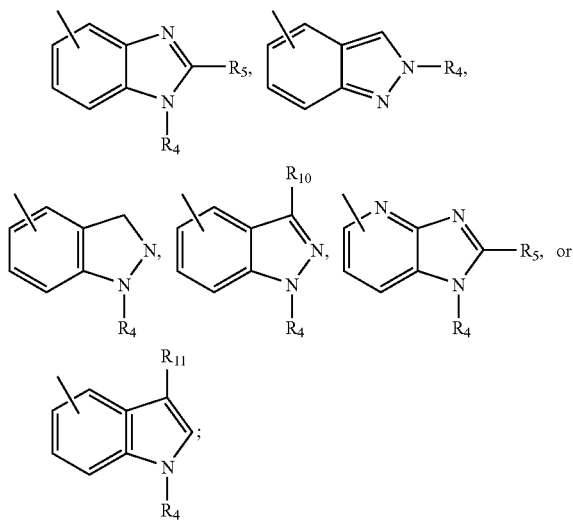

X is —(CH₂)ₘCONH—, —(CH₂)ₘNHCO—, —CH₂—, —O—, —NH—, or —(CH₂)ₘCO—;
R₄ is

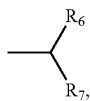

$C_4$-$C_9$ straight chain alkyl, or $C_4$-$C_9$ straight chain trifluoroalkyl providing when R₄ is a $C_4$-$C_9$ straight chain alkyl or trifluoroalkyl R₃ must be (a) or (d);
R₅ is H, $C_1$-$C_5$ alkyl, $C_1$-$C_5$ trifluoroalkyl, (CF₂)ₙCF₃, benzyl, —(CH₂)ₘN(C₁-C₃ alkyl)₂, —(CH₂)ₘNH(C₁-C₃ alkyl), —CH₂-1-pyrrolidine, —(CH₂)ₙCO₂H, or

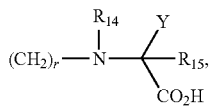

R₆ is (CH₂)ₚR₁, —CONH(C₁-C₄ alkyl), —CONH(C₁-C₄ trifluoroalkyl), —COO(C₁-C₄ alkyl), —COO(C₁-C₄ trifluoroalkyl), —CONH(hydroxy-C₁-C₄ alkyl),

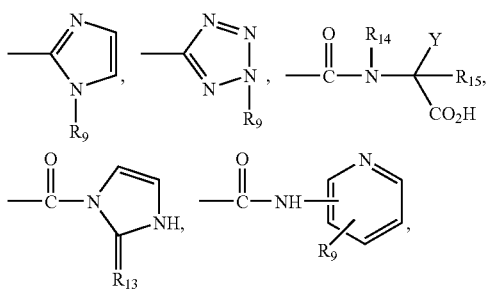

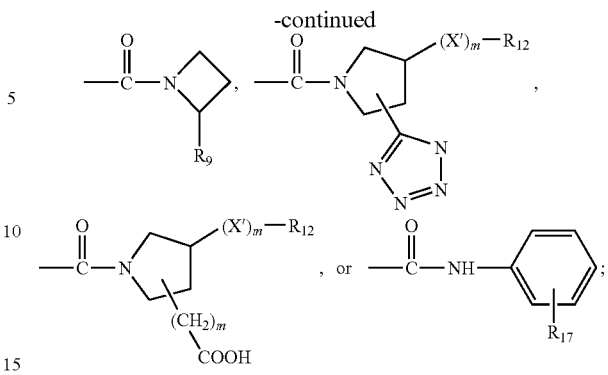

R₇ is $C_4$-$C_9$ straight chain alkyl, $C_4$-$C_9$ straight chain trifluoroalkyl, $C_4$-$C_9$ straight chain alkenyl, or $C_4$-$C_9$ straight chain trifluoroalkenyl;
R₈ is phenyl, $C_1$-$C_4$ alkyl substituted phenyl, $C_1$-$C_5$ alkyl, or $C_1$-$C_5$ trifluoroalkyl;
R₉ is (CH₂)ₚR₁, or $C_1$-$C_4$ alkyl;
R₁₀ is H or $C_1$-$C_3$ alkyl;
R₁₁ is H, $C_1$-$C_4$ alkyl, halo, or —(CH₂)ᵣ phenyl;
R₁₂ is H, —(CH₂)ₚR₁, $C_1$-$C_7$ alkyl, $C_1$-$C_7$ trifluoroalkyl, halo, substituted or unsubstituted phenyl, 3-pyridyl, 2-pyrimidyl, furanyl, oxazolyl, isoxazolyl, a substituted or unsubstituted fused bicyclic, a substituted or unsubstituted fused tricyclic, or when m is 0, 4,4-ethylenedioxy;
R₁₃ is O or S;
R₁₄ is H or CH₃;
R₁₅ is H or —(CH₂)qR₁₆;
R₁₆ is OH, NH₂, or CO₂H;
R₁₇ is H, OH, $C_1$-$C_4$ alkoxy, CO₂H, SO₃H, PO₃H₂, CONHSO₂R₈, or tetrazolyl;
Y is a R group of a naturally occurring amino acid;
X' is —O—, —(CH₂)ₚ—, or —S—;
m is independently 0 or 1;
n is independently 1, 2 or 3;
p is independently 0, 1, 2, 3 or 4;
q is 1, 2, 3, or 4;
r is independently 0, 1, 2, or 3;
providing when R₆ is (1) or (m), and R₁₂ is not H, the carboxy of (m) or the tetrazolyl of (1) is in position 2; and when R₆ is (1) or (m), m is 0, and R₁₂ is H, the carboxy of (m) or the tetrazolyl of (1) is in position 2 or 3.

U.S. Pat. No. 3,590,047 discloses compounds of the following formula that have anti-inflammatory, anti-pyretic and analgesic activity:

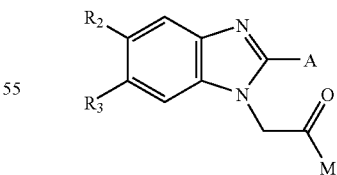

wherein A is a substituted or unsubstituted aralkyl, heteroaralkyl, aroyl or heteroaroyl radical or a benz derivative thereof;
R₂ is hydrogen, hydroxy, lower alkyl, lower alkoxy, nitro, amino, lower alkylamino, di(lower alkyl) amino, lower alkanoylamino, lower alkanoyl, bis(hydroxy lower alkyl) amino, 1-pyrrilidino, 4-methyl-1-piperazinyl, 4-morpholinyl, cyano, trifluoromethyl, halogen, di(lower alkyl) sulfamyl, benzylthio, amino lower alkyl, trifluoromethylthio, benzyloxy, lower alkenyl, lower alkenyloxy, 1-azacyclopropyl, cyclopropyl, cyclopropyl (lower alkoxy), and cyclobutyl (lower alkoxy); the lower alkenyl and alkyl groups containing up to six carbon atoms;

$R_3$ is hydrogen, halogen, trifluoromethyl, a lower alkyl radical, or a lower alkoxy radical;

M is $R_4$ or $R_5$, $R_4$ being amino (provided A is not benzyl at the same time), methylamino, ethylamino, propylamino, butylamino, dimethylamino, diethylamino, methylethylamino, methylbutylamino, dibutylamino, glucosamino, glycosylamino, allylamino, phenethylamino, N-ethylphenethylamino, β-hydroxyethylamino, 1-ethyl-2-aminoethylpiperidino, tetrahydrofurfurylamino, 1,2,5,6-tetrahydropyridino, morpholino, N-methylpiperazino, piperazino, N-phenylpiperazino, piperidino, benzylamino, anilino, cyclohexylamino, pyrrolidino, N-hydroxyethylpiperazino, sodium β-sulfoethylamino, N,N-dimethylcarboxamidomethylamino, N,N-diethylaminoethylamino, p-methoxyanilino, and 1-methyl-2-aminoethylpyrrolidino, $R_5$ being hydroxyl or a hydrocarbonoxy group, polyhydroxy lower alkyl, polyhydroxycycloalkyl, polyalkoxy lower alkyl, or a cyclic lower alkylamino lower alkyl radical derived from N-(β-hydroxyethyl) piperidine, N-(β-hydroxyethyl) pyrrolidine, N-(β-hydroxyethyl) morpholine, N-methyl-2-hydroxymethyl pyrrolidine, N-methyl-2-hydroxymethyl piperidine, N-ethyl-3-hydroxy piperidine, 3-hydroxyquinuclidine, and N-(β-hydroxyethyl)-N-methyl piperazine.

WO 02/060438 discloses compounds of the following formula that can be used as integrin antagonists:

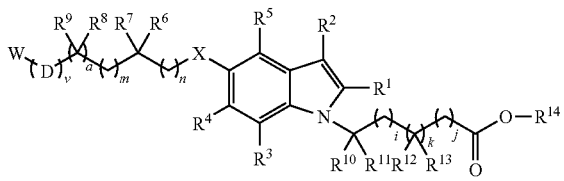

wherein $R^1$, $R^2$, $R^3$, $R^4$, and $R^5$ independently represent hydrogen, halogen, alkyl, aryl, aralkyl, heteroaryl, or heteroarylalkyl;

$R^6$, $R^7$, $R^8$, and $R^9$ independently represent hydrogen, alkyl, hydroxyalkyl, aminoalkyl, monoalkylaminoalkyl, dialkylaminoalkyl, carboxyalkyl, aryl, or aralkyl;

or $R^6$ and $R^7$ are taken together to form —(CH$_2$)$_p$—, where p is 2-8, while $R^8$ and $R^9$ are defined as above; or $R^8$ and $R^9$ are taken together to form —(CH$_2$)$_q$—, where q is 2-8, while $R^6$ and $R^7$ are defined as above; or $R^6$ and $R^8$ are taken together to form —(CH$_2$)$_r$—, while r is zero (a bond), 1, or 2, while $R^7$ and $R^9$ are defined as above;

X represents oxygen, sulfur, —CH$_2$—, —NH—, —(C=O)NH—, or —NH(C=O)—;

n is from 0 to 4;
m is from 0 to 4;
a is 0 or 1;
D represents oxygen;
V is 0 or 1;

$R^{10}$, $R^{11}$, $R^{12}$, and $R^{13}$ independently represent: hydrogen; hydroxy; alkyl; alkoxy; cycloalkyl; aryl, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; monoalkylamino; dialkylamino; aminoalkyl; monoalkylaminoalkyl; dialkylaminoalkyl; alkanoyl; heteroaryl having 5-14 ring members, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; or

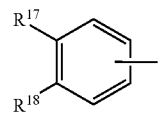

wherein $R^{17}$ and $R^{18}$ together form —CH$_2$CH$_2$—O—, —O—CH$_2$CH$_2$—, —O—CH$_2$—O—, or —O—CH$_2$CH$_2$—O—; or $R^{10}$ and $R^{12}$ are taken together to form —(CH$_2$)$_s$—, wherein s is 0 (a bond) or 1 to 4, while $R^{11}$ and $R^{13}$ are defined as above; or $R^{10}$ and $R^{12}$ are taken together to form a double bond when i is 0 and k is 1, while $R^{11}$ and $R^{13}$ are as defined above; or $R^{10}$ and $R^{11}$ are taken together to form —(CH$_2$)$_t$—, wherein t is 2 to 8, while $R^{12}$ and $R^{13}$ are defined as above, or $R^{12}$ and $R^{13}$ are taken together to form —(CH$_2$)$_u$— wherein u is 2 to 8, while $R^{10}$ and $R^{11}$ are defined as above;

i is from 0 to 4;
j is from 0 to 4;
k is 0 or 1;
$R^{14}$ is hydrogen or a functionality that acts as a prodrug;
W is

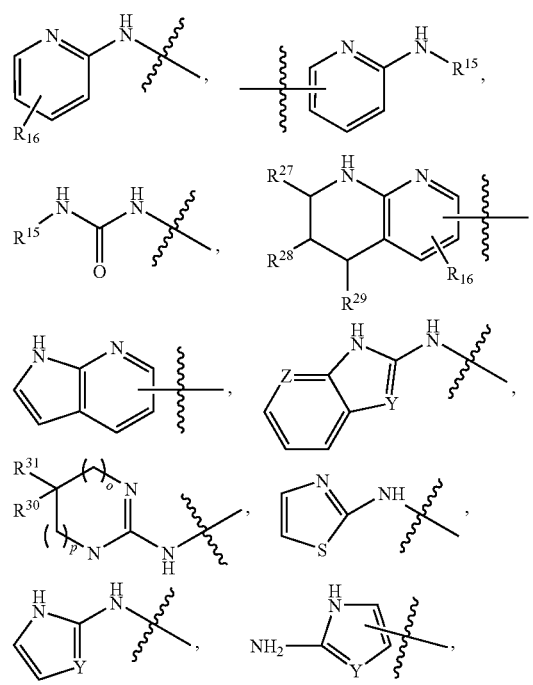

-continued

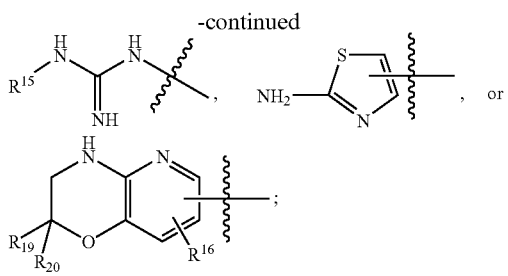

wherein Y is —N— or —CH—;
Z is —N— or —CH—;
$R^{15}$ is hydrogen, halogen, alkyl, aryl, or arylalkyl;
$R^{16}$ is hydrogen, alkyl, haloalkyl, or halogen;
$R^{19}$ and $R^{20}$ are independently hydrogen, halogen, or alkyl;
$R^{27}$, $R^{28}$, $R^{29}$, $R^{30}$, and $R^{31}$ are independently hydrogen, halogen, alkyl, alkoxy or aryl; and
o and p are independently 0, 1, or 2.

SUMMARY OF THE INVENTION

The present invention relates to benzimidazole acetic acid compounds that are useful for inhibiting binding of endogenous ligands to the CRTH2 receptor. In particular, the compounds of the present invention are antagonists of the human CRTH2 receptor (hCRTH2). In one embodiment, the benzimidazole acetic acids are compounds of Formula I:

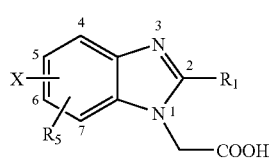

(I)

and pharmaceutically acceptable salts and prodrugs thereof, wherein:
X is $NR_2SO_2R_3$, $NR_2COR_4$, $S(O)_nR_4$ or H;
n is 0, 1, or 2;
$R_1$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, or —$C_{1-10}$ alkyl-O—$C_{1-10}$ alkyl;
$R_2$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, or heteroaryl;
$R_3$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, or $OR_2$;
$R_4$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, $OR_2$ or $NR_2R_2$; or
$R_2$ and $R_3$ form a ring; or
$R_2$ and $R_4$ form a ring; and
$R_5$ is H, halogen, or substituted or unsubstituted $C_{1-10}$ alkyl, $C_{1-10}$ perhalo alkyl (preferably $CF_3$), $C_{2-10}$ alkenyl, $C_{2-10}$ alkynyl, or $OR_2$; or
$R_5$ together with $R_2$, $R_3$, or $R_4$ forms a fused saturated or unsaturated ring.

In certain embodiments the compounds of Formula I exclude compounds in which $R_4$ is aryl when X is $NR_2COR_4$ in the 4 position.

The invention relates to compounds represented by Formula I, which are antagonists or inverse agonists of CRTH2. The invention relates to the use of the compounds of the invention to inhibit binding of endogenous ligands, including $PGD_2$ and its metabolites and certain thromboxane metabolites, to CRTH2. The compounds are useful for the treatment, amelioration, or prevention of disorders responsive to inhibition of binding to CRTH2, e.g., disorders characterized by elevated levels of $PGD_2$ or its metabolites or certain thromboxane metabolites. These disorders include, but are not limited to, respiratory tract disorders (e.g., asthma, chronic obstructive pulmonary disease, rhinitis), bone and joint disorders (e.g., arthritis, Sjogren's syndrome), skin and eye disorders (e.g., psoriasis, dermatitis, uveitis, conjunctivitis), gastrointestinal tract disorders (e.g., colitis, celiac disease, Crohn's disease), central and peripheral nervous system disorders (e.g., Alzheimer's disease, multiple sclerosis, migraine, stroke), disorders of other tissues and systemic disorders (e.g., atherosclerosis, AIDS, sepsis, ischemic/reperfusion injury, hepatitis) and allograft rejection.

The present invention provides methods of blocking/antagonizing the CRTH2 receptor on a cell, comprising contacting the cell with a compound of Formula I. The present invention also provides methods of treating, ameliorating, or preventing a disorder responsive to blocking/antagonizing the CRTH-2 receptor in an animal, comprising administering to said animal a therapeutically effective amount of a compound of Formula I.

The present invention provides pharmaceutical compositions comprising a compound of Formula I in a therapeutically effective amount to inhibit binding of ligands to the CRTH2 receptor. The compositions may further comprise other therapeutic agents.

The invention further provides kits comprising a compound of Formula I and instructions for administering the compound to an animal. The kits may optionally contain other therapeutic agents.

The invention also provides methods of making compounds of Formula I.

DETAILED DESCRIPTION OF THE INVENTION

The present invention relates to compounds represented by Formula I, which are antagonists or inverse agonists of the CRTH2 receptor and function as inhibitors of the binding of endogenous ligands to the CRTH2 receptor. By inhibiting the binding of endogenous ligands such as $PGD_2$ and its metabolites, these compounds at least partially inhibit the effects of the endogenous ligands in an animal. Therefore, the invention relates to methods of inhibiting the binding of endogenous ligands to the CRTH2 receptor on a cell, comprising contacting the cell with a compound of Formula I. The invention further relates to methods of treating, ameliorating, or preventing disorders in an animal that are responsive to inhibition of the CRTH2 receptor comprising administering to the animal a compound of Formula I. Such disorders include those characterized by elevated levels of $PGD_2$ or its metabolites or certain thromboxane metabolites.

The term "CRTH2 receptor," as used herein, refers to any known member of the CRTH2 receptor family, including, but not limited to, hCRTH2.

The term "elevated levels of $PGD_2$ or its metabolites or certain thromboxane metabolites," as used herein, refers to an elevated level (e.g., aberrant level) of these molecules in cells as compared to similar corresponding non-pathological cells expressing basal levels of $PGD_2$ or its metabolites or thromboxanes and metabolites.

The term "other therapeutic agents," as used herein, refers to any therapeutic agent that has been used, is currently used, or is known to be useful for treating, ameliorating, or preventing a disorder encompassed by the present invention. For example, agents used to treat asthma and rhinitis include steroids, β2-receptor agonists and leukotriene receptor antagonists.

The term "prodrug," as used herein, refers to a pharmacologically inactive derivative of a parent "drug" molecule that requires biotransformation (e.g., either spontaneous or enzymatic) within the target physiological system to release or convert the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of asthma, a therapeutically effective amount preferably refers to the amount of a therapeutic agent that increases peak air flow by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "prevent," "preventing," and "prevention," as used herein, refer to a decrease in the occurrence of pathological cells (e.g., autoimmune T cells) or a pathological condition (e.g., constricted airways) in an animal. The prevention may be complete, e.g., the total absence of pathological cells or a pathological condition in an animal. The prevention may also be partial, such that the occurrence of pathological cells or a pathological condition in an animal is less than that which would have occurred without the present invention.

The compounds of the present invention are compounds having Formula I:

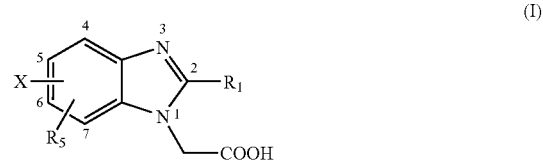

(I)

and pharmaceutically acceptable salts and prodrugs thereof, wherein:

X is $NR_2SO_2R_3$, $NR_2COR_4$, $S(O)_nR_4$ or H;

n is 0, 1, or 2;

$R_1$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, or —$C_{1-10}$ alkyl-O—$C_{1-10}$ alkyl;

$R_2$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, or heteroaryl;

$R_3$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, or $OR_2$;

R$_4$ is H or substituted or unsubstituted C$_{1-10}$ alkyl, C$_{1-10}$ perhalo alkyl (preferably CF$_3$), C$_{2-10}$ alkenyl, C$_{2-10}$ alkynyl, —C$_{1-10}$ alkyl-O—C$_{1-10}$ alkyl, —C$_{3-10}$ cycloalkyl, —C$_{1-10}$ alkyl-C$_{3-10}$ cycloalkyl, —C$_{1-10}$ alkyl-O-aryl, —C$_{1-10}$ alkyl-O-heteroaryl, C$_{1-10}$ alkylaryl, C$_{1-10}$ alkylheteroaryl, aryl, heteroaryl, OR$_2$ or NR$_2$R$_2$; or R$_2$ and R$_3$ form a ring; or R$_2$ and R$_4$ form a ring; and R$_5$ is H, halogen, or substituted or unsubstituted C$_{1-10}$ alkyl, C$_{1-10}$ perhalo alkyl (preferably CF$_3$), C$_{2-10}$ alkenyl, C$_{2-10}$ alkynyl, or OR$_2$; or R$_5$ together with R$_2$, R$_3$, or R$_4$ forms a fused saturated or unsaturated ring.

In certain embodiments the compounds of Formula I exclude compounds in which R$_4$ is aryl when X is NR$_2$COR$_4$ in the 4 position.

In particular embodiments, the compounds of the present invention are compounds having Formula I wherein X is NR$_2$SO$_2$R$_3$; and R$_1$, R$_2$, R$_3$, and R$_5$ are as defined above.

In other particular embodiments, the compounds of the present invention are compounds having Formula I wherein X is NR$_2$COR$_4$; and R$_1$, R$_2$, R$_4$, and R$_5$ are as defined above.

Useful alkyl groups include straight-chained or branched C$_{1-10}$ alkyl groups, especially methyl, ethyl, propyl, isopropyl, t-butyl, sec-butyl, 3-pentyl, adamantyl, norbornyl, and 3-hexyl groups. Lower alkyl groups are C$_{1-6}$ alkyl groups.

Useful alkenyl groups include straight-chained or branched C$_{2-10}$ alkenyl groups, especially ethenyl, propenyl, isopropenyl, butenyl, isobutenyl, and hexenyl.

Useful alkynyl groups include straight-chained or branched C$_{2-10}$ alkynyl groups, especially ethynyl, propynyl, butynyl, isobutynyl, and hexynyl.

Useful cycloalkyl groups are C$_{3-10}$ cycloalkyl or partially saturated cycloalkyl. Typical cycloalkyl groups include cyclopropyl, cyclobutyl, cyclopentyl, cyclohexyl, cycloheptyl, cyclopentenyl, cycloheptenyl, and cyclooctenyl.

Useful aryl groups include C$_{6-14}$ aryl, especially phenyl, naphthyl, phenanthrenyl, anthracenyl, indenyl, azulenyl, biphenyl, biphenylenyl, and fluorenyl groups.

Useful heteroaryl groups include thiazolyl, oxazolyl, thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Useful saturated or partially saturated heterocyclic groups include tetrahydrofuiranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Optional substituents include one or more alkyl; halo; haloalkyl; cycloalkyl; aryl optionally substituted with one or more lower alkyl, halo, haloalkyl or heteroaryl groups; aryloxy optionally substituted with one or more lower alkyl, haloalkyl, or heteroaryl groups; aralkyl, heteroaryl optionally substituted with one or more lower alkyl, haloalkyl, and aryl groups; heteroaryloxy optionally substituted with one or more lower alkyl, haloalkyl, and aryl groups; alkoxy; haloalkoxy; alkoxycarbonyl; alkylcarbamate; alkylthio; arylthio; amino; cyano; acyloxy; arylacyloxy optionally substituted with one or more lower alkyl, haloalkyl, and aryl groups; diphenylphosphinyloxy optionally substituted with one or more lower alkyl, halo or haloalkyl groups; heterocyclo optionally substituted with one or more lower alkyl, haloalkyl, and aryl groups; heterocycloalkoxy optionally substituted with one or more lower alkyl, haloalkyl, and aryl groups; partially unsaturated heterocycloalkyl optionally substituted with one or more lower alkyl, haloalkyl, and aryl groups; or partially unsaturated heterocycloalkyloxy optionally substituted with one or more lower alkyl, haloalkyl, and aryl groups.

Useful halo or halogen groups include fluorine, chlorine, bromine and iodine.

Useful arylalkyl groups or heteroarylalkyl groups include any of the above-mentioned C$_{1-10}$ alkyl groups substituted by any of the above-mentioned C$_{6-14}$ aryl groups or heteroaryl groups. Useful values include benzyl, phenethyl and naphthylmethyl.

The term "ring," as used herein in the phrases "R$_2$ and R$_3$ form a ring," "R$_2$ and R$_4$ form a ring," and "R$_5$ together with R$_2$, R$_3$, or R$_4$ forms a fused saturated or unsaturated ring," refers to an optionally substituted heterocyclic or heteroaryl ring or optionally substituted fused heterocyclic or heteroaryl ring. The heterocyclic or heteroaryl ring may be fused to any optionally substituted aryl, heteroaryl, cycloalkyl, or heterocyclic group such as those listed above.

Certain of the compounds of the present invention may exist as stereoisomers including optical isomers. The invention includes all stereoisomers and both the racemic mixtures of such stereoisomers as well as the individual enantiomers that may be separated according to methods that are well known to those of skill in the art.

The compounds of this invention may be prepared using methods known to those of skill in the art. In one embodiment, the compounds may be prepared by the following general synthetic schemes 1-3.

Scheme 1:

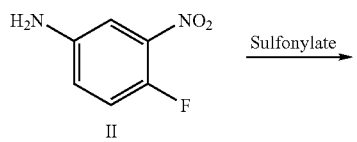

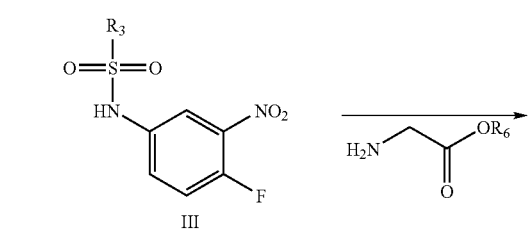

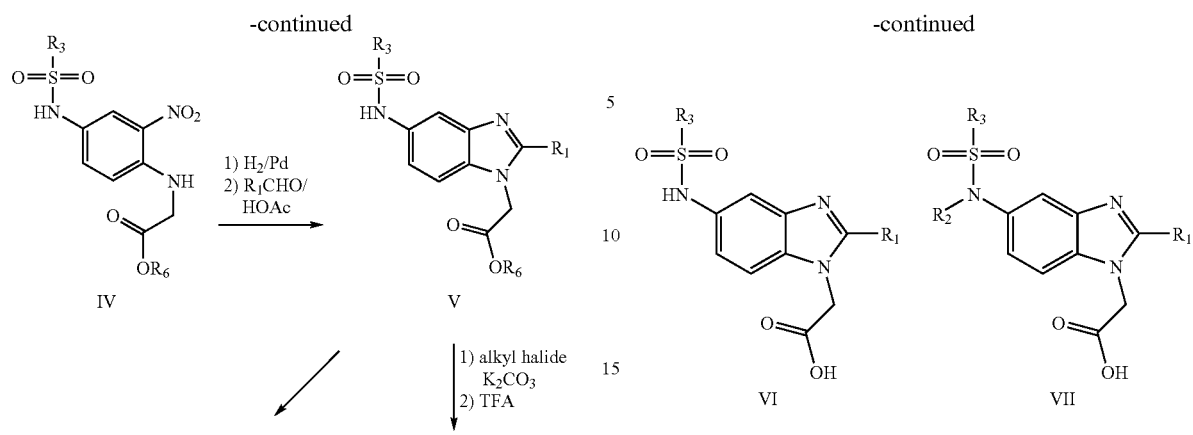
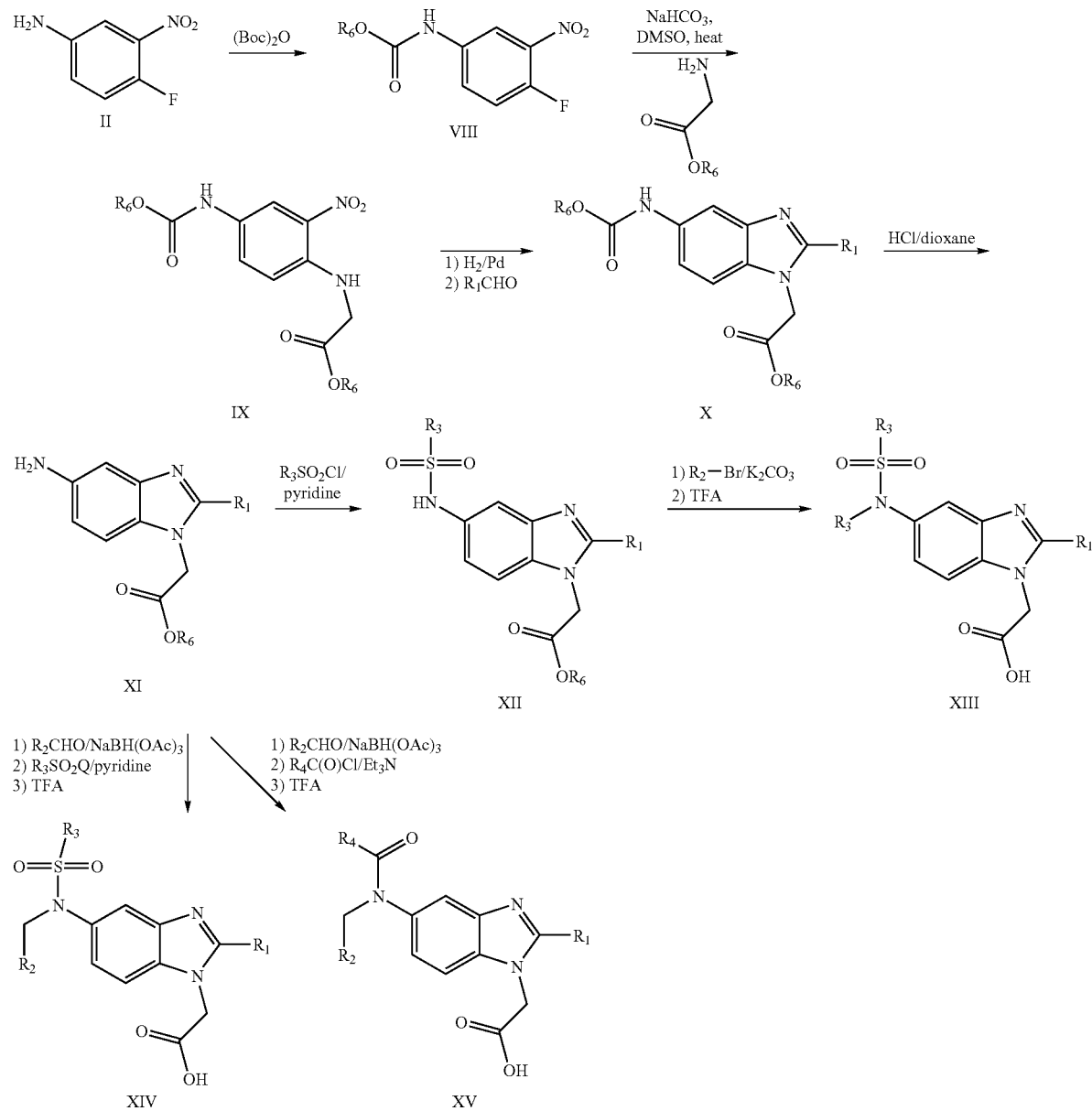

Scheme 3:
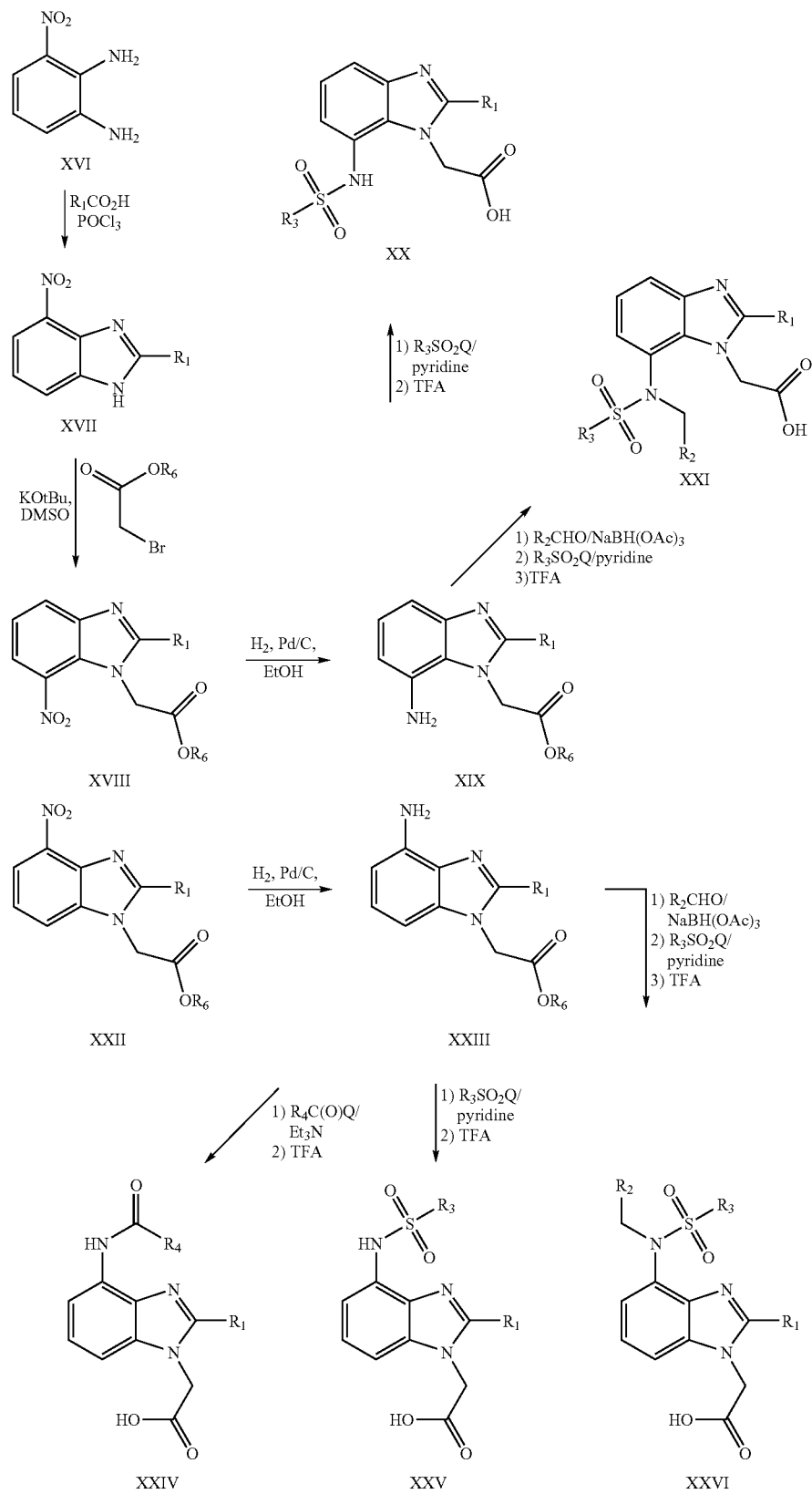

wherein R₆ is a carboxyl protecting group (e.g., alkyl, preferably t-butyl).

In one embodiment, the invention relates to a method of preparing a compound having formula VI or VII, comprising a) condensing a compound having Formula II with a sulfonylate (e.g., R₃SO₂Q, wherein Q is halo, e.g., chloro) in a polar solvent (e.g., dichloromethane (DCM)) at ambient temperature, to form a compound having Formula III, which is than isolated (e.g., extracted and recrystallized);

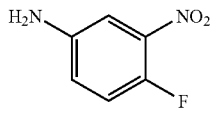

II

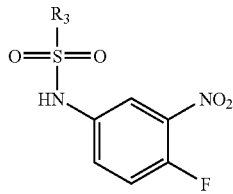

III b) condensing a compound having Formula III with a carboxyl-protected amino acid (e.g., NH₂CH₂C(O)OR₆) in a polar solvent (e.g., dimethylsulfoxide) in the presence of a base (e.g., NaHCO₃) at an elevated temperature (e.g., about 65° C.), to form a compound having Formula IV, which may then be isolated (e.g., extracted and concentrated);

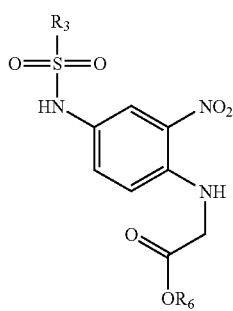

IV c) reducing a compound having Formula IV in a solvent (e.g., an alcohol solvent such as ethanol) with a hydrogen catalyst (e.g., 3% Pd/C under H₂) followed by alkylation with an aldehyde R₁CHO in a solvent (e.g., an alcohol solvent such as ethanol) in the presence of an acid (e.g., acetic acid) at an elevated temperature (e.g., about 70° C.), to form a compound having Formula V, which may then be isolated (e.g., concentrated under reduced pressure); and

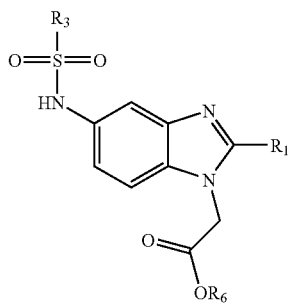

V d) deprotecting a compound having Formula V by adding an acid (e.g., trifluoroacetic acid) at ambient temperature to form a compound having Formula VI, which may then be isolated (e.g., concentrated and purified by preparative liquid chromatography/mass spectrometry);

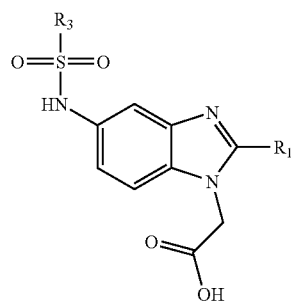

VI or e) alkylating a compound having Formula V, e.g., with an alkyl halide (e.g., benzyl bromide) in a solvent (e.g., dimethylformamide) in the presence of a base (e.g., K₂CO₃) at ambient temperature, and then deprotecting by adding an acid (e.g., trifluoroacetic acid) at ambient temperature, to form a compound having Formula VII, which may then be isolated (e.g., concentrated and purified by preparative liquid chromatography/mass spectrometry);

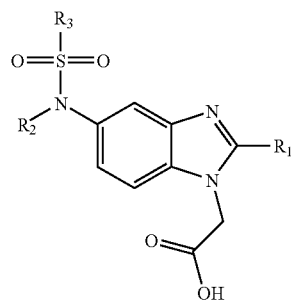

VII wherein $R_1$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, or —$C_{1-10}$ alkyl-O—$C_{1-10}$ alkyl₂;

$R_2$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, or heteroaryl;

$R_3$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, or $OR_2$;

Q is a halogen; and $R_6$ is a carboxyl protecting group (e.g., alkyl, preferably t-butyl).

In one embodiment, the invention relates to a method of preparing a compound having formula VI or VII, comprising a) deprotecting a compound having Formula V to form a compound having Formula VI;

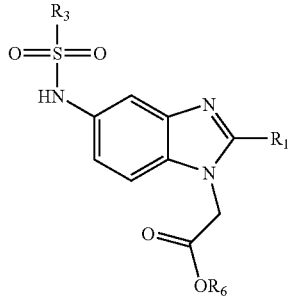
V

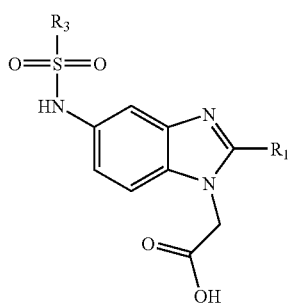
VI or
b) alkylating a compound having Formula V and then deprotecting to form a compound having Formula VII.

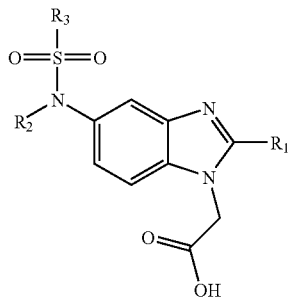
VII

In one embodiment, the invention relates to a method of preparing a compound having formula XIII, XIV, or XV, comprising
a) protecting a compound having Formula II with an amino protecting group (e.g., with (Boc)$_2$O) to form a compound having Formula VIII;

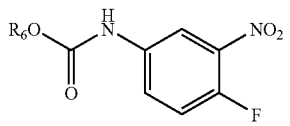
VIII b) condensing a compound having Formula VIII with a protected amino acid (e.g., NH$_2$CH$_2$C(O)OR$_6$) in a polar solvent (e.g., dimethylsulfoxide) in the presence of a base (e.g., NaHCO$_3$), at an elevated temperature (e.g., about 65° C.), to form a compound having Formula IX;

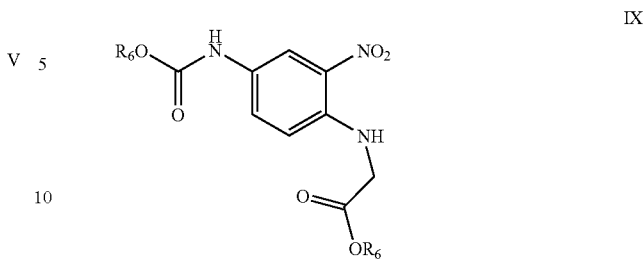
IX c) reducing a compound having Formula IX, e.g., in a solvent (e.g., an alcohol solvent such as ethanol) with a hydrogen catalyst (e.g., 3% Pd/C under H$_2$) followed by alkylation with an aldehyde R$_1$CHO, in a solvent (e.g., an alcohol solvent such as ethanol) at an elevated temperature (e.g., about 70° C.), to form a compound having Formula X, which may then be isolated (e.g., concentrated under reduced pressure and used without further purification);

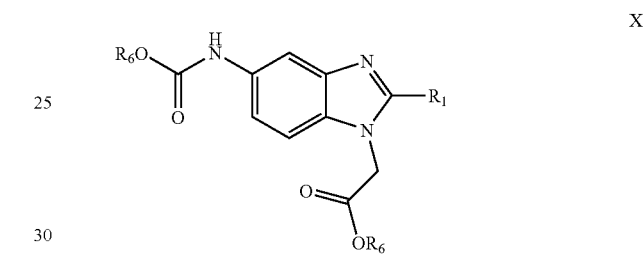
X d) deprotecting a compound having Formula X in a solvent (e.g., dioxane) in the presence of an acid (e.g., HCl) at ambient temperature to form a compound having Formula XI;

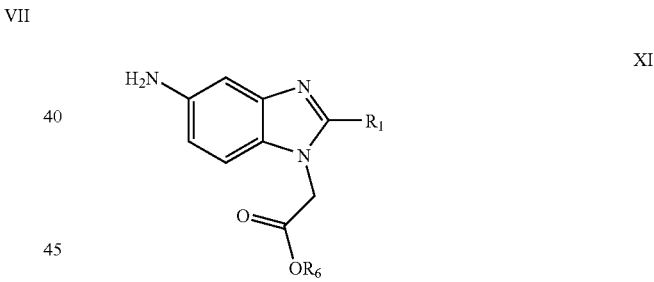
XI e) condensing a compound having Formula XI with a sulfonylate (e.g., R$_3$SO$_2$Q) in a non-polar solvent (e.g., pyridine) at ambient temperature to form a compound having Formula XII; and

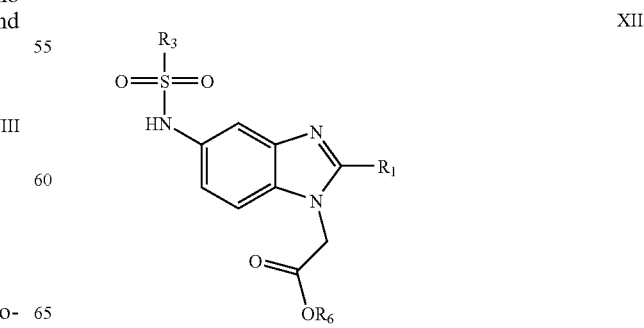
XII f) alkylating a compound having Formula XII with an alkyl halide in a solvent in the presence of a base (e.g., $K_2CO_3$) at ambient temperature followed by elevated temperature (e.g., about 50° C.), and then deprotecting by adding an acid (e.g., trifluoroacetic acid) at ambient temperature, to form a compound having Formula XIII, which may then be isolated (e.g., concentrated and purified by preparative liquid chromatography/mass spectrometry);

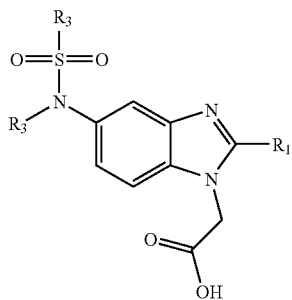

XIII or g) alkylating a compound having Formula XI, with an aldehyde $R_2CHO$ in a solvent in the presence of a reducing agent (e.g., $NaBH(OAc)_3$) at ambient temperature followed by elevated temperature (e.g., about 50° C.), condensing with a sulfonylate (e.g., $R_3SO_2Q$) in a solvent (e.g., pyridine) at ambient temperature, and then deprotecting by adding an acid (e.g., trifluoroacetic acid) at ambient temperature to form a compound having Formula XIV, which may then be isolated (e.g., concentrated and purified by preparative liquid chromatography/mass spectrometry);

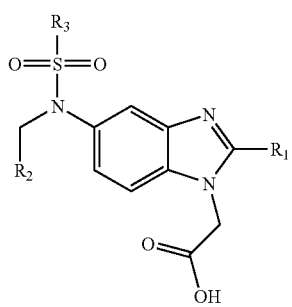

XIV or h) alkylating a compound having Formula XI with an aldehyde $R_2CHO$ in a solvent in the presence of a reducing agent (e.g., $NaBH(OAc)_3$) at ambient temperature followed by elevated temperature (e.g., about 50° C.), followed by condensing with an acyl halide (e.g., $R_4C(O)Q$) in a non-polar solvent (e.g., triethylamine) at ambient temperature, and then deprotecting by adding an acid (e.g., trifluoroacetic acid) at ambient temperature to form a compound having Formula XV, which may then be isolated (e.g., concentrated and purified by preparative liquid chromatography/mass spectrometry);

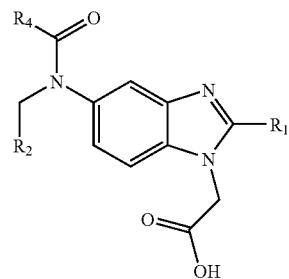

XV wherein $R_1$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, or —$C_{1-10}$ alkyl-O—$C_{1-10}$ alkyl;

$R_2$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, or heteroaryl;

$R_3$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, or $OR_2$;

$R_4$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, $OR_2$ or $NR_2R_2$;

Q is a halogen; and $R_6$ is a carboxyl protecting group (e.g., alkyl, preferably t-butyl).

In one embodiment, the invention relates to a method of preparing a compound having formula XIII, XIV, or XV, comprising a) alkylating a compound having Formula XII with an alkyl halide and then deprotecting to form a compound having Formula XIII;

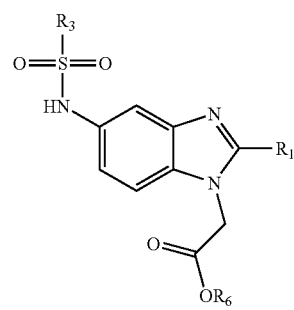

XII

-continued

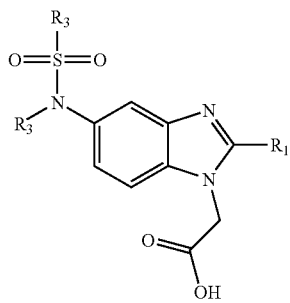
XIII or b) alkylating a compound having Formula XI, with an aldehyde R₂CHO, condensing with a sulfonylate, and then deprotecting to form a compound having Formula XIV;

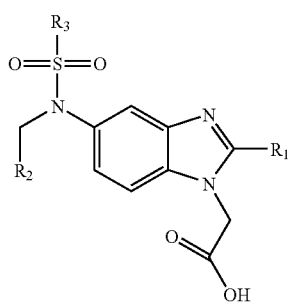
XIV or c) alkylating a compound having Formula XI with an aldehyde R₂CHO, followed by condensing with an acyl halide, and then deprotecting to form a compound having Formula XV.

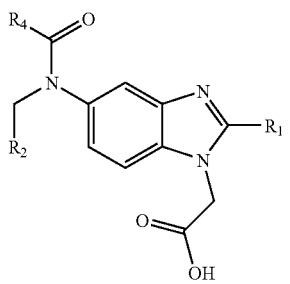
XV

In one embodiment, the invention relates to a method of preparing a compound having formula XX or XXI, comprising a) condensing a compound having Formula XVI with a carboxylic acid $R_1CO_2H$ in the presence of a condensation reagent (e.g., $POCl_3$) to form a compound having Formula XVII;

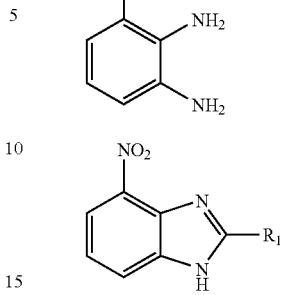
XVI

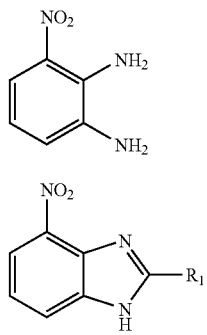
XVII b) condensing a compound having Formula XVII with a halogenated acetic acid alkyl ester in a polar solvent (e.g., dimethylsulfoxide) at an elevated temperature (e.g., about 50-80° C.), to form a compound having Formula XVIII;

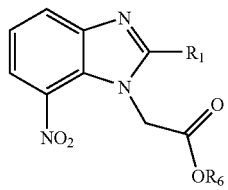
XVIII c) reducing a compound having Formula XVIII in a solvent (e.g., an alcohol solvent such as ethanol) with a hydrogen catalyst (e.g., 3% Pd/C under $H_2$) to form a compound having Formula XIX;

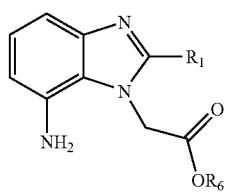
XIX d) condensing a compound having Formula XIX with a sulfonylate (e.g., $R_3SO_2Q$) in a solvent (e.g., pyridine) at ambient temperature, and then deprotecting by adding an acid (e.g., trifluoroacetic acid) at ambient temperature to form a compound having Formula XX, which may then be isolated (e.g., concentrated and purified by preparative liquid chromatography/mass spectrometry);

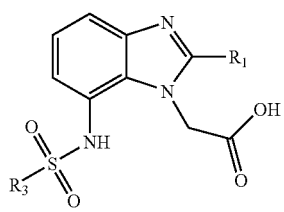
XX or e) alkylating a compound having Formula XIX with an aldehyde R₂CHO in a solvent in the presence of a reducing agent (e.g., NaBH(OAc)₃) at ambient temperature followed by elevated temperature (e.g., about 50° C.), condensing with a sulfonylate (e.g., R₃SO₂Q) in a solvent (e.g., pyridine) at ambient temperature, and then deprotecting by adding an acid (e.g., trifluoroacetic acid), at ambient temperature to form a compound having Formula XXI, which may then be isolated (e.g., concentrated and purified by preparative liquid chromatography/mass spectrometry);

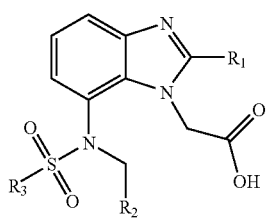

XXI wherein

R₁ is H or substituted or unsubstituted $C_{1-10}$ alkyl, $C_{1-10}$ perhalo alkyl (preferably CF₃), $C_{2-10}$ alkenyl, $C_{2-10}$ alkynyl, or —$C_{1-10}$ alkyl-O—$C_{1-10}$ alkyl;

R₂ is H or substituted or unsubstituted $C_{1-10}$ alkyl, $C_{1-10}$ perhalo alkyl (preferably CF₃), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, or heteroaryl;

R₃ is H or substituted or unsubstituted $C_{1-10}$ alkyl, $C_{1-10}$ perhalo alkyl (preferably CF₃), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, or OR₂;

Q is a halogen; and

R₆ is a carboxyl protecting group (e.g., alkyl, preferably t-butyl).

In one embodiment, the invention relates to a method of preparing a compound having formula XX or XXI, comprising a) condensing a compound having Formula XIX with a sulfonylate and then deprotecting to form a compound having Formula XX;

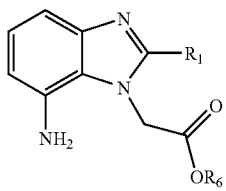

XIX

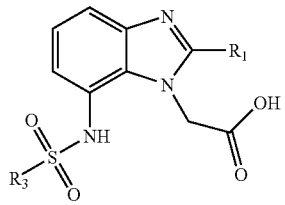

XX or b) alkylating a compound having Formula XIX with an aldehyde R₂CHO, condensing with a sulfonylate, and then deprotecting to form a compound having Formula XXI.

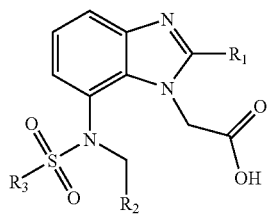

XXI

In one embodiment, the invention relates to a method of preparing a compound having formula XXIV, XXV, or XXVI, comprising a) condensing a compound having Formula XVI with a carboxylic acid R₁CO₂H in the presence of a condensation reagent (e.g., POCl₃), to form a compound having Formula XVII;

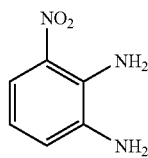

XVI

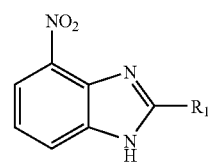

XVII b) alkylating a compound having Formula XVII with a halogenated acetic acid alkyl ester in a polar solvent (e.g., dimethylsulfoxide) at an elevated temperature (e.g., about 65° C.) to form a compound having Formula XXII;

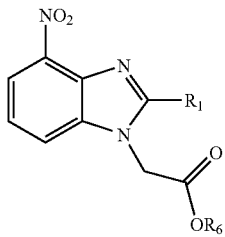

XXII c) reducing a compound having Formula XXII in a solvent (e.g., an alcohol solvent such as ethanol) with a hydrogen catalyst (e.g., 3% Pd/C under $H_2$) to form a compound having Formula XXIII;

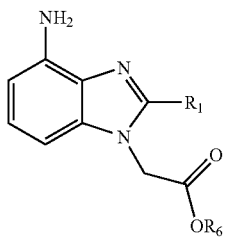

XXIII d) condensing a compound having Formula XXIII with an acyl halide (e.g., $R_4C(O)Cl$) in a non-polar solvent (e.g., triethylamine) at ambient temperature, and then deprotecting by adding an acid (e.g., trifluoroacetic acid) at ambient temperature to form a compound having Formula XXIV, which may then be isolated (e.g., concentrated and purified by preparative liquid chromatography/mass spectrometry);

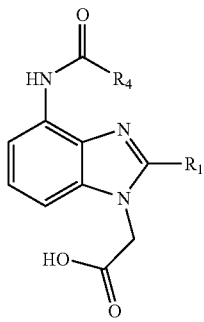

XXIV or e) condensing a compound having Formula XXIII with a sulfonylate (e.g., $R_3SO_2Q$) in a solvent (e.g., pyridine) at ambient temperature, and then deprotecting by adding an acid (e.g., trifluoroacetic acid) at ambient temperature, to form a compound having Formula XXV, which may then be isolated (e.g., concentrated and purified by preparative liquid chromatography/mass spectrometry);

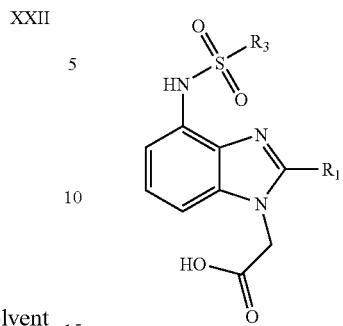

XXV or f) alkylating a compound having Formula XXIII with an aldehyde $R_2CHO$ in a solvent in the presence of a reducing agent (e.g., $NaBH(OAc)_3$) at ambient temperature followed by elevated temperature (e.g., about 50° C.), condensing with a sulfonylate (e.g., $R_3SO_2Q$) in a solvent (e.g., pyridine) at ambient temperature, and then deprotecting by adding an acid (e.g., trifluoroacetic acid) at ambient temperature, to form a compound having Formula XXVI, which may then be isolated (e.g., concentrated and purified by preparative liquid chromatography/mass spectrometry);

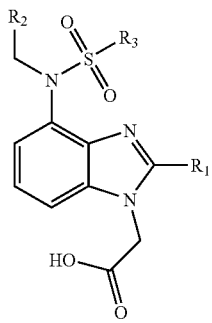

XXVI wherein $R_1$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, or —$C_{1-10}$ alkyl-O—$C_{1-10}$ alkyl;

$R_2$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, or heteroaryl;

$R_3$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, or $OR_2$;

$R_4$ is H or substituted or unsubstituted $C_{1-10}$ alkyl, $C_{1-10}$ perhalo alkyl (preferably $CF_3$), $C_{2-10}$ alkenyl, $C_{2-10}$ alkynyl, —$C_{1-10}$ alkyl-O—$C_{1-10}$ alkyl, —$C_{3-10}$ cycloalkyl, —$C_{1-10}$ alkyl-$C_{3-10}$ cycloalkyl, —$C_{1-10}$ alkyl-O-aryl, —$C_{1-10}$ alkyl-O-heteroaryl, $C_{1-10}$ alkylaryl, $C_{1-10}$ alkylheteroaryl, aryl, heteroaryl, $OR_2$ or $NR_2R_2$;

Q is a halogen; and $R_6$ is a carboxyl protecting group (e.g., alkyl, preferably t-butyl).

In one embodiment, the invention relates to a method of preparing a compound having formula XXIV, XXV, or XXVI, comprising a) condensing a compound having Formula XXIII with an acyl halide and then deprotecting to form a compound having Formula XXIV;

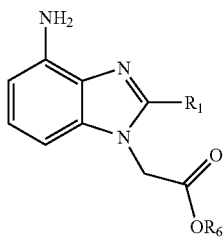

XXIII

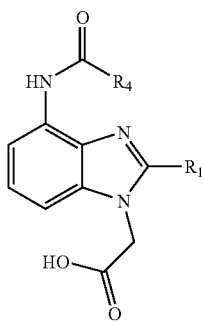

XXIV or b) condensing a compound having Formula XXIII with a sulfonylate and then deprotecting to form a compound having Formula XXV;

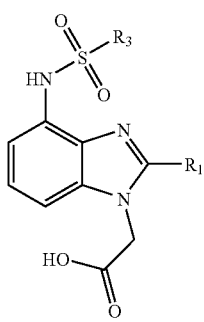

XXV or c) alkylating a compound having Formula XXIII with an aldehyde $R_2CHO$, condensing with a sulfonylate, and then deprotecting to form a compound having Formula XXVI.

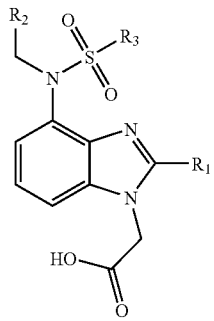

XXVI

An important aspect of the present invention is that compounds of Formula I inhibit the binding of $PGD_2$ and its metabolites to the CRTH2 receptor. Therefore, it is contemplated that these compounds inhibit the effects of $PGD_2$ or its metabolites on cells containing CRTH2 receptors. The inhibitors of the present invention can be used to block the effect of endogenous ligands of the CRTH2 receptor in any disorder that can be treated, ameliorated, or prevented by blocking the CRTH2 receptor. Thus, the present invention provides compositions and methods for targeting animals characterized as having elevated levels of $PGD_2$ or other endogenous ligands of the CRTH2 receptor. The present invention also contemplates methods of treating animals having normal levels of $PGD_2$ or other endogenous ligands of the CRTH2 receptor that would benefit from decreasing the effects of these molecules to sub-normal levels.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various disorders, diseases and pathologies are amenable to treatment or prophylaxis using the present methods and compositions. A non-limiting list of these diseases and conditions includes, but is not limited to, disorders of the respiratory tract, including asthma, chronic obstructive pulmonary disease, bronchitis, rhinitis, nasal polyposis, sarcoidosis, farmer's lung, fibroid lung, idiopathic interstitial pneumonia, cystic fibrosis, and cough; disorders of the bones and joints, including arthritis, ankylosing spondylitis, Reiter's disease, Behcet's disease, Sjorgren's syndrome, and systemic sclerosis; disorders of the skin and eyes, including psoriasis, dermatitis, atopic dermatitis, Lichen planus, pemphigus, epidermolysis bullosa, urticaria, angiodermas, vasculitides, erythemas, cutaneous eosinophilias, chronic skin ulcers, uveitis, corneal ulcers, and conjunctivitis; disorders of the gastrointestinal tract, including celiac disease, proctitis, gastroenteritis, mastocytosis, Crohn's disease, ulcerative colitis, irritable bowel disease, and food-related allergies; disorders of the central and peripheral nervous system, including Alzheimer's disease, amyotrophic lateral sclerosis, Creutzfeldt-Jacob's disease, AIDS dementia complex, Huntington's disease, Guillain-Barre syndrome, multiple sclerosis, encephalomyelitis, myasthenia gravis, tropical spastic paraparesis, CNS trauma, migraine, and stroke; disorders of other tissues and systemic disorders, including atherosclerosis, AIDS, lupus erythematosus, Hashimoto's thyroiditis, type I diabetes, nephrotic syndrome, eosinophilia fascitis, hyper IgE syndrome, leprosy, thrombocytopenia purpura, post-operative adhesions, sepsis, ischemic/reperfusion injury, hepatitis, glomerulonephritis, and chronic renal failure; and acute and chronic allograft rejection.

Some embodiments of the present invention provide methods for administering an effective amount of a compound of Formula I and at least one additional therapeutic agent. The additional therapeutic agent may be any therapeutic agent that has been used, is currently used, or is known to be useful for treating, ameliorating, or preventing a disorder encompassed by the present invention. For example, the additional therapeutic agent may be another compound that inhibits binding to the CRTH2 receptor (e.g., indomethacin). In another embodiment, the additional therapeutic drug is one that has a complementary effect to the compounds of the present invention. For a more detailed description of therapeutic agents, those skilled in the art are referred to instructive manuals including, but not limited to, the Physician's Desk Reference and to Goodman and Gilman's "Pharmaceutical Basis of Therapeutics" tenth edition, Eds. Hardman et al., 2002. The combination of a compound of the invention and one or more therapeutic agents may have additive potency or an additive therapeutic effect. The invention also encompasses synergistic combinations where the therapeutic efficacy is greater than additive. Preferably, such combinations also reduce or avoid unwanted or adverse effects. In certain embodiments, the combination therapies encompassed by the invention will provide an improved overall therapy relative to administration of a compound of Formula I or any therapeutic agent alone. In certain embodiments, doses of existing or experimental therapeutic agents will be reduced or administered less frequently which increases patient compliance, thereby improving therapy and reducing unwanted or adverse effects.

Examples of useful therapeutic agents include, but are not limited to, agents used to treat asthma and rhinitis (steroids (e.g., budesonide), β2-receptor agonists (e.g., albuterol), leukotriene receptor antagonists (e.g., montelukast)), agents used to treat autoimmune disease (glucocorticoids, cyclosporine, tacrolimus, mycophenolate mofetil), agents used to treat nervous system disorders (anticholinesterases, dopamine, levodopa, serotonin receptor agonists (e.g., sumatriptan), amantadine, donepezil, riluzole), agents used to treat ischemia/reperfusion injury (nitroglycerin, nifedipine), and agents used to treat gastrointestinal disorders (neostigmine, metoclopramide, sulfasalazine).

In some embodiments of the present invention, a compound of Formula I and one or more therapeutic agents are administered to an animal at different periodicities, at different durations, at different concentrations, by different administration routes, etc. In some embodiments, the compound is administered prior to the therapeutic agent, e.g., 0.5, 1, 2 3, 4, 5, 10, 12, or 18 hours, 1, 2, 3, 4, 5, or 6 days, 1, 2, 3, or 4 weeks prior to the administration of the therapeutic agent. In some embodiments, the compound is administered after the therapeutic agent, e.g., 0.5, 1, 2 3, 4, 5, 10, 12, or 18 hours, 1, 2, 3, 4, 5, or 6 days, 1, 2, 3, or 4 weeks after the administration of the therapeutic agent. In some embodiments, the compound and the therapeutic agent are administered concurrently but on different schedules, e.g., the compound is administered daily while the therapeutic agent is administered once a week, once every two weeks, once every three weeks, or once every four weeks. In other embodiments, the compound is administered once a week while the therapeutic agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to animals, e.g. humans, orally at a dose of 0.0025 to 50 mg/kg, or an equivalent amount of the pharmaceutically acceptable salt thereof, per day of the body weight of the animal being treated for disorders responsive to inhibition of the CRTH2 receptor. Preferably, about 0.01 to about 10 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 50 mg, preferably about 0.1 to about 10 mg of the compound. The unit dose may be administered one or more times daily as one or more tablets or capsules each containing from about 0.1 to about 10 mg, conveniently about 0.25 to 50 mg of the compound.

In a topical formulation, the compound may be present at a concentration of about 0.01 to 100 mg per gram of carrier. In a preferred embodiment, the compound is present at a concentration of about 0.07-1.0 mg/ml, more preferably, about 0.1-0.5 mg/ml, most preferably, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

General Analytical Conditions

HPLC analysis and purification was performed using a Waters 2525 binary gradient pump, Waters 2767 sample manager, Waters 2487 UV detector (220 and 254 nM), and Waters Micromass ZQ electrospray mass spec detector. The Micromass ZQ was set for both positive and negative ionization (cone voltage=25 and 50, respectively).

Analytical HPLC analysis was performed as follows:
Waters XTerra MS C18 50×4.6 mm 3.5 μm column
Mobile Phase: 10 mM Ammonium Acetate buffer at pH 5.75 and Acetonitrile
Acetonitrile: 10 to 75% at 3.5 minutes, 75 to 99% at 3.9 minutes, 99% hold to 4.2 minutes, 99 to 10% at 4.5 minutes, re-equilibrate.
Preparative HPLC was performed as follows:
Waters XTerra Prep MS C18 50×19 mm 5 μm column
Mobile Phase: 10 mM Ammonium Acetate buffer at pH 5.75 and Acetonitrile
Acetonitrile: 10 to 99% at 8 minutes, 99% hold to 9 minutes, 99 to 10% at 9.5. minutes, re-equilibrate.
NMR analysis was performed using a Bruker BioSpin UltraShield NMR (300 MHz).

EXAMPLE 1

[5-(4-Fluoro-benzenesulfonylamino)-2-propyl-benzoimidazol-1-yl]-acetic acid a.) 4-Fluoro-N-(4-fluoro-3-nitro-phenyl)-benzenesulfonamide: (Scheme 1)

Pyridine (500 uL, 6.19 mmol) was added to a solution of 4-fluoro-3-nitro-phenylamine (1 g, 6.41 mmol) and 4-fluoro-benzenesulfonyl chloride (1.2 g, 6.19 mmol) in dichloromethane (DCM) (20 mL) and the reaction was stirred at room temperature overnight. The reaction was then partitioned between water and DCM. The organic layer was washed several times with water and concentrated. Recrystalization from ethanol/water gave 1.57 g of the sub-title compound as tan crystals.

b.) 4-(4-Fluoro-benzenesulfonylamino)-2-nitro-phenylamino]-acetic acid tert-butyl ester:

The product of step a.) (11.3 g, 36 mmol) in 10 mL DMSO was added to a mixture of glycine tert-butyl ester hydrochloride (7.2 g, 43 mmol) and $NaHCO_3$ (9.0 g, 108 mmol) in 10 mL DMSO. The reaction was heated to 65° C. for 5 hours, cooled to room temperature, and partitioned between water and ethyl acetate. The organic layer was washed several times with water and concentrated to give 11.7 g of the sub-title compound as a yellow solid. MS: ESI (negative): 424 (M–H).

c.) [2-Amino-4-(4-fluoro-benzenesulfonylamino)-phenylamino]-acetic acid tert-butyl ester:

The product of step b.) (1.0 g, 2.35 mmol) was stirred with 3% Pd/C (300 mg) in ethanol (10 mL) under $H_2$ (1 atm) for 3.5 hours. The reaction was filtered over celite and concentrated to dryness to give the sub-title compound as a brown oil. MS: ESI (negative): 394 (M–H).

d.) [5-(4-Fluoro-benzenesulfonylamino)-2-propyl-benzoimidazol-1-yl]-acetic acid tert-butyl ester:

The product from step c.) (100 mg, 0.25 mmol) was dissolved in ethanol (5 mL) and treated with acetic acid (2 drops) followed by butyraldehyde (35 uL, 0.39 mmol). The reaction was heated to 70° C. for 18 hours. The reaction mixture was cooled to ambient temperature and concentrated under reduced pressure to give the crude sub-title compound that was used without further purification.

e.) [5-(4-Fluoro-benzenesulfonylamino)-2-propyl-benzoimidazol-1-yl]-acetic acid:

The product of step d.) was treated with trifluoroacetic acid (TFA) (2 mL) for 2 hours, concentrated, and purified by preparative LCMS to give the title compound. 1H NMR (d6-DMSO) δ10.01 (br s, 1H), 7.74 (dd, J=5.3 Hz, J=8.7 Hz, 2H), 7.35 (t, J=8.7 Hz, 2H), 7.19 (d, J=1.8 Hz, 1H), 6.87 (dd, J=1.8 Hz, J=8.7 Hz, 1H), 4.93 (s, 2H), 2.67 (t, J=7.5 Hz, 2H), 1.72 (sextet, J=7.5 Hz, 2H), 0.95 (t, J=7.5 Hz, 3H). MS: ESI (negative): 390 (M–H).

EXAMPLE 2

[5-(4-Fluoro-benzenesulfonylamino)-2-(1-methyl-butyl)-benzoimidazol-1-yl]-acetic acid a.) [5-(4-Fluoro-benzenesulfonylamino)-2-(1-methyl-butyl)-benzoimidazol-1-yl]-acetic acid tert-butyl ester: (Scheme 1)

The sub-title compound was prepared by the method of example 1, step d.) using 2-methylvaleraldehyde and was used in crude form without purification.

b.) [5-(4-Fluoro-benzenesulfonylamino)-2-(1-methyl-butyl)-benzoimidazol-1-yl]-acetic acid:

The title compound was prepared by the method described in example 1, step e.) using the product from step a.). MS: ESI (negative): 418 (M–H).

EXAMPLE 3

[2-Ethyl-5-(4-fluoro-benzenesulfonylamino)-benzoimidazol-1-yl]-acetic acid a.) [2-Ethyl-5-(4-fluoro-benzenesulfonylamino)-benzoimidazol-1-yl]-acetic acid tert-butyl ester: (Scheme 1)

The sub-title compound was prepared by the method of example 1, step d.) using propionaldehyde and was used in crude form without purification.

b.) [2-Ethyl-5-(4-fluoro-benzenesulfonylamino)-benzoimidazol-1-yl]-acetic acid:

The title compound was prepared by the method described in example 1, step e.) using the product from step a.). MS: ESI (negative): 376 (M–H).

EXAMPLE 4

[2-(1,5-Dimethyl-hex-4-enyl)-5-(4-fluoro-benzene-sulfonylamino)-benzoimidazol-1-yl]-acetic acid a.) [2-(1,5-Dimethyl-hex-4-enyl)-5-(4-fluoro-benzenesulfonylamino)-benzoimidazol-1-yl]-acetic acid tert-butyl ester: (Scheme 1)

The sub-title compound was prepared by the method of example 1, step d.) using 2,6-dimethyl-5-hepten-1-al and was used in crude form without purification.

b.) [2-(1,5-Dimethyl-hex-4-enyl)-5-(4-fluoro-benzenesulfonylamino)-benzoimidazol-1-yl]-acetic acid:

The title compound was prepared by the method described in example 1, step e.) using the product from step a.). MS: ESI (negative): 458 (M–H).

EXAMPLE 5

[5-(4-Fluoro-benzenesulfonylamino)-2-(2-methyl-sulfanyl-ethyl)-benzoimidazol-1-yl]-acetic acid a.) [5-(4-Fluoro-benzenesulfonylamino)-2-(2-methylsulfanyl-ethyl)-benzoimidazol-1-yl]-acetic acid tert-butyl ester: (Scheme 1)

The sub-title compound was prepared by the method of example 1, step d.) using 3-(methylthio)propionaldehyde and was used in crude form without purification.

b.) [5-(4-Fluoro-benzenesulfonylamino)-2-(2-methylsulfanyl-ethyl)-benzoimidazol-1-yl]-acetic acid:

The title compound was prepared by the method described in example 1, step e.) using the product from step a.). MS: ESI (negative): 422 (M–H).

EXAMPLE 6

[2-But-1-enyl-5-(4-fluoro-benzenesulfonylamino)-benzoimidazol-1-yl]-acetic acid a.) [2-But-1-enyl-5-(4-fluoro-benzenesulfonylamino)-benzoimidazol-1-yl]-acetic acid tert-butyl ester: (Scheme 1)

The sub-title compound was prepared by the method of example 1, step d.) using pent-2-enal and was used in crude form without purification.

b.) [2-But-1-enyl-5 -(4-fluoro-benzenesulfonylamino)-benzoimidazol-1-yl]-acetic acid:

The title compound was prepared by the method described in example 1, step e.) using the product from step a.). MS: ESI (negative): 403 (M−H).

EXAMPLE 7

[5-(4-Fluoro-benzenesulfonylamino)-2-isobutyl-benzoimidazol-1-yl]-acetic acid a.) [5-(4-Fluoro-benzenesulfonylamino)-2-isobutyl-benzoimidazol-1-yl]-acetic acid tert-butyl ester: (Scheme 1)

The sub-title compound was prepared by the method of example 1, step d.) using isovaleraldehyde and was used in crude form without purification.

b.) [5-(4-Fluoro-benzenesulfonylamino)-2-isobutyl-benzoimidazol-1-yl]-acetic acid:

The title compound was prepared by the method described in example 1, step e.) using the product from step a.). 1H NMR (d6-DMSO) δ10.03 (br s, 1H), 7.75 (dd, J=5.4 Hz, J=8.7 Hz, 2H), 7.35 (t, J=8.7 Hz, 2H), 7.29 (d, J=8.7 Hz, 1H), 7.20 (d, J=1.8 Hz, 1H), 6.88 (dd, J=1.8 Hz, J=8.7 Hz, 1H), 4.93 (s, 2H), 2.59 (d, J=7.2 Hz, 2H), 2.13 (sext., J=6.6 Hz, 1H), 0.92 (d, J=6.6 Hz, 6H). MS: ESI (negative): 404 (M−H).

EXAMPLE 8

[5-(4-Fluoro-benzenesulfonylamino)-2-(2,4,4-trimethyl-pentyl)-benzoimidazol-1-yl]-acetic acid a.) [5-(4-Fluoro-benzenesulfonylamino)-2-(2,4,4-trimethyl-pentyl)-benzoimidazol-1-yl]-acetic acid tert-butyl ester: (Scheme 1)

The sub-title compound was prepared by the method of example 1, step d.) using 3,5,5-trimethylhexanal and was used in crude form without purification.

b.) [5-(4-Fluoro-benzenesulfonylamino)-2-(2,4,4-trimethyl-pentyl)-benzoimidazol-1-yl]-acetic acid:

The title compound was prepared by the method described in example 1, step e.) using the product from step a.). MS: ESI (negative): 460 (M−H).

EXAMPLE 9

[5-(4-Fluoro-benzenesulfonylamino)-2-pentyl-benzoimidazol-1-yl]-acetic acid a.) [5-(4-Fluoro-benzenesulfonylamino)-2-pentyl-benzoimidazol-1-yl]-acetic acid tert-butyl ester: (Scheme 1)

The sub-title compound was prepared by the method of example 1, step d.) using hexanal and was used in crude form without purification.

b.) [5-(4-Fluoro-benzenesulfonylamino)-2-pentyl-benzoimidazol-1-yl]-acetic acid:

The title compound was prepared by the method described in example 1, step e.) using the product from step a.). MS: ESI (negative): 418 (M−H).

EXAMPLE 10

[2-(1-Ethyl-pentyl)-5-(4-fluoro-benzenesulfonylamino)-benzoimidazol-1-yl]-acetic acid a.) [2-(1 -Ethyl-pentyl)-5-(4-fluoro-benzenesulfonylamino)-benzoimidazol-1-yl]-acetic acid tert-butyl ester: (Scheme 1)

The sub-title compound was prepared by the method of example 1, step d.) using 2-ethyl hexanal and was used in crude form without purification.

b.) [2-(1 -Ethyl-pentyl)-5-(4-fluoro-benzenesulfonylamino)-benzoimidazol-1-yl]-acetic acid:

The title compound was prepared by the method described in example 1, step e.) using the product from step a.). 1H NMR (d6-DMSO) δ10.08 (s, 1H), 7.88 (dd, J=5.3 Hz, J=8.7 Hz, 2H), 7.36 (t, J=8.7 Hz, 2H), 7.29 (d, J=8.7 Hz, 1H), 7.21 (d, J=1.5 Hz, 1H), 6.87 (dd, J=1.8 Hz, J=8.7 Hz, 1H), 5.00 (s, 2H), 2.80 (quin., J=6.0 Hz, 1H), 1.56-1.75 (m, 4H), 1.01-1.24 (m, 4H), 0.77 (t, J=7.5 Hz, 3H), 0.72 (t, J=7.5 Hz, 3H). MS: ESI (negative): 446 (M−H).

EXAMPLE 11

[2-(2-Allyloxycarbonylamino-ethyl)-5 -(4-fluoro-benzenesulfonyl amino)-benzoimidazol-1-yl]-acetic acid a.) (3,3-Diethoxy-propyl)-carbamic acid allyl ester: (Scheme 1)

But-3-enoyl chloride (930 uL, 8.84 mmol) was added slowly to a rapidly stirring mixture of 3,3-diethoxy-propylamine (1.0 g, 6.80 mmol) and NaHCO₃ (2 mL of 0.6 M NaHCO₃ in water) in DCM (100 mL). The reaction was stirred at room temperature overnight, then partitioned between water and DCM. The organic layer was washed several times with water and concentrated to give the crude sub-title compound that was used without further purification.

b.) [2-(2-Allyloxycarbonylamino-ethyl)-5-(4-fluoro-benzenesulfonylamino)-benzoimidazol-1-yl]-acetic acid tert-butyl ester:

The sub-title compound was prepared by the method of example 1, step d.) using (3,3-Diethoxy-propyl)-carbamic acid allyl ester and was used in crude form without purification.

c.) [2-(2-Allyloxycarbonylamino-ethyl)-5-(4-fluoro-benzenesulfonylamino)-benzoimidazol-1-yl]-acetic acid:

The title compound was prepared by the method described in example 1, step e.) using the product from step b.). MS: ESI (negative): 475.5 (M−H).

EXAMPLE 12

[2-Butyl-5-(4-fluoro-benzenesulfonylamino)-benzoimidazol-1-yl]-acetic acid a.) [2-Butyl-5-(4-fluoro-benzenesulfonylamino)-benzoimidazol-1-yl]-acetic acid tert-butyl ester: (Scheme 1)

The sub-title compound was prepared by the method of example 1, step d.) using valeraldehyde and was used in crude form without purification.

b.) [2-Butyl-5-(4-fluoro-benzenesulfonylamino)-benzoimidazol-1-yl]-acetic acid:

The title compound was prepared by the method described in example 1, step e.) using the product from step a.). 1H NMR (d6-DMSO) δ10.01 (br s, 1H), 7.73 (dd, J=5.4 Hz, J=8.7 Hz, 2H), 7.28-7.37 (m, 3H), 7.18 (d, J=1.8 Hz, 1H), 6.86 (dd, J=1.5 Hz, J=8.7 Hz, 1H), 4.95 (s, 2H), 2.69 (t, J=7.5 Hz, 2H), 1.67 (quin., J=7.5 Hz, 2H), 1.35 (sext., J=7.5 Hz, 2H), 0.88 (t, J=7.5 Hz, 3H). MS: ESI (negative): 404 M−H).

EXAMPLE 13

[5-(4-Fluoro-benzenesulfonylamino)-2-isopropyl-benzoimidazol-1-yl]-acetic acid a.) [5-(4-Fluoro-benzenesulfonylamino)-2-isopropyl-benzoimidazol-1-yl]-acetic acid tert-butyl ester: (Scheme 1)

The sub-title compound was prepared by the method of example 1, step d.) using isobutyraldehyde and was used in crude form without purification.

b.) [5-(4-Fluoro-benzenesulfonylamino)-2-isopropyl-benzoimidazol-1-yl]-acetic acid:

The title compound was prepared by the method described in example 1, step e.) using the product from step a.). MS: ESI (negative): 390 M−H).

EXAMPLE 14

{5-[Benzyl-(4-fluoro-benzenesulfonyl)-amino]-2-propyl-benzoimidazol-1-yl}-acetic acid a.) {5-[Benzyl-(4-fluoro-benzenesulfonyl)-amino]-2-propyl-benzoimidazol-1-yl}-acetic acid tert-butyl ester: (Scheme 1)

The product from example 1, step d.) (1.13 g, 2.53 mmol) was dissolved in dimethylformamide (DMF) (30 mL), treated with $K_2CO_3$ (524 mg, 3.79 mmol), benzyl bromide (340 uL, 2.78 mmol), and stirred at room temperature overnight. The reaction mixture was partitioned between ethyl acetate and water. The organic layer was washed several times with water and concentrated under reduced pressure. This compound was purified by chromatography (EtOAc/Hex) prior to use in subsequent steps.

b.) {5-[Benzyl-(4-fluoro-benzenesulfonyl)-amino]-2-propyl-benzoimidazol-1-yl}-acetic acid:

The product from step a.) was treated with TFA for one hour and concentrated. The title compound was purified by preparative LCMS. 1H NMR (d6-DMSO) δ7.75 (dd, J=5.1 Hz, J=9.0 Hz, 2H), 7.46 (t, J=8.7 Hz, 2H), 7.11-7.31 (m, 7H), 6.82 (dd, J=1.8 Hz, J=8.7 Hz, 1H), 5.00 (s, 2H), 4.84 (s, 2H), 3.13 (sext., J=6.9 Hz, 1H), 1.57 (d, J=6.9 Hz, 6H). MS: ESI (negative): 480 M−H).

EXAMPLE 15

{5-[Benzyl-(4-fluoro-benzenesulfonyl)-amino]-2-butyl-benzoimidazol-1-yl}-acetic acid a.) {5-[Benzyl-(4-fluoro-benzenesulfonyl)-amino]-2-butyl-benzoimidazol-1-yl}-acetic acid tert-butyl ester: (Scheme 1)

The product from example 12, step a.) (56 mg, 0.126 mmol) was dissolved in DMF (3 mL), treated with $K_2CO_3$ (26 mg, 0.189 mmol), benzyl bromide (15 uL, 0.126 mmol), and stirred at room temperature overnight. Additional benzyl bromide (15 uL, 0.126 mmol), was added and the reaction was stirred for 72 hours. The reaction mixture was partitioned between ethyl acetate and water. The organic layer was washed several times with water and concentrated under reduced pressure to give the sub-title compound that was used in crude form without purification.

b.) {5-[Benzyl-(4-fluoro-benzenesulfonyl)-amino]-2-butyl-benzoimidazol-1-yl}-acetic acid:

The title compound was prepared by the method described in example 1, step e.) using the product from step a.). MS: ESI (negative): 494 M−H).

EXAMPLE 16

{5-[Benzyl-(4-fluoro-benzenesulfonyl)-amino]-2-isopropyl-benzoimidazol-1-yl}-acetic acid a.) {5-[Benzyl-(4-fluoro-benzenesulfonyl)-amino]-2-isopropyl-benzoimidazol-1-yl}-acetic acid: (Scheme 1)

The sub-title compound was prepared by the method of example 15, step a.) using the product from example 13, step a.) and was used in crude form without purification.

b.) {5-[Benzyl-(4-fluoro-benzenesulfonyl)-amino]-2-isopropyl-benzoimidazol-1-yl}-acetic acid:

The title compound was prepared by the method described in example 1, step e.) using the product from step a.). 1H NMR (d6-DMSO) δ7.75 (dd, J=5.1, 9.0 Hz, 2H), 7.46 (t, J=8.7 2H), 7.11-7.31 (m, 7H), 6.82 (dd, J=1.8, 8.7 Hz, 1H), 5.00 (s, 2H), 4.84 (s, 2H), 3.13 (sext., J=6.9 Hz, 1H) 1.57 (d, J=6.9 Hz, 6H). MS: ESI (negative): 480.5 M−H).

EXAMPLE 17

{2-Butyl-5-[(4-fluoro-benzenesulfonyl)-methyl-amino]-benzoimidazol-1-yl}-acetic acid a.) {2-Butyl-5-[(4-fluoro-benzenesulfonyl)-methyl-amino]-benzoimidazol-1-yl}-acetic acid tert-butyl ester: (Scheme 1)

The sub-title compound was prepared by the method of example 15, step a.) using the product from example 12, step a.) and methyl iodide and was used in crude form without purification.

b.) {2-Butyl-5-[(4-fluoro-benzenesulfonyl)-methyl-amino]-benzoimidazol-1-yl}-acetic acid:

The title compound was prepared by the method described in example 1, step e.) using the product from step a.). MS: ESI (negative): 418 M−H).

EXAMPLE 18

{5-[Ethoxycarbonylmethyl-(4-fluoro-benzenesulfonyl)-amino]-2-propyl-benzoimidazol-1-yl}-acetic acid a.) {5-[Ethoxycarbonylmethyl-(4-fluoro-benzenesulfonyl)-amino]-2-propyl-benzoimidazol-1-yl}-acetic acid tert-butyl ester: (Scheme 1)

The product from example 1, step d.) (50 mg, 0.111 mmol) was dissolved in DMF (1 mL), treated with $K_2CO_3$ (23 mg, 0.167 mmol), bromo-acetic acid ethyl ester (25 uL, 0.133 mmol), and stirred at ambient temperature overnight. The reaction was heated to 50° C. for 2 hours, then more $K_2CO_3$ (23 mg, 0.167 mmol) and bromo-acetic acid ethyl ester (25 uL, 0.133 mmol) were added and the reaction was heated to 80° C. for three hours. The reaction mixture was cooled to room temperature and partitioned between ethyl acetate and water. The organic layer was washed several times with water and concentrated under reduced pressure to give the sub-title compound that was used in crude form without purification.

b.) {5-[Ethoxycarbonylmethyl-(4-fluoro-benzenesulfonyl)-amino]-2-propyl-benzoimidazol-1-yl}-acetic acid:

The title compound was prepared by the method described in example 1, step e.) using the product from step a.). 1H NMR (MeOD) δ7.75 (dd, J=5.1 Hz, J=8.7 Hz, 2H), 7.51 (d, J=1.8 Hz, 1H), 7.48 (d, J=8.7 Hz, 1H), 7.28 (d, J=8.7 Hz, 2H), 7.16 (dd, J=1.8 Hz, J=8.7 Hz, 1H), 5.04 (s, 2H), 4.56 (s, 2H), 2.94 (t, J=7.5 Hz, 2H), 1.58 (sext., J=7.5 Hz, 2H), 1.25 (t, J=7.2 Hz, 3H), 1.08 (t, J=7.5 Hz, 3H). MS: ESI (negative): 476.5 M−H).

EXAMPLE 19

{5-[(4-Fluoro-benzenesulfonyl)-(4-fluoro-benzyl)-amino]-2-propyl-benzoimidazol-1-yl}-acetic acid a.) {5-[(4-Fluoro-benzenesulfonyl)-(4-fluoro-benzyl)-amino]-2-propyl-benzoimidazol-1-yl}-acetic acid tert-butyl ester: (Scheme 1)

The sub-title compound was prepared by the method of example 18, step a.) using 4-fluorobenzyl bromide and was used in crude form without purification.

b.) {5-[(4-Fluoro-benzenesulfonyl)-(4-fluoro-benzyl)-amino]-2-propyl-benzoimidazol-1-yl}-acetic acid:

The title compound was prepared by the method described in example 1, step e.) using the product from step a.). 1H NMR (d6-DMSO) δ7.72 (dd, J=5.1 Hz, J=8.7 Hz, 2H), 7.45 (t, J=8.7 Hz, 2H), 7.30 (t, J=8.7 Hz, 2H), 7.27 (d, J=8.1 Hz, 1H), 7.15 (d, J=1.8 Hz, 1H), 7.05 (t, J=8.7 Hz, 2H), 6.80 (dd, J=1.8 Hz, J=8.7 Hz, 1H), 4.99 (s, 2H), 4.81 (s, 2H), 2.67 (t, J=7.5 Hz, 2H), 1.73 (sext., J=7.5 Hz, 2H), 0.95 (t, J=7.5 Hz, 3H). MS: ESI (negative): 498 M−H).

EXAMPLE 20

{5-[(4-Fluoro-benzenesulfonyl)-(3-methyl-butyl)-amino]-2-propyl-benzoimidazol-1-yl}-acetic acid a.) {5-[(4-Fluoro-benzenesulfonyl)-(3-methyl-butyl)-amino]-2-propyl-benzoimidazol-1-yl}-acetic acid tert-butyl ester: (Scheme 1)

The sub-title compound was prepared by the method of example 18, step a.) using 1-iodo-3-methyl-butane and was used in crude form without purification.

b.) {5-[(4-Fluoro-benzenesulfonyl)-(3-methyl-butyl)-amino]-2-propyl-benzoimidazol-1-yl}-acetic acid:

The title compound was prepared by the method described in example 1, step e.) using the product from step a.). MS: ESI (negative): 460 M−H).

EXAMPLE 21

{5-[(4-Fluoro-benzenesulfonyl)-isopropyl-amino]-2-propyl-benzoimidazol-1-yl}-acetic acid a.) {5-[(4-Fluoro-benzenesulfonyl)-isopropyl-amino]-2-propyl-benzoimidazol-1-yl}-acetic acid tert-butyl ester: (Scheme 1)

The sub-title compound was prepared by the method of example 18, step a.) using 2-iodopropane and was used in crude form without purification.

b.) {5-[(4-Fluoro-benzenesulfonyl)-isopropyl-amino]-2-propyl-benzoimidazol-1-yl}-acetic acid:

The title compound was prepared by the method described in example 1, step e.) using the product from step a.). MS: ESI (negative): 432 M−H).

EXAMPLE 22

{5-[(4-Fluoro-benzenesulfonyl)-(2-methyl-thiazol-4-ylmethyl)-amino]-2-propyl-benzoimidazol-1-yl}-acetic acid a.) {5-[(4-Fluoro-benzenesulfonyl)-(2-methyl-thiazol-4-ylmethyl)-amino]-2-propyl-benzoimidazol-1-yl}-acetic acid tert-butyl ester: (Scheme 1)

The sub-title compound was prepared by the method of example 18, step a.) using 4-(chloromethyl)-2-methyl-1,3-thiazole and was used in crude form without purification.

b.) {5-[(4-Fluoro-benzenesulfonyl)-(2-methyl-thiazol-4-ylmethyl)-amino]-2-propyl-benzoimidazol-1-yl}-acetic acid:

The title compound was prepared by the method described in example 1, step e.) using the product from step a.). MS: ESI (negative): 501 M–H).

EXAMPLE 23

{5-[(2,3-Dihydro-benzo[1,4]dioxin-2-ylmethyl)-(4-fluoro-benzenesulfonyl)-amino]-2-propyl-benzoimidazol-1-yl}-acetic acid a.) {5-[(2,3-Dihydro-benzo[1,4]dioxin-2-ylmethyl)-(4-fluoro-benzenesulfonyl)-amino]-2-propyl-benzoimidazol-1-yl}-acetic acid tert-butyl ester: (Scheme 1)

The sub-title compound was prepared by the method of example 18, step a.) using 2-bromomethyl-1,4-benzodioxane and was used in crude form without purification.

b.) {5-[(2,3-Dihydro-benzo[1,4]dioxin-2-ylmethyl)-(4-fluoro-benzenesulfonyl)-amino]-2-propyl-benzoimidazol-1-yl}-acetic acid:

The title compound was prepared by the method described in example 1, step e.) using the product from step a.). MS: ESI (negative): 538 M–H).

EXAMPLE 24

{5-[(3,5-Dimethyl-isoxazol-4-ylmethyl)-(4-fluoro-benzenesulfonyl)-amino]-2-propyl-benzoimidazol-1-yl}-acetic acid a.) {5-[(3,5-Dimethyl-isoxazol-4-ylmethyl)-(4-fluoro-benzenesulfonyl)-amino]-2-propyl-benzoimidazol-1-yl}-acetic acid tert-butyl ester: (Scheme 1)

The sub-title compound was prepared by the method of example 18, step a.) using 4-(chloromethyl)-3,5-dimethyl-isoxazole and was used in crude form without purification.

b.) {5-[(3,5-Dimethyl-isoxazol-4-ylmethyl)-(4-fluoro-benzenesulfonyl)-amino]-2-propyl-benzoimidazol-1-yl}-acetic acid:

The title compound was prepared by the method described in example 1, step e.) using the product from step a.). MS: ESI (negative): 499 M–H).

EXAMPLE 25

(5-tert-Butoxycarbonylamino-2-propyl-benzoimidazol-1-yl)-acetic acid a.) (4-Fluoro-3-nitro-phenyl)-carbamic acid tert-butyl ester: (Scheme 2)

To a stirred solution of 4-fluoro-3-nitro-phenylamine (10 g, 0.064 mol) in dry THF (300 mL) was added di-tert-butyl dicarbonate (25 g, 0.192 mol) and the reaction was heated to 80° C. for 24 hours. Additional di-tert-butyl dicarbonate (7.0 g, 0.032 mol) was added and the reaction was heated for 24 hours. The reaction was then concentrated, diluted in ethyl acetate, and washed three times with water. The crude product was purified by silica-gel chromatography (EtOAc/Hex) to give 8.0 g of the sub-title compound as a yellow powder. MS: ESI (negative): 255 M–H).

b.) (4-tert-Butoxycarbonylamino-2-nitro-phenylamino)-acetic acid tert-butyl ester:

The product of step a.) (8.0 g, 32 mmol), glycine tert-butyl ester hydrochloride (6.3 g, 38 mmol), and $Na_2CO_3$ (10 g, 96 mmol) were heated to 65° C. overnight in DMF (75 mL). The reaction was diluted in ethyl acetate and washed several times with water. The crude product was purified by silica-gel chromatography (EtOAc/Hex) to give the sub-title compound as a red oil. MS: ESI (positive): 368 (M+H).

c.) (2-Amino-4-tert-butoxycarbonylamino-phenylamino)-acetic acid tert-butyl ester The product of step b.) (2.0 g, 5.45 mmol) was stirred with 3% Pd/C (200 mg) in ethanol (20 mL) under $H_2$ (1 atm) for 90 minutes. The reaction was filtered over celite and concentrated to dryness to give the sub-title compound as a brown oil. This compound was used in crude form without purification. MS: ESI (positive): 338 (M+H).

d.) (5-tert-Butoxycarbonylamino-2-propyl-benzoimidazol-1-yl)-acetic acid tert-butyl ester:

The sub-title compound was prepared by the method of example 1, step d.) using the product of step c.) and was used in crude form without purification. MS: ESI (positive): 390 (M+H).

e.) (5-tert-Butoxycarbonylamino-2-propyl-benzoimidazol-1-yl)-acetic acid:

The product of step d.) was dissolved in 3 mL ethanol, treated with 1 M NaOH (500 µL), and heated to 70° C. for one hour. The reaction was diluted in DCM and extracted with water. The aqueous layer was acidified with 1 M HCl and extracted with DCM. The organic layer was washed with water, concentrated and purified by preparative LCMS to give the title compound. MS: ESI (positive): 334 (M+H).

EXAMPLE 26

[2-Propyl-5-(1,1,3-trioxo-1,3-dihydro-1$\lambda^6$-benzo[d]isothiazol-2-yl)-benzoimidazol-1-yl]-acetic acid a.) (5-Amino-2-propyl-benzoimidazol-1-yl)-acetic acid tert-butyl ester: (Scheme 2)

The product of example 25, step d.) (140 mg, 0.359 mmol) was stirred in 4 M HCl in dioxane (1 mL) at ambient temperature for an hour. The reaction was concentrated to give the sub-title compound that was used in crude form without purification. MS: ESI (positive): 290 (M+H).

b.) 2-(1-tert-Butoxycarbonylmethyl-2-propyl-1H-benzoimidazol-5-ylsulfamoyl)-benzoic acid methyl ester The product of step a.) (40 mg, 0.138 mmol) was stirred with 2-chlorosulfonyl-benzoic acid methyl ester (32 mg, 0.138 mmol), pyridine (200 µL, 2.481 mmol), and Et$_3$N (20 µL, 0.143 mmol) in DCM (5 mL) at ambient temperature overnight. The reaction was then diluted in DCM and washed with water 3× and concentrated to give the sub-title compound that was used in crude form without purification. MS: ESI (positive): 488 (M+H).

c.) [2-Propyl-5-(1,1,3-trioxo-1,3-dihydro-1λ$^6$-benzo[d]isothiazol-2-yl)-benzoimidazol-1-yl]-acetic acid tert-butyl ester:

The product of step b.) (33 mg, 0.069 mmol) was stirred in methanol (2 mL) with Et$_3$N (10 µL, 0.069 mmol) at 65° C. for two hours without change. The reaction was concentrated to dryness and redissolved in toluene (2 mL). Et$_3$N (10 µL, 0.069 mmol) was added to the solution and the reaction was heated to 110° C. overnight. Additional Et$_3$N (35 µL, 0.242 mmol) was added and the reaction was heated overnight to complete reaction. The reaction was then concentrated to give the sub-title compound that was used in crude form without purification. MS: ESI (positive): 456 (M+H).

d.) [2-Propyl-5-(1,1,3-trioxo-1,3-dihydro-1λ$^6$-benzo[d]isothiazol-2-yl)-benzoimidazol-1-yl]-acetic acid:

The title compound was prepared by the method described in example 1, step e.) using the product from step c.). $^1$H NMR (CD$_3$OD) δ 8.17 (t, J=8.1 Hz, 2H), 7.98-8.09 (m, 2H), 7.72 (d, J=1.5 Hz, 1H), 7.58 (d, J=8.4 Hz, 1H), 7.34 (dd, J=2.1 Hz, J=8.7 Hz, 1H), 4.81 (s, 2H), 2.92 (t, J=7.5 Hz, 2H), 1.86-1.96 (m, 2H), 1.08 (t, J=7.2 Hz, 3H). MS: ESI (negative): 398 (M−H).

EXAMPLE 27

{5-[(3-Fluoro-benzenesulfonyl)-(4-fluoro-benzyl)-amino]-2-propyl-benzoimidazol-1-yl}-acetic acid a.) [5-(4-Fluoro-benzylamino)-2-propyl-benzoimidazol-1-yl]-acetic acid tert-butyl ester: (Scheme 2)

Sodium triacetoxyborohydride (191 mg, 0.900 mmol) was added to a solution of the product of example 26, step a.) (500 mg, 1.73 mmol) and 4-fluoro-benzaldehyde (73 µL, 0.692 mmol) in DCE (5 mL) and the reaction was stirred under N$_2$ at ambient temperature for 72 hours. The reaction was diluted in ethyl acetate, washed with H$_2$O (×3) and concentrated to give the subtitle compound in crude form. This compound was purified by silica-gel chromatography (EtOAc/Hex) prior to use in subsequent steps (288 mg, 42%). MS: ESI (positive): 398 (M+H).

b.) {5-[(3-Fluoro-benzenesulfonyl)-(4-fluoro-benzyl)-amino]-2-propyl-benzoimidazol-1-yl}-acetic acid tert-butyl ester:

Pyridine (200 µL, 2.481 mmol) and Et$_3$N (15 µL, 0.104 mmol) were added to a solution of the product of step a.) (40 mg, 0.100 mmol) and 3-fluoro-benzenesulfonyl chloride (13 µL, 0.100 mmol) in DCM (5 mL) and the reaction was stirred at ambient temperature overnight. The reaction was diluted in DCM and washed with H$_2$O. The organic layer was concentrated to give the sub-title compound that was used in crude form without purification.

c.) {5-[(3-Fluoro-benzenesulfonyl)-(4-fluoro-benzyl)-amino]-2-propyl-benzoimidazol-1-yl}-acetic acid:

The title compound was prepared by the method described in example 1, step e.) using the product from step b.). $^1$H NMR (d$_6$-DMSO) δ7.46-7.71 (m, 4H), 7.28-7.35 (m, 3H), 7.17 (d, J=1.8 Hz, 1H), 7.07 (t, J=8.7 Hz, 2H), 6.81 (dd, J=1.5 Hz, J=8.7 Hz, 1H), 5.00 (s, 2H), 4.87 (s, 2H), 2.69 (t, J=7.8 Hz, 2H), 1.73 (sext., J=7.2 Hz, 2H), 0.95 (t, J=7.2 Hz, 3H). MS: ESI (negative): 498 M−H).

EXAMPLE 28

{5-[(2-Fluoro-benzenesulfonyl)-(4-fluoro-benzyl)-amino]-2-propyl-benzoimidazol-1-yl}-acetic acid a.) {5-[(2-Fluoro-benzenesulfonyl)-(4-fluoro-benzyl)-amino]-2-propyl-benzoimidazol-1-yl}-acetic acid tert-butyl ester: (Scheme 2)

The sub-title compound was prepared by the method of example 27, step b.) using 2-fluoro-benzenesulfonyl chloride and was used in crude form without purification.

b.) {5-[(2-Fluoro-benzenesulfonyl)-(4-fluoro-benzyl)-amino]-2-propyl-benzoimidazol-1-yl}-acetic acid:

The title compound was prepared by the method described in example 1, step e.) using the product from step a.). $^1$H NMR (d$_6$-DMSO) δ7.76 (dd, J=6.6 Hz, J=13.2 Hz, 1H), 7.57 (dd, J=6.9 Hz, J=15.3 Hz, 2H), 7.28-7.34 (m, 4H), 7.18 (s, 1H), 7.09 (t, J=8.7 Hz, 3H), 6.81 (d, J=8.1 Hz, 1H), 4.96 (s, 2H), 4.80-4.89 (m, 2H), 2.67 (t, J=7.5 Hz, 2H), 1.71 (sext., J=7.5 Hz, 2H), 0.94 (t, J=7.5 Hz, 3H). MS: ESI (negative): 498 M−H).

EXAMPLE 29

{5-[Ethanesulfonyl-(4-fluoro-benzyl)-amino]-2-propyl-benzoimidazol-1-yl}-acetic acid a.) {5-[Ethanesulfonyl-(4-fluoro-benzyl)-amino]-2-propyl-benzoimidazol-1-yl}-acetic acid tert-butyl ester: (Scheme 2)

The sub-title compound was prepared by the method of example 27, step b.) using ethanesulfonyl chloride and was used in crude form without purification.

b.) {5-[Ethanesulfonyl-(4-fluoro-benzyl)-amino]-2-propyl-benzoimidazol-1-yl}-acetic acid:

The title compound was prepared by the method described in example 1, step e.) using the product from step a.). $^1$H NMR (CD$_3$OD) δ7.46 (d, J=1.8 Hz, 1H), 7.18-7.36 (m, 4H), 6.94 (t, J=8.7 Hz, 2H), 4.91 (s, 2H), 4.71 (s, 2H), 3.18 (q, J=7.2 Hz, 2H), 2.83 (t, J=7.8 Hz, 2H), 1.85 (m, 2H), 1.40 (t, J=7.2 Hz, 3H), 1.04 (t, J=7.2 Hz, 3H). MS: ESI (negative): 432 M−H).

EXAMPLE 30

{5-[(4-Fluoro-benzyl)-(2-methoxy-acetyl)-amino]-2-propyl-benzoimidazol-1-yl}-acetic acid a.) {5-[(4-Fluoro-benzyl)-(2-methoxy-acetyl)-amino]-2-propyl-benzoimidazol-1-yl}-acetic acid tert-butyl ester: (Scheme 2)

Et$_3$N (15 µL, 0.104 mmol) was added to a solution of the product of example 27 step a.) (40 mg, 0.100 mmol) and methoxy-acetyl chloride (10 µL, 0.100 mmol) in DCM (5 mL) and the reaction was stirred at ambient temperature overnight. The reaction was diluted in DCM and washed with H$_2$O. The organic layer was concentrated to give the sub-title compound that was used in crude form without purification.

b.) {5-[(4-Fluoro-benzyl)-(2-methoxy-acetyl)-amino]-2-propyl-benzoimidazol-1-yl}-acetic acid:

The title compound was prepared by the method described in example 1, step e.) using the product from step a.). $^1$H NMR (d$_6$-DMSO) δ7.33 (d, J=8.4 Hz, 1H), 7.21-7.29 (m, 4H), 7.09 (t, J=8.7 Hz, 2H), 6.88 (dd, J=1.8 Hz, J=8.4 Hz, 1H), 4.84 (s, 2H), 4.62 (s, 2H), 3.76 (s, 2H), 2.69 (t, J=7.5 Hz, 2H), 1.75 (sext., J=7.5 Hz, 2H), 0.96 (t, J=7.2 Hz, 3H). MS: ESI (negative): 412 M−H.

EXAMPLE 31

{5-[Cyclopropanecarbonyl-(4-fluoro-benzyl)-amino]-2-propyl-benzoimidazol-1-yl}-acetic acid a.) {5-[Cyclopropanecarbonyl-(4-fluoro-benzyl)-amino]-2-propyl-benzoimidazol-1-yl}-acetic acid tert-butyl ester: (Scheme 2)

The sub-title compound was prepared by the method of example 30, step a.) using cyclopropanecarbonyl chloride and was used in crude form without purification.

b.) {5-[Cyclopropanecarbonyl-(4-fluoro-benzyl)-amino]-2-propyl-benzoimidazol-1-yl}-acetic acid:

The title compound was prepared by the method described in example 1, step e.) using the product from step a.). $^1$H NMR (CD$_3$OD) δ7.40 (d, J=8.7 Hz, 1H), 7.25 (d, J=1.8 Hz, 1H), 7.16-7.21 (m, 3H), 6.94-7.05 (m, 3H), 4.72 (s, 2H), 2.84 (t, J=7.5 Hz, 2H), 1.86 (sext., J=7.8 Hz, 2H), 1.40 (sept., J=4.5 Hz, 1H), 1.04 (t, J=7.5 Hz, 3H), 0.93-0.98 (m, 2H), 0.61-0.67 (m, 2H). MS: ESI (negative): 410 M−H.

EXAMPLE 32

{5-[Benzoyl-(4-fluoro-benzyl)-amino]-2-propyl-benzoimidazol-1-yl}-acetic acid a.) {5-[Benzoyl-(4-fluoro-benzyl)-amino]-2-propyl-benzoimidazol-1-yl}-acetic acid tert-butyl ester: (Scheme 2)

The sub-title compound was prepared by the method of example 30, step a.) using benzoyl chloride and was used in crude form without purification.

b.) {5-[Benzoyl-(4-fluoro-benzyl)-amino]-2-propyl-benzoimidazol-1-yl}-acetic acid:

The title compound was prepared by the method described in example 1, step e.) using the product from step a.). $^1$H NMR (d$_6$-DMSO) δ7.31-7.36 (m, 4H), 7.08-7.24 (m, 7H), 6.82 (d, J=9.0 Hz, 1H), 5.09 (s, 2H), 4.84 (s, 2H), 2.63 (t, J=7.5 Hz, 2H), 1.70 (sext., J=7.2 Hz, 2H), 0.93 (t, J=7.5 Hz, 3H). MS: ESI (negative): 444 M−H.

EXAMPLE 33

{5-[Acetyl-(4-fluoro-benzyl)-amino]-2-propyl-benzoimidazol-1-yl}-acetic acid a.) {5-[Acetyl-(4-fluoro-benzyl)-amino]-2-propyl-benzoimidazol-1-yl}-acetic acid tert-butyl ester: (Scheme 2)

The sub-title compound was prepared by the method of example 30, step a.) using acetyl chloride and was used in crude form without purification.

b.) {5-[Acetyl-(4-fluoro-benzyl)-amino]-2-propyl-benzoimidazol-1-yl}-acetic acid:

The title compound was prepared by the method described in example 1, step e.) using the product from step a.). $^1$H NMR (d$_6$-DMSO) δ7.30 (d, J=8.4 Hz, 1H), 7.21-7.25 (m, 3H), 7.08 (t, J=8.4 Hz, 2H), 6.86 (d, J=8.4 Hz, 1H), 4.85 (s, 2H), 4.49 (s, 2H), 2.69 (t, J=7.5 Hz, 2H), 1.69-1.80 (m, 5H), 0.97 (t, J=7.2 Hz, 3H). MS: ESI (negative): 382 M−H.

EXAMPLE 34

{4-[Benzyl-(3-fluoro-benzenesulfonyl)-amino]-2-propyl-benzoimidazol-1-yl}-acetic acid a.) 4-Nitro-2-propyl-1H-benzoimidazole: (Scheme 3)

3-Nitro-benzene-1,2-diamine (1.0 g, 6.54 mmol) and butyraldehyde (630 µL, 7.19 mmol) were stirred in POCl$_3$ (10 mL) at 85° C. for 3 hours. The reaction was cooled to ambient temperature and poured over ice. The resulting mixture was basified with NH$_4$OH. The precipitate was filtered and washed with ice water to give 1.17 g of the sub-title compound that was used without further purification.

b.) (7-Nitro-2-propyl-benzoimidazol-1-yl)-acetic acid tert-butyl ester (Regioisomer 1) and (4-nitro-2-propyl-benzoimidazol-1-yl)-acetic acid tert-butyl ester (Regioisomer 2):

Potassium tert-butoxide (180 mg, 1.62 mmol) was added to a solution of the product from step a.) (300 mg, 1.46 mmol) in DMSO (3 mL) and was stirred at ambient temperature for 30 minutes. Bromo-acetic acid tert-butyl ester (240 µL, 1.62 mmol) was added and the reaction was stirred at ambient temperature overnight. The reaction was poured into H$_2$O (10 mL) and extracted into ethyl acetate. The organic layers were washed several times with water, dried over MgSO$_4$, filtered and concentrated to give the crude product as a brown oil that was purified by silica-gel chromatography using a ethyl acetate/hexanes gradient (5-30% ethyl acetate) to give regioisomer 1 (R$_{f(regioisomer\ 1)}$: 0.60, TLC-1:1/hexane:ethylacetate) (0.087 g) and regioisomer 2 (R$_{f(regioisomer\ 2)}$: 0.40, TLC-1:1/hexane:ethylacetate) (0.127 g) of the subtitle compound (0.214 g, combined yield: 67%). MS: ESI (positive): 320 (M+H).

Note: Regiochemical assignments were based on catalytic reduction of both purified isomers followed by TFA deprotection to give 2-propyl-6H-imidazo[1,5,4-de]quinoxalin-5-one (from regioisomer 1); MS: ESI (positive): 216 (M+H) and (4-amino-2-propyl-benzoimidazol-1-yl)-acetic acid (from regioisomer 2); MS: ESI (positive): 234 (M+H).

c.) (4-Amino-2-propyl-benzoimidazol-1-yl)-acetic acid tert-butyl ester:

The sub-title compound was prepared by the method of example 1, step c.) using (4-nitro-2-propyl-benzoimidazol-1-yl)-acetic acid tert-butyl ester (regioisomer 2) from step b.) and 10% Pd/C and was used in crude form without purification. MS: ESI (positive): 290 (M+H).

d.) [4-(3-Fluoro-benzenesulfonylamino)-2-propyl-benzoimidazol-1-yl]-acetic acid tert-butyl ester:

The sub-title compound was prepared by the method of example 27, step b.) using the product from step c.) and was used in crude form without purification.

e.) {4-[Benzyl-(3-fluoro-benzenesulfonyl)-amino]-2-propyl-benzoimidazol-1-yl}-acetic acid tert-butyl ester:

The product from step d.) (45 mg, 0.103 mmol) was dissolved in DMF (1 mL), treated with $K_2CO_3$ (20 mg, 0.145 mmol), benzyl bromide (25 µL, 0.206 mmol), and stirred at 80° C. for 3.5 hours. The reaction mixture was partitioned between ethyl acetate and water. The organic layer was washed several times with water and concentrated under reduced pressure to give the sub-title compound that was used in crude form without purification.

f.) {4-[Benzyl-(3-fluoro-benzenesulfonyl)-amino]-2-propyl-benzoimidazol-1-yl}-acetic acid:

The title compound was prepared by the method described in example 1, step e.) using the product from step e.). $^1$H NMR (CD$_3$OD) δ7.13-7.49 (m, 10H), 7.04 (t, J=7.8 Hz, 1H), 6.89 (d, J=7.5 Hz, 1H), 5.15 (s, 2H), 4.65 (s, 2H), 2.78 (t, J=7.8 Hz, 2H), 1.74 (sext., J=7.5 Hz, 2H), 1.00 (t, J=7.5 Hz, 3H). MS: ESI (negative): 480 M–H).

EXAMPLE 35

{4-[(3-Fluoro-benzenesulfonyl)-(2-methoxy-ethyl)-amino]-2-propyl-benzoimidazol-1-yl}-acetic acid a.) {4-[(3-Fluoro-benzenesulfonyl)-(2-methoxy-ethyl)-amino]-2-propyl-benzoimidazol-1-yl}-acetic acid tert-butyl ester: (Scheme 3)

The sub-title compound was prepared by the method of example 34, step e.) using 1-bromo-2-methoxy-ethane and was used in crude form without purification.

b.) {4-[(3-Fluoro-benzenesulfonyl)-(2-methoxy-ethyl)-amino]-2-propyl-benzoimidazol-1-yl}-acetic acid:

The title compound was prepared by the method described in example 1, step e.) using the product from step a.). $^1$H NMR (CD$_3$OD) δ7.44-7.47 (m, 4H), 7.28-7.42 (m, 2H), 7.15 (t, J=7.8 Hz, 1H), 6.97 (d, J=7.8 Hz, 1H), 4.68 (s, 2H), 4.11 (t, J=5.7 Hz, 2H), 3.39 (t, J=5.7 Hz, 2H), 3.22 (s, 3H), 2.77 (t, J=7.5 Hz, 2H), 1.73 (sext., J=7.5 Hz, 2H), 0.99 (t, J=7.2 Hz, 3H). MS: ESI (negative): 448 M–H).

EXAMPLE 36

{4-[(3-Fluoro-benzenesulfonyl)-(3-methyl-butyl)-amino]-2-propyl-benzoimidazol-1-yl}-acetic acid a.) {4-[(3-Fluoro-benzenesulfonyl)-(3-methyl-butyl)-amino]-2-propyl-benzoimidazol-1-yl}-acetic acid tert-butyl ester: (Scheme 3)

The sub-title compound was prepared by the method of example 34, step e.) using 1-iodo-3-methyl-butane and was used in crude form without purification.

b.) {4-[(3-Fluoro-benzenesulfonyl)-(3-methyl-butyl)-amino]-2-propyl-benzoimidazol-1-yl}-acetic acid:

The title compound was prepared by the method described in example 1, step e.) using the product from step a.). $^1$H NMR (d$_6$-DMSO) δ7.64 (d, J=8.7 Hz, 1H), 7.42-7.53 (m, 3H), 7.37 (d, J=7.5 Hz, 1H), 7.12 (t, J=7.5 Hz, 1H), 7.03 (d, J=7.2 Hz, 1H), 4.63 (s, 2H), 3.94 (t, J=6.9 Hz, 2H), 2.60 (t, J=7.5 Hz, 2H), 1.55-1.70 (m, 3H), 1.17 (q, J=7.2 Hz, 2H), 0.88 (t, J=7.5 Hz, 3H), 0.75 (d, J=6.6 Hz, 6H). MS: ESI (negative): 460 M–H).

EXAMPLE 37

{4-[(3-Fluoro-benzenesulfonyl)-(4-fluoro-benzyl)-amino]-2-propyl-benzoimidazol-1-yl}-acetic acid a.) {4-[(3-Fluoro-benzenesulfonyl)-(4-fluoro-benzyl)-amino]-2-propyl-benzoimidazol-1-yl}-acetic acid tert-butyl ester: (Scheme 3)

The sub-title compound was prepared by the method of example 34, step e.) using 1-bromomethyl-4-fluoro-benzene and was used in crude form without purification.

b.) {4-[(3-Fluoro-benzenesulfonyl)-(4-fluoro-benzyl)-amino]-2-propyl-benzoimidazol-1-yl}-acetic acid:

The title compound was prepared by the method described in example 1, step e.) using the product from step a.). $^1$H NMR (CD$_3$OD) δ7.23-7.49 (m, 7H), 7.09 (t, J=7.8 Hz, 1H), 6.85-6.92 (m, 3H), 5.10 (s, 2H), 4.72 (s, 2H), 2.81 (t, J=7.5 Hz, 2H), 1.75 (sext., J=7.5 Hz, 2H), 1.00 (t, J=7.2 Hz, 3H). MS: ESI (negative): 498 M–H).

EXAMPLE 38

{4-[(3-Fluoro-benzenesulfonyl)-isopropyl-amino]-2-propyl-benzoimidazol-1-yl}-acetic acid a.) {4-[(3-Fluoro-benzenesulfonyl)-isopropyl-amino]-2-propyl-benzoimidazol-1-yl}-acetic acid tert-butyl ester: (Scheme 3)

The sub-title compound was prepared by the method of example 34, step e.) using 2-iodo-propane and was used in crude form without purification.

b.) {4-[(3-Fluoro-benzenesulfonyl)-isopropyl-amino]-2-propyl-benzoimidazol-1-yl}-acetic acid:

The title compound was prepared by the method described in example 1, step e.) using the product from step a.). $^1$H NMR ($d_6$-DMSO) δ8.46 (dt, J=1.8 Hz, J=6.9 Hz, 1H), 8.01 (d, J=7.8 Hz, 1H), 7.51-7.72 (m, 2H), 7.43 (d, J=8.1 Hz, 1H), 7.15 (t, J=8.1 Hz, 1H), 6.94 (d, J=7.5 Hz, 1H), 4.57 (s, 2H), 4.12 (quint., J=6.6 Hz, 1H), 2.74 (t, J=7.2 Hz, 2H), 1.85 (sext., J=7.5 Hz, 2H), 0.97-1.05 (m, 9H). MS: ESI (negative): 432 M–H).

EXAMPLE 39

{4-[Benzyl-(4-fluoro-phenylmethanesulfonyl)-amino]-2-propyl-benzoimidazol-1-yl}-acetic acid a.) [4-(4-Fluoro-phenylmethanesulfonylamino)-2-propyl-benzoimidazol-1-yl]-acetic acid: (Scheme 3)

Pyridine (800 μL, 9.92 mmol) and Et$_3$N (90 μL, 0.624 mmol) were added to a solution of the product of example 34, step c.) (75 mg, 0.260 mmol) and 4-fluoro-benzenesulfonyl chloride (94 mg, 0.452 mmol) in DCM (10 mL) and the reaction was stirred at ambient temperature for three days. Incomplete reaction was observed. The reaction was concentrated, dissolved in DMF (2 mL) and pyridine (200 μL, 2.48 mmol), and heated to 80° C. overnight. Additional 4-fluoro-benzenesulfonyl chloride (20 mg, 0.096 mmol) was added to the reaction and heating was continued for 2 h. The reaction was diluted in ethyl acetate and washed with H$_2$O. The organic layer was concentrated to give the sub-title compound that was used in crude form without purification.

b.) {4-[Benzyl-(4-fluoro-phenylmethanesulfonyl)-amino]-2-propyl-benzoimidazol-1-yl}-acetic acid tert-butyl ester:

The sub-title compound was prepared by the method of example 34, step e.) using the product from step a.) and was used in crude form without purification.

c.) {4-[Benzyl-(4-fluoro-phenylmethanesulfonyl)-amino]-2-propyl-benzoimidazol-1-yl}-acetic acid:

The title compound was prepared by the method described in example 1, step e.) using the product from step b.). $^1$H NMR (CD$_3$OD) δ7.55 (dd, J=5.4 Hz, J=8.7 Hz, 2H), 7.32 (d, J=7.5 Hz, 1H), 7.16-7.21 (m, 5H), 7.02-7.10 (m, 3H), 6.91 (d, J=7.2 Hz, 1H), 5.11 (s, 2H), 4.74 (s, 2H), 4.62 (s, 2H), 2.95 (t, J=7.8 Hz, 2H), 1.88-2.01 (m, 2H), 1.09 (t, J=7.5 Hz, 3H). MS: ESI (negative): 494 M–H).

EXAMPLE 40

{7-[Benzyl-(4-fluoro-benzenesulfonyl)-amino]-2-propyl-benzoimidazol-1-yl}-acetic acid a.) (7-Amino-2-propyl-benzoimidazol-1-yl)-acetic acid tert-butyl ester: (Scheme 3)

The sub-title compound was prepared by the method of example 1, step c.) using (7-nitro-2-propyl-benzoimidazol-1-yl)-acetic acid tert-butyl ester from example 34, step b.) (regioisomer 1) and 10% Pd/C and was used in crude form without purification.

b.) [7-(4-Fluoro-benzenesulfonylamino)-2-propyl-benzoimidazol-1-yl]-acetic acid tert-butyl ester:

Pyridine (53 μL, 0.656 mmol) was added to a solution of the product of step a.) (189 mg, 0.656 mmol) and 4-fluoro-benzenesulfonyl chloride (127 mg, 0.656 mmol) in DCM (20 mL) and the reaction was stirred at ambient temperature for 72 hours. The reaction was diluted in DCM and washed with H$_2$O. The organic layer was concentrated to give the sub-title compound that was used in crude form without purification.

c.) {7-[Benzyl-(4-fluoro-benzenesulfonyl)-amino]-2-propyl-benzoimidazol-1-yl}-acetic acid tert-butyl ester:

The sub-title compound was prepared by the method of example 34, step e.) using the product from step b.) and was used in crude form without purification.

d.) {7-[Benzyl-(4-fluoro-benzenesulfonyl)-amino]-2-propyl-benzoimidazol-1-yl}-acetic acid The title compound was prepared by the method described in example 1, step e.) using the product from step c.). $^1$H NMR (CD$_3$OD) δ7.87 (dd, J=5.1 Hz, J=9 Hz, 1H), 7.71 (dd, J=5.1 Hz, J=8.7 Hz, 2H), 7.55 (d, J=7.5 Hz, 1H), 7.32 (t, J=8.7 Hz, 2H), 7.04-7.18 (m, 6H), 6.47 (d, J=7.8 Hz, 1H), 5.18 (s, 2H), 2.71 (oct., J=7.2 Hz, 2H), 1.81 (sext., J=7.5 Hz, 2H), 0.99 (t, J=7.2 Hz, 3H). MS: ESI (negative): 480 M–H).

EXAMPLE 41

{5-[(2-Chloro-benzyl)-(4-fluoro-benzenesulfonyl)-amino]-2-propyl-benzoimidazol-1-yl}-acetic acid a.) 4-Fluoro-N-(4-fluoro-3-nitro-phenyl)-benzene-sulfonamide. (Scheme 1)

Pyridine (500 μL, 6.19 mmol) was added to a solution of 4-fluoro-3-nitro-phenylamine (1 g, 6.41 mmol) and 4-fluoro-benzenesulfonyl chloride (1.2 g, 6.19 mmol) in DCM (20 mL) and the reaction was stirred at room temperature overnight. The reaction was then partitioned between water and DCM. The organic layer was washed several times with water and concentrated. Recrystalization from ethanol/water gave 1.57 g of the sub-title compound as tan crystals.

b.) 4-(4-Fluoro-benzenesulfonylamino)-2-nitro-phenylamino]-acetic acid tert-butyl ester.

Glycine tert-butyl ester hydrochloride (7.2 g, 43 mmol) and NaHCO$_3$ (9.0 g, 108 mmol) were added to a solution of 4-fluoro-N-(4-fluoro-3-nitro-phenyl)-benzenesulfonamide (11.3 g, 36.0 mmol) in DMSO (36 mL). The reaction was heated to 65° C. for 5 hours, cooled to room temperature, and partitioned between H$_2$O and EtOAc. The organic layer was washed several times with H$_2$O and concentrated to afford 11.4 g (75% yield) of the sub-title compound as a yellow solid. MS calculated for $C_{18}H_{20}FN_3O_6S$—H: 424, observed: 424.

c.) [2-Amino-4-(4-fluoro-benzenesulfonylamino)-phenylamino]-acetic acid tert-butyl ester.

4-(4-Fluoro-benzenesulfonylamino)-2-nitro-phenylamino]-acetic acid tert-butyl ester (11.4 g, 26.8 mmol) was dissolved in MeOH (135 mL) and purged with N$_2$. Palladium on activated carbon (3.4 g, 10% by weight) was added, and the reaction mixture was charged with a balloon of $H_2$. The reaction mixture was stirred for 3 h at room temperature, and then filtered through a pad of celite. The celite was washed with MeOH, and the filtrate was concentrated to afford 12.5 g (quantitative yield) of the sub-titled compound. MS calculated for $C_{18}H_{22}FN_3O_4S$—H: 394, observed: 394.

d.) [5-(4-Fluoro-benzenesulfonylamino)-2-propyl-benzoimidazol-1-yl]-acetic acid tert-butyl ester.

Butyraldehyde (3.8 mL, 41.8 mmol) and acetic acid (1.4 mL) were added to a solution of [2-amino-4-(4-fluoro-benzenesulfonylamino)-phenylamino]-acetic acid tert-butyl ester (12.5 g, 26.8 mmol) in EtOH (135 mL), and stirred overnight at 70° C. The reaction mixture was cooled to ambient temperature and concentrated under reduced pressure to give the crude sub-titled compound that was used without further purification. MS calculated for $C_{22}H_{26}FN_3O_4S$—H: 446, observed: 446.

e.) {5-[(2-Chloro-benzyl)-(4-fluoro-benzenesulfonyl)-amino]-2-propyl-benzoimidazol-1-yl}-acetic acid tert-butyl ester.

2-Chlorobenzyl chloride (0.27 mmol) and $K_2CO_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in $CH_3CN$ (1 mL), and stirred overnight at 80° C. The reaction mixture was diluted with EtOAc and $H_2O$, and then filtered through an Extrelut column. The column was washed with EtOAc, and the filtrate was concentrated. The crude product was carried onto the next reaction without any further purification or characterization.

f.) {5-[(2-Chloro-benzyl)-(4-fluoro-benzenesulfonyl)-amino]-2-propyl-benzoimidazol-1-yl}-acetic acid.

{5-[(2-Chloro-benzyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1H$ NMR ($d_6$-DMSO) δ7.72 (m, 2H), 7.48 (m, 3H), 7.30 (m, 3H), 7.21 (m, 2H), 6.81 (dd, 1H), 4.96 (s, 2H), 4.87 (s, 2H), 2.67 (t, 2H), 1.72 (m, 2H), 0.94 (t, 3H). MS calculated for $C_{25}H_{23}FClN_3O_4S$—H: 514, observed: 514.

EXAMPLE 42

{5-[(3-Chloro-benzyl)-(4-fluoro-benzenesulfonyl)-amino]-2-propyl-benzoimidazol-1-yl}-acetic acid a.) {5-[(3-Chloro-benzyl)-(4-fluoro-benzenesulfonyl)-amino]-2-propyl-benzoimidazol-1-yl}-acetic acid tert-butyl ester. (Scheme 1)

3-Chlorobenzyl chloride (0.27 mmol) and $K_2CO_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in $CH_3CN$ (1 mL), and stirred overnight at 80° C. The reaction mixture was diluted with EtOAc and $H_2O$, and then filtered through an Extrelut column. The column was washed with EtOAc, and the filtrate was concentrated. The crude product was carried onto the next reaction without any further purification or characterization.

b.) {5-[(3-Chloro-benzyl)-(4-fluoro-benzenesulfonyl)-amino]-2-propyl-benzoimidazol-1-yl}-acetic acid.

{5-[(3-Chloro-benzyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1H$ NMR ($d_6$-DMSO) δ7.72 (m, 2H), 7.46 (m, 2H), 7.23 (m, 4H), 7.16 (d, 1H), 7.10 (d, 1H), 6.76 (dd, 1H), 4.82 (s, 2H), 4.32 (s, 2H), 2.67 (t, 2H), 1.72 (m, 2H), 0.94 (t, 3H). MS calculated for $C_{25}H_{23}FClN_3O_4S$—H: 514, observed: 514.

EXAMPLE 43

{5-[(4-Chloro-benzyl)-(4-fluoro-benzenesulfonyl)-amino]-2-propyl-benzoimidazol-1-yl}-acetic acid a.) {5-[(4-Chloro-benzyl)-(4-fluoro-benzenesulfonyl)-amino]-2-propyl-benzoimidazol-1-yl}-acetic acid tert-butyl ester. (Scheme 1)

4-Chlorobenzyl chloride (0.27 mmol) and $K_2CO_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in $CH_3CN$ (1 mL), and stirred overnight at 80° C. The reaction mixture was diluted with EtOAc and $H_2O$, and then filtered through an Extrelut column. The column was washed with EtOAc, and the filtrate was concentrated. The crude product was carried onto the next reaction without any further purification or characterization.

b.) {5-[(4-Chloro-benzyl)-(4-fluoro-benzenesulfonyl)-amino]-2-propyl-benzoimidazol-1-yl}-acetic acid.

{5-[(4-Chloro-benzyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1H$ NMR ($d_6$-DMSO) δ7.72 (m, 2H), 7.48 (m, 2H), 7.31 (m, 4H), 7.18 (d, 1H), 7.08 (d, 1H), 6.72 (dd, 1H), 4.81 (s, 2H), 4.35 (s, 2H), 2.67 (t, 2H), 1.72 (m, 2H), 0.94 (t, 3H). MS calculated for $C_{25}H_{23}FClN_3O_4S$—H: 514, observed: 514.

EXAMPLE 44

{5-[(2,3-Dichloro-benzyl)-(4-fluoro-benzenesulfonyl)-amino]-2-propyl-benzoimidazol-1-yl}-acetic acid a.) {5-[(2,3-Dichloro-benzyl)-(4-fluoro-benzenesulfonyl)-amino]-2-propyl-benzoimidazol-1-yl}-acetic acid tert-butyl ester. (Scheme 1)

2,3-Dichlorobenzyl chloride (0.27 mmol) and $K_2CO_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in $CH_3CN$ (1 mL), and stirred overnight at 80° C. The reaction mixture was diluted with EtOAc and $H_2O$, and then filtered through an Extrelut column. The column was washed with EtOAc, and the filtrate was concentrated. The crude product was carried onto the next reaction without any further purification or characterization.

b.) {5-[(2,3-Dichloro-benzyl)-(4-fluoro-benzene-sulfonyl)-amino]-2-propyl-benzoimidazol-1-yl}-acetic acid.

{5-[(2,3-Dichloro-benzyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.72 (m, 2H), 7.48 (m, 4H), 7.22 (m, 3H), 6.79 (dd, 1H), 4.99 (s, 2H), 4.51 (s, 2H), 2.67 (t, 2H), 1.72 (m, 2H), 0.94 (t, 3H). MS calculated for C$_{25}$H$_{22}$FCl$_2$N$_3$O$_4$S—H: 548, observed: 548.

EXAMPLE 45

{5-[(2-Trifluoromethyl-benzyl)-(4-fluoro-benzene-sulfonyl)-amino]-2-propyl-benzoimidazol-1-yl}-acetic acid a.) {5-[(2-Trifluoromethyl-benzyl)-(4-fluoro-benzenesulfonyl)-amino]-2-propyl-benzoimidazol-1-yl}-acetic acid tert-butyl ester. (Scheme 1)

2-Trifluoromethylbenzyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(2-Trifluoromethyl-benzyl)-(4-fluoro-benzenesulfonyl)-amino]-2-propyl-benzoimidazol-1-yl}-acetic acid.

{5-[(2-Trifluoromethyl-benzyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.88 (d, 1H), 7.72 (m, 2H), 7.62 (m, 2H), 7.44 (m, 3H), 7.32 (d, 1H), 7.23 (d, 1H), 6.86 (dd, 1H), 5.03 (s, 2H), 4.95 (s, 2H), 2.67 (t, 2H), 1.72 (m, 2H), 0.96 (t, 3H). MS calculated for C$_{26}$H$_{23}$F$_4$N$_3$O$_4$S—H: 548, observed: 548.

EXAMPLE 46

{5-[(Cyclohexyl)-(4-fluoro-benzenesulfonyl)-amino]-2-propyl-benzoimidazol-1-yl}-acetic acid a.) {5-[(Cyclohexyl)-(4-fluoro-benzenesulfonyl)-amino]-2-propyl-benzoimidazol-1-yl}-acetic acid tert-butyl ester. (Scheme 1)

Cyclohexyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(Cyclohexyl)-(4-fluoro-benzenesulfonyl)-amino]-2-propyl-benzoimidazol-1-yl}-acetic acid.

{5-[(Cyclohexyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.81 (m, 1H), 7.42 (m, 3H), 7.08 (d, 1H), 6.79 (dd, 1H), 4.98 (s, 2H), 4.11 (m, 1H), 2.72 (t, 2H), 1.79 (m, 4H), 1.65 (m, 2H), 1.31 (m, 3H), 0.99 (m, 5H), 0.79 (m, 1H). MS calculated for C$_{24}$H$_{28}$FN$_3$O$_4$S—H: 472, observed: 472.

EXAMPLE 47

{5-[[2-(4-Chloro-phenoxy)-ethyl]-(4-fluoro-benzenesulfonyl)-amino]-2-propyl-benzoimidazol-1-yl}-acetic acid a.) {5-[[2-(4-Chloro-phenoxy)-ethyl]-(4-fluoro-benzenesulfonyl)-amino]-2-propyl-benzoimidazol-1-yl}-acetic acid tert-butyl ester. (Scheme 1)

4-Chlorophenyl 2-bromoethyl ether (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[[2-(4-Chloro-phenoxy)-ethyl]-(4-fluoro-benzenesulfonyl)-amino]-2-propyl-benzoimidazol-1-yl}-acetic acid.

{5-[[2-(4-Chloro-phenoxy)-ethyl]-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.71 (m, 2H), 7.41 (m, 2H), 7.28 (m, 3H), 7.11 (d, 1H), 6.95 (d, 1H), 6.82 (m, 2H), 4.66 (s, 2H), 3.98 (m, 4H), 2.71 (t, 2H), 1.72 (m, 2H), 0.99 (t, 3H). MS calculated for C$_{26}$H$_{25}$FClN$_3$O$_5$S—H: 544, observed: 544.

EXAMPLE 48

{5-[(4-Fluoro-benzenesulfonyl)-(3-phenyl-propyl)-amino]-2-propyl-benzoimidazol-1-yl}-acetic acid a.) {5-[(4-Fluoro-benzenesulfonyl)-(3-phenyl-propyl)-amino]-2-propyl-benzoimidazol-1-yl}-acetic acid tert-butyl ester. (Scheme 1)

1-Bromo-3-phenylpropane (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(4-Fluoro-benzenesulfonyl)-(3-phenyl-propyl)-amino]-2-propyl-benzoimidazol-1-yl}-acetic acid.

{5-[(4-Fluoro-benzenesulfonyl)-(3-phenyl-propyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.62 (m, 2H), 7.41 (m, 2H), 7.25 (m, 3H), 7.11 (d, 3H), 6.82 (m, 1H), 4.58 (s, 2H), 3.62 (t, 2H), 2.71 (t, 2H), 2.60 (m, 2H), 1.72 (m, 2H), 1.58 (m, 2H), 0.99 (t, 3H). MS calculated for $C_{27}H_{28}FN_3O_4S$—H: 508, observed: 508.

EXAMPLE 49

{5-[(4-Fluoro-benzenesulfonyl)-(3-phenoxy-propyl)-amino]-2-propyl-benzoimidazol-1-yl}-acetic acid a.) {5-[(4-Fluoro-benzenesulfonyl)-(3-phenoxy-propyl)-amino]-2-propyl-benzoimidazol-1-yl}-acetic acid tert-butyl ester. (Scheme 1)

3-Phenoxypropyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column.

The column was washed with EtOAc, and the filtrate was concentrated. The crude product was carried onto the next reaction without any further purification or characterization.

b.) {5-[(4-Fluoro-benzenesulfonyl)-(3-phenoxy-propyl)-amino]-2-propyl-benzoimidazol-1-yl}-acetic acid.

{5-[(4-Fluoro-benzenesulfonyl)-(3-phenoxy-propyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.62 (m, 2H), 7.30 (m, 6H), 6.88 (m, 4H), 4.62 (s, 2H), 3.99 (t, 2H), 3.74 (t, 2H), 2.71 (m, 2H), 1.71 (m, 4H), 0.99 (t, 3H). MS calculated for $C_{27}H_{26}FN_3O_5S$—H: 524, observed: 524.

EXAMPLE 50

{5-[(4-Fluoro-benzenesulfonyl)-(3-fluoro-benzyl)-amino]-2-propyl-benzoimidazol-1-yl}-acetic acid a.) {5-[(4-Fluoro-benzenesulfonyl)-(3-fluoro-benzyl)-amino]-2-propyl-benzoimidazol-1-yl}-acetic acid tert-butyl ester. (Scheme 1)

3-Fluorobenzyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(4-Fluoro-benzenesulfonyl)-(3-fluoro-benzyl)-amino]-2-propyl-benzoimidazol-1-yl}-acetic acid.

{5-[(4-Fluoro-benzenesulfonyl)-(3-fluoro-benzyl)-amino]-2-propyl-benzoimidazol-1-yl}-acetic acid tert-butyl ester was treated with TFA (2 mL) for 2 hours, concentrated, and purified by preparative LCMS to give the title compound. MS calculated for $C_{25}H_{23}F_2N_3O_4S$—H: 498, observed: 498.

EXAMPLE 51

{5-[(4-Fluoro-benzenesulfonyl)-(3-trifluoromethyl-benzyl)-amino]-2-propyl-benzoimidazol-1-yl}-acetic acid a.) {5-[(4-Fluoro-benzenesulfonyl)-(3-trifluoromethyl-benzyl)-amino]-2-propyl-benzoimidazol-1-yl}-acetic acid tert-butyl ester. (Scheme 1)

3-Trifluoromethylbenzyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(4-Fluoro-benzenesulfonyl)-(3-trifluoromethyl-benzyl)-amino]-2-propyl-benzoimidazol-1-yl}-acetic acid.

{5-[(4-Fluoro-benzenesulfonyl)-(3-trifluoromethyl-benzyl)-amino]-2-propyl-benzoimidazol-1-yl}-acetic acid tert-butyl ester was treated with TFA (2 mL) for 2 hours, concentrated, and purified by preparative LCMS to give the title compound. MS calculated for $C_{26}H_{23}F_4N_3O_4S$—H: 548, observed: 548.

EXAMPLE 52

{5-[(4-Cyano-benzyl)-(4-fluoro-benzenesulfonyl)-amino]-2-propyl-benzoimidazol-1-yl}-acetic acid a.) {5-[(4-Cyano-benzyl)-(4-fluoro-benzenesulfonyl)-amino]-2-propyl-benzoimidazol-1-yl}-acetic acid tert-butyl ester. (Scheme 1)

4-Cyanobenzyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(4-Cyano-benzyl)-(4-fluoro-benzenesulfonyl)-amino]-2-propyl-benzoimidazol-1-yl}-acetic acid.

{5-[(4-Cyano-benzyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.72 (m, 4H), 7.48 (m, 4H), 7.16 (m, 2H), 6.78 (m, 1H), 4.92 (s, 2H), 4.33 (s, 2H), 2.65 (t, 2H), 1.71 (m, 2H), 0.95 (t, 3H). MS calculated for $C_{26}H_{23}FN_4O_4S$+H: 507, observed: 507.

EXAMPLE 53

{5-[(4-Trifluoromethoxy-benzyl)-(4-fluoro-benzene-sulfonyl)-amino]-2-propyl-benzoimidazol-1-yl}-acetic acid a.) {5-[(4-Trifluoromethoxy-benzyl)-(4-fluoro-benzenesulfonyl)-amino]-2-propyl-benzoimidazol-1-yl}-acetic acid tert-butyl ester. (Scheme 1)

4-Trifluoromethoxybenzyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(4-Trifluoromethoxy-benzyl)-(4-fluoro-benzenesulfonyl)-amino]-2-propyl-benzoimidazol-1-yl}-acetic acid.

{5-[(4-Trifluoromethoxy-benzyl)-(4-fluoro-benzene-sulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ7.72 (m, 2H), 7.44 (m, 4H), 7.23 (m, 3H), 7.16 (d, 1H), 6.79 (m, 1H), 4.88 (s, 2H), 4.54 (s, 2H), 2.68 (t, 2H), 1.72 (m, 2H), 0.95 (t, 3H). MS calculated for $C_{26}H_{23}F_4N_3O_5S$—H: 564, observed: 564.

EXAMPLE 54

{5-[(2-Cyano-benzyl)-(4-fluoro-benzenesulfonyl)-amino]-2-propyl-benzoimidazol-1-yl}-acetic acid a.) {5-[(2-Cyano-benzyl)-(4-fluoro-benzenesulfonyl)-amino]-2-propyl-benzoimidazol-1-yl}-acetic acid tert-butyl ester. (Scheme 1)

2-Cyanobenzyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[(2-Cyano-benzyl)-(4-fluoro-benzenesulfonyl)-amino]-2-propyl-benzoimidazol-1-yl}-acetic acid.

{5-[(2-Cyano-benzyl)-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. MS calculated for $C_{26}H_{23}FN_4O_4S$+H: 507, observed: 507.

EXAMPLE 55

{5-[Benzothiazol-2-ylmethyl-(4-fluoro-benzene-sulfonyl)-amino]-2-propyl-benzoimidazol-1-yl}-acetic acid a.) {5-[Benzothiazol-2-ylmethyl-(4-fluoro-benzene-sulfonyl)-amino]-2-propyl-benzoimidazol-1-yl}-acetic acid tert-butyl ester. (Scheme 1)

2-Bromomethyl benzothiazole (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[Benzothiazol-2-ylmethyl-(4-fluoro-benzene-sulfonyl)-amino]-2-propyl-benzoimidazol-1-yl}-acetic acid.

{5-[Benzothiazol-2-ylmethyl-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. $^1$H NMR (d$_6$-DMSO) δ8.08 (m, 1H), 7.86 (m, 1H), 7.79 (m, 2H), 7.45 (m, 4H), 7.25 (m, 2H), 6.91 (d, 1H), 5.33 (s, 2H), 4.39 (s, 2H), 2.65 (t, 2H), 1.72 (m, 2H), 0.92 (t, 3H). MS calculated for $C_{26}H_{23}FN_4O_4S_2$+H: 539, observed: 539.

EXAMPLE 56

{5-[But-2-enyl-(4-fluoro-benzenesulfonyl)-amino]-2-propyl-benzoimidazol-1-yl}-acetic acid a.) {5-[But-2-enyl-(4-fluoro-benzenesulfonyl)-amino]-2-propyl-benzoimidazol-1-yl}-acetic acid tert-butyl ester. (Scheme 1)

Crotyl bromide (0.27 mmol) and K$_2$CO$_3$ (63 mg, 0.45 mmol) were added to a solution of [5-(4-fluoro-benzenesulfonylamino)-2-propyl-benzoimidazol-1-yl]-acetic acid tert-butyl ester (40 mg, 0.09 mmol) in CH$_3$CN (1 mL), and stirred overnight at 80° C. The reaction mixture was diluted with EtOAc and H$_2$O, and then filtered through an Extrelut column. The column was washed with EtOAc, and the filtrate was concentrated. The crude product was carried onto the next reaction without any further purification or characterization.

b.) {5-[But-2-enyl-(4-fluoro-benzenesulfonyl)-amino]-2-propyl-benzoimidazol-1-yl}-acetic acid.

{5-[But-2-enyl-(4-fluoro-benzenesulfonyl)-amino]-2-propyl-benzoimidazol-1-yl}-acetic acid tert-butyl ester was treated with TFA (2 mL) for 2 hours, concentrated, and purified by preparative LCMS to give the title compound. MS calculated for $C_{22}H_{24}FN_3O_4S$—H: 444, observed: 444.

EXAMPLE 57

[5-(Acetyl-benzyl-amino)-2-propyl-benzoimidazol-1-yl]-acetic acid a.) (4-tert-Butoxycarbonylamino-2-nitro-phenylamino)-acetic acid tert-butyl ester. (Scheme 2)

Glycine tert-butyl ester hydrochloride (4.1 g, 29.4 mmol) and NaHCO$_3$ (5.1 g, 61.0 mmol) were added to a solution of (4-fluoro-3-nitro-phenyl)-carbamic acid tert-butyl ester (5.2 g, 20.3 mmol) in DMSO (16 mL). The reaction was heated to 65° C. for 5 hours, cooled to room temperature, and partitioned between H$_2$O and EtOAc. The organic layer was washed several times with H$_2$O and concentrated to afford the sub-title compound. MS calculated for $C_{17}H_{25}N_3O_6$+H: 368, observed: 368.

b.) (2-Amino-4-tert-butoxycarbonylamino-phenylamino)-acetic acid tert-butyl ester.

(4-tert-Butoxycarbonylamino-2-nitro-phenylamino)-acetic acid tert-butyl ester (10.8 g, 29.4 mmol) was dissolved in MeOH (70 mL) and purged with N$_2$. Palladium on activated carbon (2.2 g, 10% by weight) was added, and the reaction mixture was charged with a balloon of H$_2$. The reaction mixture was stirred for 3 h at room temperature, and then filtered through a pad of celite. The celite was washed with MeOH, and the filtrate was concentrated to afford 2.1 g (22%—two steps) of the sub-title compound. MS calculated for $C_{17}H_{27}N_3O_4$+H: 338, observed: 338.

c.) (5-tert-Butoxycarbonylamino-2-propyl-benzoimidazol-1-yl)-acetic acid tert-butyl ester.

Butyraldehyde (0.65 mL, 9.0 mmol) and acetic acid (7 drops) were added to a solution of (2-amino-4-tert-butoxycarbonylamino-phenylamino)-acetic acid tert-butyl ester (2.2 g, 6.5 mmol) in EtOH (100 mL), and stirred overnight at 70° C. The reaction mixture was cooled to ambient temperature and concentrated under reduced pressure to give the crude sub-title compound that was used without further purification. MS calculated for $C_{21}H_{31}N_3O_4$+H: 390, observed: 390.

d.) (5-Amino-2-propyl-benzoimidazol-1-yl)-acetic acid tert-butyl ester.

HCl (15 mL, 4.0 N solution in dioxane) was added to (5-tert-butoxycarbonyl-amino-2-propyl-benzoimidazol-1-yl)-acetic acid tert-butyl ester (1.9 g, 6.5 mmol) and stirred 2 h at room temperature. The reaction solution was concentrated via rotary evaporation, and then placed on the vacuum line to afford the subtitle compound that was used without further purification. MS calculated for $C_{16}H_{23}N_3O_2$+H: 290, observed: 290.

e.) (5-Benzylamino-2-propyl-benzoimidazol-1-yl)-acetic acid tert-butyl ester.

Sodium triacetoxyborohydride (1.8 g, 8.4 mmol) was added to a solution of benzaldehyde (0.68 mL, 6.5 mmol) and (5-amino-2-propyl-benzoimidazol-1-yl)-acetic acid tert-butyl ester (1.8 g, 6.5 mmol) in DCE (15 mL), and stirred overnight at room temperature. The reaction solution was diluted with H$_2$O. The organic solution was washed with brine, dried over MgSO$_4$, and concentrated to afford the sub-title compound that was used without further purification. MS calculated for $C_{23}H_{29}N_3O_2$+H: 380, observed: 380.

f.) [5-(Acetyl-benzyl-amino)-2-propyl-benzoimidazol-1-yl]-acetic acid tert-butyl ester.

Acetyl chloride (25 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in CH$_2$Cl$_2$ (1 mL), and stirred overnight at room temperature. The reaction solution was diluted with aqueous HCl (1.0 M) and filtered through an Extrelut column. The Extrelut column was washed with CH$_2$Cl$_2$, and the filtrate was concentrated to afford the subtitle compound that was used without further purification. MS calculated for $C_{25}H_{31}N_3O_3$+H: 422, observed: 422.

g.) [5-(Acetyl-benzyl-amino)-2-propyl-benzoimidazol-1-yl]-acetic acid.

[5-(Acetyl-benzyl-amino)-2-propyl-benzoimidazol-1-yl]-acetic acid tert-butyl ester (0.12 mmol) was treated with TFA (2 mL) for 2 hours, concentrated, and purified by preparative LCMS to give the title compound. $^1$H NMR (d$_6$-DMSO) δ7.72 (m, 1H), 7.55 (m, 1H), 7.23 (m, 6H), 5.28 (s, 2H), 4.91 (s, 2H), 2.95 (m, 2H), 1.81 (m, 3H), 1.24 (m, 2H), 0.99 (t, 3H). MS calculated for $C_{21}H_{23}N_3O_3$+H: 366, observed: 366.

EXAMPLE 58

[5-(Benzyl-isobutyryl-amino)-2-propyl-benzoimidazol-1-yl]-acetic acid a.) [5-(Benzyl-isobutyryl-amino)-2-propyl-benzoimidazol-1-yl]-acetic acid tert-butyl ester. (Scheme 2)

Isobutyryl chloride (38 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in CH$_2$Cl$_2$ (1 mL), and stirred overnight at room temperature. The reaction solution was diluted with aqueous HCl (1.0 M) and filtered through an Extrelut column. The Extrelut column was washed with CH$_2$Cl$_2$, and the filtrate was concentrated to afford the subtitle compound that was used without further purification. MS calculated for $C_{27}H_{35}N_3O_3$+H: 450, observed: 450.

b.) [5-(Benzyl-isobutyryl-amino)-2-propyl-benzoimidazol-1-yl]-acetic acid.

[5-(Benzyl-isobutyryl-amino)-2-propyl-benzoimidazol-1-yl]-acetic acid tert-butyl ester (0.12 mmol) was treated with TFA (2 mL) for 2 hours, concentrated, and purified by preparative LCMS to give the title compound. $^1$H NMR (d$_6$-DMSO) δ7.55 (m, 1H), 7.25 (m, 6H), 7.03 (m, 1H), 5.14 (s, 2H), 4.88 (s, 2H), 3.20 (m, 2H), 2.80 (m, 1H), 1.72 (m, 2H), 1.25 (m, 6H), 0.95 (t, 3H). MS calculated for $C_{23}H_{27}N_3O_3$+H: 394, observed: 394.

EXAMPLE 59

{5-[Benzyl-(3-methyl-butyryl)-amino]-2-propyl-benzoimidazol-1-yl}-acetic acid a.) {5-[Benzyl-(3-methyl-butyryl)-amino]-2-propyl-benzoimidazol-1-yl}-acetic acid tert-butyl ester. (Scheme 2)

3-Methyl-butyryl chloride (44 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{28}H_{37}N_3O_3$+H: 464, observed: 464.

b.) {5-[Benzyl-(3-methyl-butyryl)-amino]-2-propyl-benzoimidazol-1-yl}-acetic acid.

{5-[Benzyl-(3-methyl-butyryl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR ($d_6$-DMSO) δ7.48 (d, 1H), 7.21 (m, 6H), 6.92 (m, 1H), 5.08 (s, 2H), 4.89 (s, 2H), 2.72 (t, 2H), 2.00 (m, 3H), 1.71 (m, 2H), 0.99 (t, 3H), 0.79 (m, 6H). MS calculated for $C_{24}H_{29}N_3O_3$+H: 408, observed: 408.

EXAMPLE 60

[5-(Benzyl-cyclopentanecarbonyl-amino)-2-propyl-benzoimidazol-1-yl]-acetic acid a.) [5-(Benzyl-cyclopentanecarbonyl-amino)-2-propyl-benzoimidazol-1-yl]-acetic acid tert-butyl ester. (Scheme 2)

Cyclopentanecarbonyl chloride (43 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{29}H_{37}N_3O_3$+H: 476, observed: 476.

b.) [5-(Benzyl-cyclopentanecarbonyl-amino)-2-propyl-benzoimidazol-1-yl]-acetic acid.

[5-(Benzyl-cyclopentanecarbonyl-amino)-2-propyl-benzoimidazol-1-yl]-acetic acid tert-butyl ester (0.12 mmol) was treated with TFA (2 mL) for 2 hours, concentrated, and purified by preparative LCMS to give the title compound. $^1$H NMR ($d_6$-DMSO) δ7.47 (d, 1H), 7.21 (m, 6H), 6.95 (m, 1H), 5.08 (s, 2H), 4.87 (s, 2H), 2.73 (t, 2H), 1.71 (m, 9H), 1.33 (m, 2H), 0.99 (t, 3H). MS calculated for $C_{25}H_{29}N_3O_3$+H: 420, observed: 420.

EXAMPLE 61

[5-(Benzyl-cyclohexanecarbonyl-amino)-2-propyl-benzoimidazol-1-yl]-acetic acid a.) [5-(Benzyl-cyclohexanecarbonyl-amino)-2-propyl-benzoimidazol-1-yl]-acetic acid tert-butyl ester. (Scheme 2)

Cyclohexanecarbonyl chloride (48 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{39}N_3O_3$+H: 490, observed: 490.

b.) [5-(Benzyl-cyclohexanecarbonyl-amino)-2-propyl-benzoimidazol 1-yl]-acetic acid.

[5-(Benzyl-cyclohexanecarbonyl-amino)-2-propyl-benzoimidazol-1-yl]-acetic acid tert-butyl ester (0.12 mmol) was treated with TFA (2 mL) for 2 hours, concentrated, and purified by preparative LCMS to give the title compound. $^1$H NMR ($d_6$-DMSO) δ7.50 (d, 1H), 7.21 (m, 6H), 6.95 (m, 1H), 5.09 (s, 2H), 4.86 (s, 2H), 2.72 (t, 2H), 2.18 (m, 1H), 1.60 (m, 9H), 1.10 (m, 1H), 0.99 (t, 3H), 0.85 (m, 2H). MS calculated for $C_{26}H_{31}N_3O_3$+H: 434, observed: 434.

EXAMPLE 62

{5-[Benzyl-(3-chloro-benzoyl)-amino]-2-propyl-benzoimidazol-1-yl}-acetic acid a.) {5-[Benzyl-(3-chloro-benzoyl)-amino]-2-propyl-benzoimidazol-1-yl}-acetic acid tert-butyl ester. (Scheme 2)

3-Chloro-benzoyl chloride (46 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{32}ClN_3O_3$+H: 518, observed: 518.

b.) {5-[Benzyl-(3-chloro-benzoyl)-amino]-2-propyl-benzoimidazol-1-yl}-acetic acid.

{5-[Benzyl-(3-chloro-benzoyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR ($d_6$-DMSO) δ7.89 (m, 1H), 7.71 (m, 1H), 7.52 (m, 1H), 7.45 (m, 1H), 7.21 (m, 6H), 6.91 (m, 1H), 5.11 (s, 2H), 4.91

(s, 2H), 2.65 (t, 2H), 1.71 (m, 2H), 0.92 (t, 3H). MS calculated for $C_{26}H_{24}ClN_3O_3$+H: 462, observed: 462.

EXAMPLE 63

{5-[Benzyl-(4-chloro-benzoyl)-amino]-2-propyl-benzoimidazol-1-yl}-acetic acid a.) {5-[Benzyl-(4-chloro-benzoyl)-amino]-2-propyl-benzoimidazol-1-yl}-acetic acid tert-butyl ester. (Scheme 2)

4-Chloro-benzoyl chloride (46 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{32}ClN_3O_3$+H: 518, observed: 518.

b.) {5-[Benzyl-(4-chloro-benzoyl)-amino]-2-propyl-benzoimidazol-1-yl}-acetic acid.

{5-[Benzyl-(4-chloro-benzoyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. MS calculated for $C_{26}H_{24}ClN_3O_3$+H: 462, observed: 462.

EXAMPLE 64

{5-[Benzyl-(2-fluoro-benzoyl)-amino]-2-propyl-benzoimidazol-1-yl}-acetic acid a.) {5-[Benzyl-(2-fluoro-benzoyl)-amino]-2-propyl-benzoimidazol-1-yl}-acetic acid tert-butyl ester. (Scheme 2)

2-Fluoro-benzoyl chloride (42 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{32}FN_3O_3$+H: 502, observed: 502.

b.) {5-[Benzyl-(2-fluoro-benzoyl)-amino]-2-propyl-benzoimidazol-1-yl}-acetic acid.

{5-[Benzyl-(2-fluoro-benzoyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. MS calculated for $C_{26}H_{24}FN_3O_3$+H: 446, observed: 446.

EXAMPLE 65

{5-[Benzyl-(3-fluoro-benzoyl)-amino]-2-propyl-benzoimidazol-1-yl}-acetic acid a.) {5-[Benzyl-(3-fluoro-benzoyl)-amino]-2-propyl-benzoimidazol-1-yl}-acetic acid tert-butyl ester. (Scheme 2)

3-Fluoro-benzoyl chloride (42 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{32}FN_3O_3$+H: 502, observed: 502.

b.) {5-[Benzyl-(3-fluoro-benzoyl)-amino]-2-propyl-benzoimidazol-1-yl}-acetic acid.

{5-[Benzyl-(3-fluoro-benzoyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR ($d_6$-DMSO) δ 7.79 (m, 1H), 7.68 (m, 1H), 7.55 (m, 2H), 7.21 (m, 6H), 7.02 (m, 1H), 6.92 (m, 1H), 5.11 (s, 2H), 4.99 (s, 2H), 2.68 (t, 2H), 1.71 (m, 2H), 0.95 (t, 3H). MS calculated for $C_{26}H_{24}FN_3O_3$+H: 446, observed: 446.

EXAMPLE 66

{5-[Benzyl-(4-fluoro-benzoyl)-amino]-2-propyl-benzoimidazol-1-yl}-acetic acid a.) {5-[Benzyl-(4-fluoro-benzoyl)-amino]-2-propyl-benzoimidazol-1-yl}-acetic acid tert-butyl ester. (Scheme 2)

4-Fluoro-benzoyl chloride (42 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{32}FN_3O_3$+H: 502, observed: 502.

b.) {5-[Benzyl-(4-fluoro-benzoyl)-amino]-2-propyl-benzoimidazol-1-yl}-acetic acid.

{5-[Benzyl-(4-fluoro-benzoyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR (d6-DMSO) δ 8.02 (m, 1H), 7.29 (m, 7H), 7.01 (m, 3H), 6.87 (m, 1H), 5.11 (s, 2H), 4.98 (s, 2H), 2.68 (t, 2H), 1.71 (m, 2H), 0.95 (t, 3H). MS calculated for $C_{26}H_{24}FN_3O_3$+H: 446, observed: 446.

EXAMPLE 67

{5-[Benzyl-(3,4-difluoro-benzoyl)-amino]-2-propyl-benzoimidazol-1-yl}-acetic acid a.) {5-[Benzyl-(3,4-difluoro-benzoyl)-amino]-2-propyl-benzoimidazol-1-yl}-acetic acid tert-butyl ester. (Scheme 2)

3,4-Difluoro-benzoyl chloride (45 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{31}F_2N_3O_3$+H: 520, observed: 520.

b.) {5-[Benzyl-(3,4-difluoro-benzoyl)-amino]-2-propyl-benzoimidazol-1-yl}-acetic acid.

{5-[Benzyl-(3,4-difluoro-benzoyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR ($d_6$-DMSO) δ7.48 (m, 1H), 7.26 (m, 7H), 7.12 (m, 2H), 6.81 (m, 1H), 5.08 (s, 2H), 4.31 (s, 2H), 2.62 (t, 2H), 1.71 (m, 2H), 0.92 (t, 3H). MS calculated for $C_{26}H_{23}F_2N_3O_3$+H: 464, observed: 464.

EXAMPLE 68

{5-[Benzyl-(2,6-difluoro-benzoyl)-amino]-2-propyl-benzoimidazol-1-yl}-acetic acid a.) {5-[Benzyl-(2,6-difluoro-benzoyl)-amino]-2-propyl-benzoimidazol-1-yl}-acetic acid tert-butyl ester. (Scheme 2)

2,6-Difluoro-benzoyl chloride (45 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{30}H_{31}F_2N_3O_3$+H: 520, observed: 520.

b.) {5-[Benzyl-(2,6-difluoro-benzoyl)-amino]-2-propyl-benzoimidazol-1-yl}-acetic acid.

{5-[Benzyl-(2,6-difluoro-benzoyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR ($d_6$-DMSO) δ7.28 (m, 8H), 6.93 (m, 2H), 6.79 (m, 1H), 5.09 (s, 2H), 4.58 (s, 2H), 2.61 (t, 2H), 1.69 (m, 2H), 0.92 (t, 3H). MS calculated for $C_{26}H_{23}F_2N_3O_3$+H: 464, observed: 464.

EXAMPLE 69

{5-[Benzyl-(3-methyl-thiophene-2-carbonyl)-amino]-2-propyl-benzoimidazol-1-yl}-acetic acid a.) {5-[Benzyl-(3-methyl-thiophene-2-carbonyl)-amino]-2-propyl-benzoimidazol-1-yl}-acetic acid tert-butyl ester. (Scheme 2)

3-Methyl-thiophene-2-carbonyl chloride (41 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{29}H_{33}N_3O_3S$+H: 504, observed: 504.

b.) {5-[Benzyl-(3-methyl-thiophene-2-carbonyl)-amino]-2-propyl-benzoimidazol-1-yl}-acetic acid.

{5-[Benzyl-(3-methyl-thiophene-2-carbonyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR ($d_6$-DMSO) δ7.68 (d, 1H), 7.29 (m, 5H), 7.02 (m, 2H), 6.85 (d, 1H), 6.71 (d, 1H), 5.09 (s, 2H), 4.75 (s, 2H), 2.65 (t, 2H), 1.71 (m, 2H), 0.92 (t, 3H). MS calculated for $C_{25}H_{25}N_3O_3S$+H: 448, observed: 448.

EXAMPLE 70

{5-[Benzyl-(thiophene-2-carbonyl)-amino]-2-propyl-benzoimidazol-1-yl}-acetic acid a.) {5-[Benzyl-(thiophene-2-carbonyl)-amino]-2-propyl-benzoimidazol-1-yl}-acetic acid tert-butyl ester. (Scheme 2)

Thiophene-2-carbonyl chloride (38 µL, 0.36 mmol) was added to a solution of (5-benzylamino-2-propyl-benzoimidazol-1-yl)-acetic acid tert-butyl ester (45 mg, 0.12 mmol), DIEA (41 µL, 0.24 mmol) and DMAP (15 mg, 0.12 mmol) in $CH_2Cl_2$ (1 mL), and stirred overnight at room temperature. The reaction solution was diluted with aqueous HCl (1.0 M) and filtered through an Extrelut column. The Extrelut column was washed with $CH_2Cl_2$, and the filtrate was concentrated to afford the subtitle compound that was used without further purification. MS calculated for $C_{28}H_{31}N_3O_3S$+H: 490, observed: 490.

b.) {5-[Benzyl-(thiophene-2-carbonyl)-amino]-2-propyl-benzoimidazol-1-yl}-acetic acid.

{5-[Benzyl-(thiophene-2-carbonyl)-amino]-2-propyl-benzoimidazol-1-yl}-acetic acid tert-butyl ester (0.12 mmol) was treated with TFA (2 mL) for 2 hours, concentrated, and purified by preparative LCMS to give the title compound. $^1$H NMR (d6-DMSO) δ7.58 (d, 1H), 7.40 (d, 1H), 7.28 (m, 6H), 6.92 (m, 1H), 6.83 (m, 1H), 6.61 (d, 1H), 5.04 (s, 2H), 4.82 (s, 2H), 2.71 (t, 2H), 1.78 (m, 2H), 0.98 (t, 3H). MS calculated for $C_{24}H_{23}N_3O_3S+H$: 434, observed: 434.

EXAMPLE 71

CRTH-2 Binding Assay

A CRTH2 binding assay was developed to measure the ability of compounds to inhibit the binding of $PGD_2$ to human CRTH2 using a scintillation proximity assay.

Membranes containing hCRTH2 receptors were prepared from 293EBNA-hCRTH2 cells (a 293EBNA cell line stably expressing human CRTH2). The cells were grown to confluency, harvested and washed with PBS. The cells were resuspended in 10 mM Hepes pH 7.4, 1 mM EDTA and protease inhibitors and incubated for 30 min on ice. The cells were homogenized and centrifuged for 10 min at 1000×g. The supernate was centrifuged for 30 min at 100,000×g and the membrane pellet was then resuspended in 10 mM Hepes pH 7.4 and 1 mM EDTA. The protein concentration of the membrane preparation was determined by Bradford assay (Bio-Rad).

The ability of compounds to inhibit the interaction of $PGD_2$ to human CRTH2 was determined at seven compound concentrations. Compounds were serially diluted in DMSO then diluted into CRTH2 buffer (10 mM Hepes pH 7.4, 1 mM EDTA, 10 mM $MnCl_2$) to six times the final desired concentration. 20 μL of the diluted compounds were transferred into non-surface binding 96-well plates (Corning). Each concentration was done in triplicate. In addition to test compounds, each plate contained 12 control wells. Six of these wells contained 20 μL of CRTH2 buffer. These wells were used to measure total binding. Six wells contained 20 μL of CRTH2 buffer plus 1.5 mM indomethacin. These wells were used to measure non-specific binding. Next, 293EBNA-hCRTH2 membranes were resuspended in CRTH2 buffer with glycerol (10 mM Hepes pH 7.4, 1 mM EDTA, 10 mM $MnCl_2$, 25% glycerol) so that the final concentration was approximately 20 μg/100 μL. Polylysine-coated yttrium silicate SPA beads (Amersham) were added to the membrane mix to a concentration of 0.4 mg/100 μL and finally $^3H$-$PGD_2$ was added to the membrane/SPA bead mix to 3.6 nM. 100 μL of the membrane/SPA bead/$^3H$-$PGD_2$ mix was added to each well of the non-surface binding plates containing the diluted compound or controls. The plates were incubated for 2 hours at room temperature with shaking and then the plates were counted on a Microbeta scintillation counter (Perkin Elmer) for 1 min per well.

$IC_{50}$ values were determined from the experimental results by nonlinear regression using Prism 4.0 software. The $IC_{50}$ values were then used in conjunction with the $K_d$ for hCRTH2 and the $^3H$-$PGD_2$ concentration used in the experiment to calculate the $K_i$ for each compound. The results are shown in Table 1.

TABLE 1

| Ex No. | Compound | $K_i$ (μM) |
|---|---|---|
| 1 | 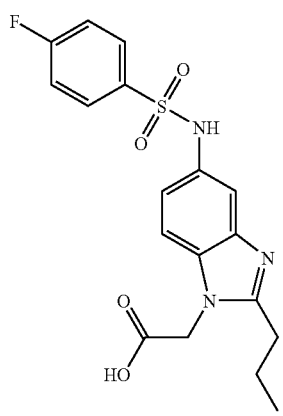 | <1 |
| 2 | 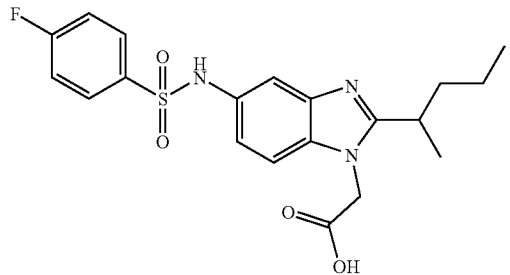 | <1 |

TABLE 1-continued

| Ex No. | Compound | $K_i$ (μM) |
|---|---|---|
| 3 | | <1 |
| 4 | | <10 |
| 5 | | <10 |
| 6 | | <10 |
| 7 | | <10 |
| 8 | | >10 |

TABLE 1-continued

| Ex No. | Compound | $K_i$ (μM) |
|---|---|---|
| 9 | | >10 |
| 10 | | >10 |
| 11 | | <10 |
| 12 | | <1 |
| 13 | | <1 |

TABLE 1-continued

| Ex No. | Compound | $K_i$ (μM) |
|---|---|---|
| 14 | | <0.1 |
| 15 | | <1 |
| 16 | | <1 |
| 17 | | <1 |

TABLE 1-continued

| Ex No. | Compound | $K_i$ (μM) |
|---|---|---|
| 18 | | <1 |
| 19 | | <0.1 |
| 20 | | <0.1 |
| 21 | | <0.1 |

TABLE 1-continued

| Ex No. | Compound | $K_i$ (μM) |
|---|---|---|
| 22 | | <1 |
| 23 | | <0.1 |
| 24 | | <1 |
| 25 | | <10 |

TABLE 1-continued

| Ex No. | Compound | $K_i$ (μM) |
|---|---|---|
| 26 | | <10 |
| 27 | | <1 |
| 28 | | <1 |
| 29 | | <1 |

TABLE 1-continued

| Ex No. | Compound | $K_i$ (μM) |
|---|---|---|
| 30 | | <1 |
| 31 | | <1 |
| 32 | | <1 |
| 33 | | <0.1 |

TABLE 1-continued

| Ex No. | Compound | $K_i$ (μM) |
|---|---|---|
| 34 | | <1 |
| 35 | | <10 |
| 36 | | <1 |
| 37 | | <1 |

TABLE 1-continued

| Ex No. | Compound | $K_i$ (μM) |
|---|---|---|
| 38 | | <10 |
| 39 | | <1 |
| 40 | | >10 |
| 41 | | <0.1 |

TABLE 1-continued

| Ex No. | Compound | $K_i$ (μM) |
|---|---|---|
| 42 | (3-chlorobenzyl)-N-(4-fluorophenylsulfonyl) substituted 2-propyl-benzimidazole-1-acetic acid | <0.1 |
| 43 | (4-chlorobenzyl)-N-(4-fluorophenylsulfonyl) substituted 2-propyl-benzimidazole-1-acetic acid | <0.1 |
| 44 | (2,3-dichlorobenzyl)-N-(4-fluorophenylsulfonyl) substituted 2-propyl-benzimidazole-1-acetic acid | <0.1 |
| 45 | (2-trifluoromethylbenzyl)-N-(4-fluorophenylsulfonyl) substituted 2-propyl-benzimidazole-1-acetic acid | <1 |

TABLE 1-continued

| Ex No. | Compound | $K_i$ (μM) |
|---|---|---|
| 46 | | <1 |
| 47 | | <0.1 |
| 48 | | <0.1 |

TABLE 1-continued

| Ex No. | Compound | $K_i$ (μM) |
|---|---|---|
| 49 | (structure) | <0.1 |
| 50 | (structure) | <1 |
| 51 | (structure) | <1 |

TABLE 1-continued
| Ex No. | Compound | $K_i$ (µM) |
|---|---|---|
| 52 | 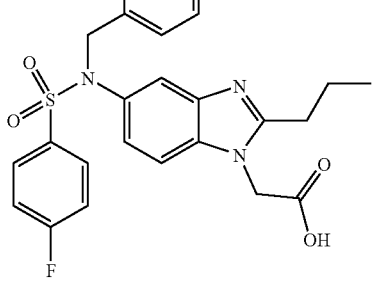 | <0.1 |
| 53 | 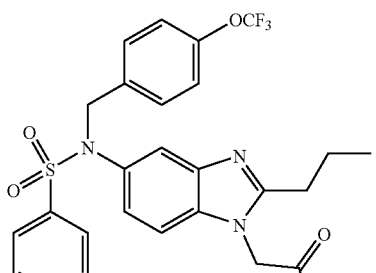 | <0.1 |
| 54 | 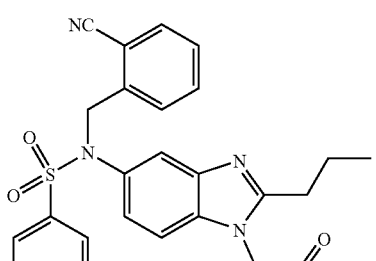 | <1 |
| 55 | 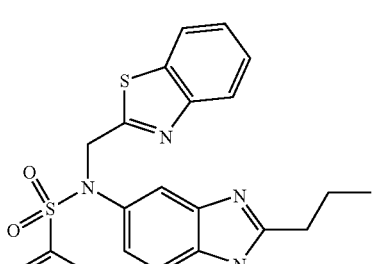 | <0.1 |

TABLE 1-continued

| Ex No. | Compound | $K_i$ (μM) |
|---|---|---|
| 56 | | <0.1 |
| 57 | | <10 |
| 58 | | >10 |
| 59 | | <10 |

TABLE 1-continued

| Ex No. | Compound | $K_i$ (μM) |
|---|---|---|
| 60 | | <10 |
| 61 | | <10 |
| 62 | | <1 |
| 63 | | <1 |

TABLE 1-continued

| Ex No. | Compound | $K_i$ (μM) |
|---|---|---|
| 64 | (2-fluorobenzoyl-N-benzyl)-5-amino-2-propyl-benzimidazol-1-yl acetic acid | >10 |
| 65 | (3-fluorobenzoyl-N-benzyl)-5-amino-2-propyl-benzimidazol-1-yl acetic acid | <10 |
| 66 | (4-fluorobenzoyl-N-benzyl)-5-amino-2-propyl-benzimidazol-1-yl acetic acid | <1 |
| 67 | (3,4-difluorobenzoyl-N-benzyl)-5-amino-2-propyl-benzimidazol-1-yl acetic acid | <1 |

TABLE 1-continued

| Ex No. | Compound | $K_i$ (μM) |
|---|---|---|
| 68 | (structure: 2,6-difluorobenzoyl-N-benzyl linked to 5-amino-2-propyl-benzimidazole-1-acetic acid) | <10 |
| 69 | (structure: thiophene-2-carbonyl with 3-methyl, N-benzyl linked to 5-amino-2-propyl-benzimidazole-1-acetic acid) | <0.1 |
| 70 | (structure: thiophene-2-carbonyl, N-benzyl linked to 5-amino-2-propyl-benzimidazole-1-acetic acid) | <0.1 |

EXAMPLE 72

CRTH2 Fluorescent Imaging Assay

The ability of the disclosed compounds to act as agonists for the hCRTH2 receptor was determined by their ability to cause increases in intracellular calcium via binding to the CRTH2 receptor. The compounds were also tested for their ability to act as antagonists for the hCRTH2 receptor as measured by the ability of the compounds to block the increase in intracellular calcium normally caused by PGD$_2$ binding to the CRTH2 receptor.

Assays were performed on HEK 293EBNA-hCRTH2 cells that had been grown in DMEM media containing 10% FBS, 3 μL/mL puromycin and 1% penicillin/streptomycin/glutamine (PSG) at 37° C. in 5% CO$_2$ or on HT1080-hCRTH2 cells (a HT1080 cell line stably expressing human CRTH2) that had been grown in alphaMEM media containing 10% FBS, 500 μg/ml hygromycin, 200 nM methotrexate and 1% PSG at 37° C. in 5% CO$_2$.

For the assay, HEK 293EBNA-hCRTH2 cells or HT1080-hCRTH2 cells were grown to approximately 90% confluency and then dislodged from the plate with Trypsin-EDTA, resuspended in DMEM media, seeded in 384 well plates at 2×10$^4$ cells per well and incubated overnight at 37° C. The cells were loaded with a calcium sensing dye by removing the growth media and replacing it with 30 μL of dye loading Ringer's buffer (136 mM CsCl, 5.4 mM D-Glucose, 20 mM Hepes pH 7.4, 2.1 mM MgCl$_2$, 0.8 mM CaCl$_2$, 0.2% BSA with 1× Calcium3Dye (Molecular Devices) and 2.5 mM Probenecid (Sigma)) per well. The cells were incubated at 37° C. for 1 hour to allow the dye to enter the cells. Compounds were serially diluted in DMSO and then diluted to 4× their final concentration with Ringer's buffer. The compounds were added to a 384 well plate in quadruplicate. In addition to test compounds, several wells contained Ringer's buffer with DMSO. These wells serve as control wells. 10 μL was transferred from compound/control plate to the plate containing cells loaded with dye by a fluorescent imaging plate reader (Molecular Devices). The fluorescence was measured every 4 seconds for 4 minutes. These measurements indicated the level of intracellular calcium. Increases in fluorescence relative to wells containing buffer only indicated an agonist effect of the compound. Measurement at various compound concentrations allowed one to determine the EC$_{50}$ for these compounds. Following the 4 minute incubation with compound, 20 μL of Ringer's buffer with either 10 nM or 500 nM PGD$_2$ (approximate EC$_{75}$ for PGD$_2$ in HEK 293EBNA-hCRTH2 cells and HT1080-hCRTH2 cells, respectively) was added to the wells. Inhibition by the compounds of the calcium response due to antagonism of PGD$_2$ action on CRTH2 is reflected by a decrease in fluorescent signal relative to wells containing no compound. The fluorescence was measured every 2 seconds for 10 seconds before addition of PGD$_2$ and every 2 seconds for 110 seconds following addition. Measurement at various compound concentrations allowed one to determine the IC$_{50}$ for the compounds. EC$_{50}$ and IC$_{50}$ values were determined from the experimental results by nonlinear regression using the Prism 4.0 software. The results are shown in Table 2.

TABLE 2

| Example Number | RAGE hCRTH2 IC$_{50}$ (μM) |
| --- | --- |
| 43 | 0.051 |
| 46 | 0.375 |
| 47 | 0.022 |
| 49 | 0.047 |
| 70 | 0.007 |

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound selected from:
{5-[benzyl-(4-fluoro-benzenesulfonyl)-amino]-2-propyl-benzoimidazol-1-yl}-acetic acid;
{5-[(4-fluoro-benzenesulfonyl)-(4-fluoro-benzyl)-amino]-2-propyl-benzoimidazol-1-yl}-acetic acid;
{5-[(4-fluoro-benzenesulfonyl)-(3-methyl-butyl)-amino]-2-propyl-benzoimidazol-1-yl}-acetic acid;
{5-[(4-fluoro-benzenesulfonyl)-isopropyl-amino]-2-propyl-benzoimidazol-1-yl}-acetic acid;
{5-[(2,3-dihydro-benzo[1,4]dioxin-2-ylmethyl)-(4-fluoro-benzenesulfonyl)-amino]-2-propyl-benzoimidazol-1-yl}-acetic acid;
{5-[(2-chloro-benzyl)-(4fluoro-benzenesulfonyl)-amino]-2-propyl-benzoimidazol-1-yl}-acetic acid:
{5-[(3-chloro-benzyl)-(4-fluoro-benzenesulfonyl)-amino]-2-propyl-benzoimidazol-1-yl}-acetic acid;
{5-[(4-chloro-benzyl)-(4-fluoro-benzenesulfonyl)-amino]-2-propyl-benzoimidazol-1-yl}-acetic acid;
{5-[(2,3-dichloro-benzyl)-(4-fluoro-benzenesulfonyl)-amino]-2-propyl-benzoimidazol-1-yl}-acetic acid;
{5-[[2-(4-chloro-phenoxy)-ethyl]-(4-fluoro-benzenesulfonyl)-amino]-2-propyl-benzoimidazol-1-yl}-acetic acid;
{5-[(4-fluoro-benzenesulfonyl)-(3-phenyl-propyl)-amino]-2-propyl-benzoimidazol-1-yl}-acetic acid;
{5-[(4-fluorobenzenesulfonyl)-(3-phenoxy-propyl)-amino]-2-propyl-benzoimidazol-1-yl}-acetic acid;
{5-[(4-cyano-benzyl)-(4-fluoro-benzenesulfonyl)-amino]-2-propyl-benzoimidazol-1-yl}-acetic acid;
{5-[(4-trifluoromethoxybenzyl)-(4-fluoro-benzenesulfonyl)-amino]-2-propyl-benzoimidazol-1-yl}-acetic acid;
{5-[benzothiazol-2-ylmethyl-(4-fluoro-benzenesulfonyl)-amino]-2-propyl-benzoimidazol-1-yl}-acetic acid; and
{5-[but-2-enyl-(4-fluoro-benzenesulfonyl)-amino]-2-propyl-benzoimidazol-1-yl}-acetic acid;
or a pharmaceutically acceptable salt thereof.

2. A compound selected from:
[2(1,5-dimethyl-hex-4-enyl)-5-(4-fluoro-benzenesulfonylamino)-benzoimidazol-1-yl]-acetic acid;
[2(1-ethyl-pentyl)-5-(4-fluoro-benzenesulfonylamino)-benzoimidazol-1-yl]-acetic acid;
[2(2-allyloxycarbonylamino-enyl)-5-(4-fluoro-benzenesulfonylamino)-benzoimidazol-1-yl]-acetic acid;
[2-but-1-enyl-5-(4-fluoro-benzenesulfonylamino)-benzoimidazol-1-yl]-acetic acid;
[2-butyl-5- (4-fluoro-benzenesulfonylamino)-benzoimidazol-1-yl]-acetic acid;
[2-ethyl-5- (4-fluoro-benzenesulfonylamino)-benzoimidazol-1-yl]-acetic acid;
[2-propyl-5- (1,1,3-trioxo-1,3-dihydro-1λ$^6$-benzo[d]isothiazol-2-yl)-benzoimidazol-1-yl]-acetic acid;
[5-(4-fluoro-benzenesulfonylamino)-2-(2-methylsulfanyl-ethyl)-benzoimidazol-1-yl]-acetic acid;
[5-(4-fluoro-benzenesulfonylamino)-2-(1-methyl-butyl)-benzoimidazol-1-yl]-acetic acid;
[5-(4-fluoro-benzenesulfonylamino)-2-(2,4,4-trimethyl-pentyl)-benzoimidazol-1-yl]-acetic acid;
[5-(4-fluoro-benzenesulfonylamino)-2-isobutyl-benzoimidazol-1-yl]-acetic acid;
[5-(4-fluoro-benzenesulfonylamino)-2-isopropyl-benzoimidazol-1-yl]-acetic acid;
[5-(4-fluoro-benzenesulfonylamino)-2-pentyl-benzoimidazol-1-yl]-acetic acid;
[5-(4-fluoro-benzenesulfonylamino)-2-propyl-benzoimidazol-1-yl]-acetic acid;
{2-butyl-5-[(4-fluoro-benzenesulfonylamino)-methyl-amino]-benzoimidazol-1-yl}-acetic acid;
{4-[benzyl-(4-fluoro-phenylmethanesulfonyl)-amino]-2-propyl-benzoimidazol-1-yl}-acetic acid;
{4-[(3-fluoro-benzenesulfonyl)-(4-fluoro-benzyl)-amino]-2-propyl-benzoimidazol-1-yl}-acetic acid;
{4-[(3-fluoro-benzenesulfonyl)-(2-methoxy-ethyl)-amino]-2-propyl-benzoimidazol-1-yl}-acetic acid;
{4-[(3-fluoro-benzenesulfonyl)-(3-methyl-butyl)-amino]-2-propyl-benzoimidazol-1-yl}-acetic acid;
{4-[(3-fluoro-benzenesulfonyl)-isopropyl-amino]-2-propyl-benzoimidazol-1-yl}-acetic acid;
{4-[benzyl-(3-fluoro-benzenesulfonyl)-amino]-2-propyl-benzoimidazol-1-yl}-acetic acid;
{5-[(2-cyano-benzyl)-(4-fluoro-benzenesulfonyl)-amino]-2-propyl-benzoimidazol-1-yl}-acetic acid
{5-[(2-fluoro-benzenesulfonyl)-(4-fluoro-benzyl)-amino]-2-propyl-benzoimidazol-1-yl}-acetic acid;
{5-[(2-trifluoromethyl-benzyl)-(4-fluoro-benzenesulfonyl)-amino]-2-propyl-benzoimidazol-1-yl}-acetic acid;
{5-[(3,5-dimethyl-isoxazol-4-ylmethyl)-(4-fluoro-benzenesulfonyl)-amino]-2-propyl-benzoimidazol-1-yl}-acetic acid;
{5-[(3-fluoro-benzenesulfonyl)-(4-fluoro-benzyl)-amino]-2-propyl-benzoimidazol-1-yl}-acetic acid;
{5-[(4-fluoro-benzenesulfonyl)-(2-methyl-thiazol-4-ylmethyl)-amino]-2-propyl-benzoimidazol-1-yl}-acetic acid;
{5-[(4-fluoro-benzenesulfonyl)-(3-fluoro-benzyl)-amino]-2-propyl-benzoimidazol-1-yl}-acetic acid;
{5-[(4-fluoro-benzenesulfonyl)-(3-trifluoromethyl-benzyl)-amino]-2-propyl-benzoimidazol-1-yl}-acetic acid;
{5-[(cyclohexyl)-(4-fluoro-benzenesulfonyl)-amino]-2-propyl-benzoimidazol-1-yl}-acetic acid;
{5-[benzyl-(4-fluoro-benzenesulfonyl)-amino]-2-butyl-benzoimidazol-1-yl}-acetic acid;

{5-[benzyl-(4-fluoro-benzenesulfonyl)-amino]-2-isopropyl-benzoimidazol-1-yl}-acetic acid;

{5-[ethanesulfonyl-(4-fluoro-benzyl)-amino]-2-propyl-benzoimidazol-1-yl}-acetic acid;

{5-[ethoxycarbonylmethyl-(4-fluoro-benzenesulfonyl)-amino]-2-propyl-benzoimidazol-1-yl}-acetic acid; and {7-[benzyl-(4-fluoro-benzenesulfonyl)-amino]-2-propyl-benzoimidazol-1-yl}-acetic acid;

or a pharmaceutically acceptable salt thereof.

3. A kit comprising a compound according to claim 1, or a pharmaceutically acceptable salt thereof, and instructions for administering said compound, or pharmaceutically acceptable salt thereof, to an animal.

4. The kit of claim 3, further comprising an additional therapeutic agent.

5. A kit comprising a compound according to claim 2, or a pharmaceutically acceptable salt thereof, and instruction for administering said compound, or pharmaceutically acceptable salt thereof, to an animal.

6. The kit according to claim 5, further comprising an additional therapeutic agent.

* * * * *